United States Patent
Richmond et al.

(10) Patent No.: US 12,403,105 B2
(45) Date of Patent: Sep. 2, 2025

(54) DIAGNOSIS AND TREATMENT OF VITILIGO

(71) Applicant: University of Massachusetts, Boston, MA (US)

(72) Inventors: Jillian M. Richmond, Dayville, CT (US); John E. Harris, Sterling, MA (US); James Pennock Strassner, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 0 days.

(21) Appl. No.: 18/805,702

(22) Filed: Aug. 15, 2024

(65) Prior Publication Data

US 2024/0398730 A1    Dec. 5, 2024

Related U.S. Application Data

(60) Continuation of application No. 18/607,636, filed on Mar. 18, 2024, which is a continuation of application No. 18/234,923, filed on Aug. 17, 2023, now abandoned, which is a continuation of application No. 17/667,699, filed on Feb. 9, 2022, now abandoned, which is a division of application No. 16/608,116, filed as application No. PCT/US2018/029185 on Apr. 24, 2018, now Pat. No. 11,278,505.

(60) Provisional application No. 62/489,191, filed on Apr. 24, 2017.

(51) Int. Cl.
    *A61K 31/137* (2006.01)
    *A61K 45/06* (2006.01)
    *A61P 17/00* (2006.01)
    *A61P 37/06* (2006.01)

(52) U.S. Cl.
    CPC ............ *A61K 31/137* (2013.01); *A61P 17/00* (2018.01); *A61K 45/06* (2013.01); *A61P 37/06* (2018.01)

(58) Field of Classification Search
    CPC ....... A61K 31/137; A61K 45/06; A61P 17/00; A61P 37/06
    USPC ....................................... 424/144.1
    See application file for complete search history.

(56) References Cited

U.S. PATENT DOCUMENTS

| | | |
|---|---|---|
| 7,736,638 B2 | 6/2010 | Savio et al. |
| 8,580,841 B2 | 11/2013 | Jones et al. |
| 9,028,830 B2 | 5/2015 | Naoya et al. |
| 11,278,505 B2 | 3/2022 | Richmond et al. |
| 2005/0048542 A1 | 3/2005 | Baker et al. |
| 2009/0176744 A1 | 7/2009 | Liu et al. |
| 2012/0251613 A1 | 10/2012 | Jain et al. |
| 2016/0235762 A1 | 8/2016 | Koziak et al. |
| 2016/0287668 A1 | 10/2016 | Tankovich |
| 2021/0100758 A1 | 4/2021 | Richmond et al. |
| 2022/0273589 A1 | 9/2022 | Richmond et al. |

FOREIGN PATENT DOCUMENTS

| | | |
|---|---|---|
| WO | WO 2003/017935 | 3/2003 |
| WO | WO 2007/018564 | 2/2007 |
| WO | WO 2009/002562 | 12/2008 |
| WO | WO 2014/191822 | 12/2014 |
| WO | WO 2014/191823 | 12/2014 |
| WO | WO 2017/046200 | 3/2017 |

OTHER PUBLICATIONS

Adachi "Hair follicle-derived IL-7 and IL~15 mediate skin-resident memory T cell homeostasis and lymphoma," Nature Medicine, Nov. 2015, 21(11):1272-81.
Agarwal et al., "Simvastatin prevents and reverses depigmentation in a mouse model of vitiligo." Journal of Investigative Dermatology, Apr. 1, 2015, 135(4):1080-8.
Ahmadian et al., "Single-nucleotide polymorphism analysis by pyrosequencing," Analytical Biochemistry, Apr. 10, 2000, 280(1):103-10.
Alikhan et al., "Vitiligo: a comprehensive overview: part I. Introduction, epidemiology, quality of life, diagnosis, differential diagnosis, associations, histopathology, etiology, and work-up," Journal of the American Academy of Dermatology, Sep. 1, 2011, 65(3):473-91.
Altschul et al., "Basic local alignment search tool," Journal of Molecular Biology, Oct. 5, 1990, 215(3):403-10.
Antonelli et al., "Circulating chemokine (CXC motif) ligand (CXCL) 9 is increased in aggressive chronic autoimmune thyroiditis, in association with CXCL10," Cytokine, Aug. 1, 2011, 55(2):288-93.
Aoyama et al., "Low-dose IL-2 for in vivo expansion of CD4+ and CD8+ regulatory T cells in nonhuman primates," American Journal of Transplantation, Sep. 2012, 12(9):2532-7.
Ariotti et al., "Skin-resident memory CD8+ T cells trigger a state of tissue-wide pathogen alert," Science, Oct. 3, 2014, 346(6205):101-5.
AU Office Action in Australian Appln. No. 2018257917, dated Feb. 7, 2023, 7 pages.
Babu et al., "Punch grafting versus suction blister epidermal grafting in the treatment of stable lip vitiligo," Dermatologic Surgery, Feb. 3, 2008, 34(2):166-78.
Baigude et al., "Strategies to antagonize miRNA functions in vitro and in vivo," Nanomedicine, Nov. 2014, 9(16):2545-55.
Bartel et al., "Isolation of new ribozymes from a large pool of random sequences [see comment]," Science, Sep. 10, 1993, 261(5127):1411-8.
Beaudry et al., "Directed evolution of an RNA enzyme," Science, Jul. 31, 1992, 257(5070):635-41.
Becker et al., "Interleukin 15 is required for proliferative renewal of virus-specific memory CD8 T cells," The Journal of Experimental Medicine, Jun. 17, 2002, 195(12):1541-8.

(Continued)

*Primary Examiner* — Kristin A Vajda
(74) *Attorney, Agent, or Firm* — Fish & Richardson P.C.

(57) ABSTRACT

Methods of diagnosing and treating vitiligo.

9 Claims, 31 Drawing Sheets

(56) References Cited

OTHER PUBLICATIONS

Benton et al., "Screening lambdagt recombinant clones by hybridization to single plaques in situ," Science, Apr. 8, 1977, 196(4286):180-2.
Bernard et al., "Real-time PCR technology for cancer diagnostics," Clinical Chemistry, Aug. 1, 2002, 48(8):1178-85.
Bernardo et al., "miRNA therapeutics: a new class of drugs with potential therapeutic applications in the heart," Future Medicinal Chemistry, Sep. 2015, 7(13):1771-92.
Bhatnagar et al., "Psoralen and ultraviolet A and narrow-band ultraviolet B in inducing stability in vitiligo, assessed by vitiligo disease activity score: an open prospective comparative study," Journal of the European Academy of Dermatology and Venereology, Nov. 2007, 21(10):1381-5.
Bianchi et al., "A serum circulating miRNA diagnostic test to identify asymptomatic high-risk individuals with early stage lung cancer," EMBO Molecular Medicine, Aug. 1, 2011, 3(8):495-503.
Bigaud et al. Second generation S1P pathway modulators: Research strategies and clinical developments Biochim. Biophys. Acta 2014, 1841, 745-758 (Year: 2014).
Boissy et al. On the pathophysiology of vitiligo: Possible treatment options, Indian J. Dermatol. Venerol. Leprol. 2012, 78, 24-29 (Year: 2012).
Braasch et al., "Novel antisense and peptide nucleic acid strategies for controlling gene expression," Biochemistry, Apr. 9, 2002, 41(14):4503-10.
Breaker et al., "Inventing and improving ribozyme function: rational design versus iterative selection methods," Trends in Biotechnology, Jul. 1, 1994, 12(7):268-75.
Breaker, "Are engineered proteins getting competition from RNA?," Current Opinion in Biotechnology, Aug. 1, 1996, 7(4):442-8.
Brody et al., "High-content affinity-based proteomics: unlocking protein biomarker discovery," Expert Review of Molecular Diagnostics, Nov. 1, 2010, 10(8):1013-22.
Brummelkamp et al., "A system for stable expression of short interfering RNAs in mammalian cells," Science, Apr. 19, 2002, 296(5567):550-3.
CA Office Action in Canadian Appln. No. 3061328, mailed on Jun. 4, 2024, 4 pages.
Cavalié et al., "Maintenance therapy of adult vitiligo with 0.1% tacrolimus ointment: A randomized, double blind, placebo-controlled study," Journal of Investigative Dermatology, Apr. 1, 2015, 135(4):970-4.
Cheuk et al., "CD49a expression defines tissue-resident CD8+ T cells poised for cytotoxic function in human skin," Immunity, Feb. 21, 2017, 46(2):287, 28 pages.
Chiba, "FTY720, a new class of immunomodulator, inhibits lymphocyte egress from secondary lymphoid tissues and thymus by agonistic activity at sphingosine 1-phosphate receptors," Pharmacology & Therapeutics, Dec. 1, 2005, 108(3):308-19.
Christoffersen et al., "Ribozymes as human therapeutic agents," Journal of Medicinal Chemistry, Jun. 1995, 38(12):2023-37.
Clark et al., "Skin effector memory T cells do not recirculate and provide immune protection in alemtuzumab-treated CTCL patients," Science Translational Medicine, Jan. 18, 2012, 4(117):117ra7, 20 pages.
Craiglow et al., "Tofacitinib citrate for the treatment of vitiligo: a pathogenesis-directed therapy," JAMA Dermatology, Oct. 1, 2015, 151(10):1110-2.
Cummings et al., "Antibody-labeled fluorescence imaging of dendritic cell populations in vivo," Journal of Biomedical Optics, Jul. 2008, 13(4):044041.
Damsky et al., "JAK inhibitors in dermatology: the promise of a new drug class," Journal of the American Academy of Dermatology, Apr. 1, 2017, 76(4):736-44.
DeGottardi et al., "Effect of anti-IL-15 administration on T cell and NK cell homeostasis in rhesus macaques," The Journal of Immunology, Aug. 15, 2016, 197(4):1183-98.
Diehl et al., "BEAMing: single-molecule PCR on microparticles in water-in-oil emulsions," Nature Methods, Jul. 2006. 3(7):551-9.

EP European Search Report in European Appln. No. 18792105.1, dated Jan. 27, 2021, 14 pages.
EP Extended European Search Report in European Appln. No. 18792105.1, dated Apr. 28, 2021, 11 pages.
EP Extended Search Report in European Appln. No. 18792105.1, dated May 19, 2021, 11 pages.
EP Office Action in European Appln. No. 18792105.1, mailed on Dec. 8, 2023, 16 pages.
Epron et al., "Monocytes and T cells cooperate to favor normal and follicular lymphoma B-cell growth: role of IL-15 and CD40L signaling," Leukemia, Jan. 2012, 26(1):139-48.
Figueira et al., "Micro RNA s: potential therapeutic targets in diabetic complications of the cardiovascular and renal systems," Acta Physiologica, Jul. 2014, 211(3): 20 pages.
Frenkel et al., "12-dimethylbenz [a] anthracene induces oxidative DNA modification in vivo," Free Radical Biology and Medicine, Sep. 1, 1995, 19(3):373-80.
Gebhardt et al., "Memory T cells in nonlymphoid tissue that provide enhanced local immunity during infection with herpes simplex virus," Nature Immunology, May 2009 May, 10(5):524.
Gilhar et al., "Alopecia areata: animal models illuminate autoimmune pathogenesis and novel immunotherapeutic strategies," Autoimmunity Reviews, Jul. 1, 2016, 15(7):726, 22 pages.
Gilhar et al., "Autoimmune disease induction in a healthy human organ: a humanized mouse model of alopecia areata," Journal of Investigative Dermatology, Mar. 2013, 133(3):844-7.
Grimes, "New insights and new therapies in vitiligo," JAMA, Feb. 9, 2005, 293(6):730-5.
Grunstein et al., "Colony hybridization: a method for the isolation of cloned DNAs that contain a specific gene," Proceedings of the National Academy of Sciences, Oct. 1, 1975, 72(10):3961-5.
Gupta et al., "Modified technique of suction blistering for epidermal grafting in vitiligo," International Journal of Dermatology, Apr. 1999, 38(4):306-9.
Gupta et al., "Suction blister epidermal grafting versus punch skin grafting in recalcitrant and stable vitiligo," Dermatologic Surgery, Dec. 1999, 25(12):955-8.
Hamajima et al., "Intranasal administration of HIV-DNA vaccine formulated with a polymer, carboxymethylcellulose, augments mucosal antibody production and cell-mediated immune response," Clinical immunology and immunopathology, Aug. 1, 1998, 88(2):205-10.
Harris et al., "A mouse model of vitiligo with focused epidermal depigmentation requires IFN-γ for autoreactive CD8+ T-cell accumulation in the skin," Journal of Investigative Dermatology, Jul. 1, 2012, 132(7), 14 pages.
Harris et al., "Rapid skin repigmentation on oral ruxolitinib in a patient with coexistent vitiligo and alopecia areata (AA). Journal of the American Academy of Dermatology," Feb. 1, 2016, 74(2):370-1.
Harris, "Vitiligo and alopecia areata: apples and oranges?," Experimental Dermatology, Dec. 2013, 22(12):785-9.
Hechinger et al., "Therapeutic activity of multiple common γ-chain cytokine inhibition in acute and chronic GVHD," Blood, the Journal of the American Society of Hematology, Jan. 15, 2015, 125(3):570-80.
Jabri et al., "IL-15 functions as a danger signal to regulate tissue-resident T cells and tissue destruction," Nature Reviews Immunology, Dec. 2015, 15(12):771, 27 pages.
Jepsen et al., "Locked nucleic acid: a potent nucleic acid analog in therapeutics and biotechnology," Oligonucleotides, Apr. 1, 2004, 14(2):130-46.
Jiang et al., "Skin infection generates non-migratory memory CD8+ T RM cells providing global skin immunity," Nature, Mar. 2012, 483(7388):227-31.
Joyce et al., "Directed molecular evolution," Scientific American, Dec. 1, 1992, 267(6):90-9.
Joyce, "Amplification, mutation and selection of catalytic RNA," Gene, Oct. 15, 1989, 82(1):83-7.
Kauppinen et al., "Locked nucleic acid (LNA): High affinity targeting of RNA for diagnostics and therapeutics," Drug Discovery Today: Technologies, Sep. 1, 2005, 2(3):287-90.
Kennedy et al., "Reversible defects in natural killer and memory CD8 T cell lineages in interleukin 15-deficient mice," The Journal of Experimental Medicine, Mar. 6, 2000, 191(5):771-80.

(56) References Cited

OTHER PUBLICATIONS

Kim et al., "Automated Heart-Type Fatty Acid-Binding Protein Assay for the Early Diagnosis of Acute Myocardial Infarction," American Journal of Clinical Pathology, Jul. 1, 2010, 134(1):157-62.

Kim et al., "Targeting the IL~15 receptor with an antagonist IL-15 mutant/Fcγ2a protein blocks delayed-type hypersensitivity," The Journal of Immunology, Jun. 15, 1998, 160(12):5742-8.

Kumar et al., "Artificial evolution and natural ribozymes," The FASEB Journal, Sep. 1995, 9(12):1183-95.

Lee et al., "Expression of small interfering RNAs targeted against HIV-1 rev transcripts in human cells," Nature Biotechnology, May 2002, 20(5):500-5.

Levin et al., "Position-dependent effects of locked nucleic acid (LNA) on DNA sequencing and PCR primers," Nucleic Acids Research, Nov. 2006, 34(20), 11 pages.

Liao et al., "Interleukin-2 at the crossroads of effector responses, tolerance, and immunotherapy," Immunity, Jan. 24, 2013, 38(1):13-25.

Liu et al., "Epidermal permeability barrier recovery is delayed in vitiligo-involved sites," Skin Pharmacology and Physiology, Feb. 25, 2010, 23(4):193-200.

Lotti et al., "Vitiligo: new and emerging treatments," Dermatologic Therapy, Mar. 2008, 21(2):110-7.

Mackay et al., "Long-lived epithelial immunity by tissue-resident memory T (TRM) cells in the absence of persisting local antigen presentation," Proceedings of the National Academy of Sciences, May 1, 2012, 109(18):7037-42.

Mackay et al., "T-box transcription factors combine with the cytokines TGF-β and IL-15 to control tissue-resident memory T cell fate," Immunity, Dec. 15, 2015, 43(6):1101-11.

Mackay et al., "The developmental pathway for CD103+ CD8+ tissue-resident memory T cells of skin," Nature Immunology, Dec. 2013, 14(12):1294-301.

Miller, C. A. 2012 'SIP Receptor Agonists', Eds. Levin, J and Laufer, S. Drug Discovery Series, Royal Society of Chemistry vol. 26, 417-443 (Year: 2012).

Miranda et al., "Nucleic acids within urinary exosomes/microvesicles are potential biomarkers for renal disease," Kidney International, Jul. 2, 2010, 78(2):191-9.

Mishra et al., "Molecular pathways: interleukin-15 signaling in health and in cancer," Clinical Cancer Research. Apr. 2014, 20(8):2044-50.

Miyagishi et al., "U6 promoter-driven siRNAs with four uridine 3' overhangs efficiently suppress targeted gene expression in mammalian cells," Nature Biotechnology, May 2002, 20(5):497-500.

Moellmann et al., "Extracellular granular material and degeneration of keratinocytes in the normally pigmented epidermis of patients with vitiligo," Journal of Investigative Dermatology, Nov. 1982, 79(5):321-30.

Murooka et al., "HIV-infected T cells are migratory vehicles for viral dissemination," Nature, Oct. 2012, 490(7419):283-7.

Nelson et al., "IL-2, regulatory T cells, and tolerance," The Journal of Immunology, Apr. 1, 2004, 172(7):3983-8.

Nielsen et al., "Sequence-selective recognition of DNA by strand displacement with a thymine-substituted polyamide," Science, Dec. 6, 1991, 254(5037):1497-500.

Nordström et al., "Direct analysis of single-nucleotide polymorphism on double-stranded DNA by pyrosequencing," Biotechnology and Applied Biochemistry, Apr. 2000, 31(2):107-12.

Orgel, "Selection in vitro," Proceedings of the Royal Society of London, Series B, Biological Sciences, Sep. 21, 1979, 205(1161):435-42.

Paddison et al., "Short hairpin RNAs (shRNAs) induce sequence-specific silencing in mammalian cells," Genes & Development, Apr. 15, 2002, 16(8):948-58.

Park et al. Biomol. Ther. 2017, 25, 80-90 (Year: 2017.

Park et al., "Sphingosine 1-phosphate receptor modulators and drug discovery," Biomolecules & Therapeutics, Jan. 2017, 25(1):80-90.

Paul et al., "Effective expression of small interfering RNA in human cells," Nature Biotechnology, May 2002, 20(5):505-8.

PCT International Preliminary Report on Patentability in International Appln. No. PCT/US2018/029185, dated Nov. 7, 2019, 7 pages.

PCT International Search Report and Written Opinion in Application No. PCT/US2018/29185, dated Aug. 31, 2018.

Pfaffe et al., "Diagnostic potential of saliva: current state and future applications," Clinical Chemistry, May 2011, 57(5):675-87.

Phillips et al., "Rapid point-of-care breath test for biomarkers of breast cancer and abnormal mammograms," PloS one, Mar. 5, 2014, 9(3), 6 pages.

Pinschewer et al., "FTY720 immunosuppression impairs effector T cell peripheral homing without affecting induction, expansion, and memory," The Journal of Immunology, Jun. 1, 2000, 164(11):5761-70.

Ponting et al., "Evolution and functions of long noncoding RNAs," Cell, Feb. 20, 2009, 136(4):629-41.

Rashighi et al., "CXCL10 is critical for the progression and maintenance of depigmentation in a mouse model of vitiligo," Science Translational Medicine, Feb. 12, 2014, 6(223):223ra23.

Rashighi et al., "CXCL10 is critical for the progression and maintenance of depigmentation in a mouse model of vitiligo," Science Translational Medicine, Feb. 12, 2014, 6(223):223ra23-, 12 pages.

Rashighi et al., "Interfering with the IFN-γ/CXCL10 pathway to develop new targeted treatments for vitiligo," Annals of Translational Medicine, Dec. 2015, 3(21), 5 pages.

Regazzetti et al., "Transcriptional analysis of vitiligo skin reveals the alteration of WNT pathway: a promising target for repigmenting vitiligo patients," Journal of Investigative Dermatology Dec. 1, 2015, 135(12):3105-14.

Reinhardt et al., "Cytokine-secreting follicular T cells shape the antibody repertoire," Nature Immunology, Apr. 2009, 10(4), 26 pages.

Roifman, "Human IL-2 receptor a chain deficiency," Pediatric Research, Jul. 2000, 48(1):6-11.

Rork et al., "Understanding autoimmunity of vitiligo and alopecia areata," Current Opinion in Pediatrics, Aug. 2016, 28(4):463, 13 pages.

Rossing et al., "Interstitial fluid: exchange of macromolecules between plasma and skin interstitium," Clinical Physiology, Jun. 1981, (3):275-84.

Rothstein et al., "Treatment of vitiligo with the topical Janus kinase inhibitor ruxolitinib," Journal of the American Academy of Dermatology, Jun. 1, 2017, 76(6):1054-60.

Rotondi et al., "Elevated serum interferon-γ-inducible chemokine-10/CXC chemokine ligand-10 in autoimmune primary adrenal insufficiency and in vitro expression in human adrenal cells primary cultures after stimulation with proinflammatory cytokines," The Journal of Clinical Endocrinology & Metabolism, Apr. 1, 2005, 90(4):2357-63.

Ruchatz et al., "Soluble IL-15 receptor a-chain administration prevents murine collagen-induced arthritis: a role for IL-15 in development of antigen-induced immunopathology," The Journal of Immunology, Jun. 1, 1998, 160(11):5654-60.

Schenkel et al., "Sensing and alarm function of resident memory CD8+ T cells," Nature Immunology, May 2013, 14(5):509.

Skon et al., "Transcriptional downregulation of S1pr1 is required for the establishment of resident memory CD8+ T cells," Nature Immunology, Dec. 2013, 14(12):1285.

Sosa et al., "Confetti-like depigmentation: A potential sign of rapidly progressing vitiligo," Journal of the American Academy of Dermatology, Aug. 1, 2015, 73(2):272-5.

Stenvang et al., "Inhibition of microRNA function by antimiR oligonucleotides," Silence, Dec. 2012, 3(1):1.

Strassner et al., "Suction blistering the lesional skin of vitiligo patients reveals useful biomarkers of disease activity," Journal of the American Academy of Dermatology, May 1, 2017, 76(5):847-55.

Sui et al., "A DNA vector-based RNAi technology to suppress gene expression in mammalian cells," Proceedings of the National Academy of Sciences, Apr. 16, 2002, 99(8):5515-20.

(56) References Cited

OTHER PUBLICATIONS

Szostak et al., "In vitro genetics," Trends in Biochemical Sciences, Mar. 1, 1992, 17(3):89-93.
Taylor et al., "The origin, function, and diagnostic potential of RNA within extracellular vesicles present in human biological fluids," Frontiers in Genetics, Jul. 30, 2013, 4:142.
Ushio et al., "Phenylpyazoleanilides as potent inhibitor of IL-15 dependent T cell proliferation Part 2: Discovery of a new drug candidate, Y-320," Letters in Drug Design & Discovery, Jun. 1, 2008, 5(4):292-6.
Van Den Boorn et al., "Autoimmune destruction of skin melanocytes by perilesional T cells from vitiligo patients," Journal of Investigative Dermatology, Sep. 1, 2009, 129(9):2220-32.
Villadsen et al., "Resolution of psoriasis upon blockade of IL-15 biological activity in a xenograft mouse model," The Journal of Clinical Investigation, Nov. 15, 2003, 112(10):1571-80.
Waldmann et al., "Phase 1 trial of IL-15 trans presentation blockade using humanized Mik-Beta-1 mAb in patients with T-cell large granular lymphocytic leukemia," Blood, the Journal of the American Society of Hematology, Jan. 17, 2013, 121(3):476-84.
Waldmann, "Targeting the interleukin-15/interleukin-15 receptor system in inflammatory autoimmune diseases," Arthritis Research & Therapy, Aug. 2004, 6(4):1-4.
Waldmann, "The biology of interleukin-2 and interleukin-15: implications for cancer therapy and vaccine design," Nature Reviews Immunology, Aug. 2006, 6(8):595-601.
Wang et al., "Increased expression of CXCR3 and its ligands in vitiligo patients and its role as potential clinical markers for vitiligo," Journal of Dermatological Science, Oct. 1, 2016, 84(1):1318-26.
Watanabe et al., "Human skin is protected by four functionally and phenotypically discrete populations of resident and recirculating memory T cells," Science Translational Medicine, Mar. 18, 2015, 7(279):279ra39, 14 pages.
Wilson et al., "Small-molecule inhibitors of IL-2/IL-2R: lessons learned and applied," Small-Molecule Inhibitors of Protein-Protein Interactions, Aug. 12, 2010, 25-59.
Xing et al., "Alopecia areata is driven by cytotoxic T lymphocytes and is reversed by JAK inhibition," Nature Medicine, Sep. 2014, 20(9):1043-9.
Yaghoobi et al., "Vitiligo: a review of the published work," The Journal of dermatology, May 2011, 38(5):419-31.
Yang et al., "Detection of tumor cell-specific mRNA and protein in exosome-like microvesicles from blood and saliva," PloS one, 2014;9(11), 10 pages.
Yasun et al., "Enrichment and detection of rare proteins with aptamer-conjugated gold nanorods," Analytical Chemistry, Jul. 17, 2012, 84(14):6008-15.
Yu et al., "RNA interference by expression of short-interfering RNAs and hairpin RNAs in mammalian cells," Proceedings of the National Academy of Sciences, Apr. 30, 2002, 99(9):6047-52.
Zhang et al., "Potent and selective stimulation of memory-phenotype CD8+ T cells in vivo by IL-15," Immunity, May 1, 1998, 8(5):591-9.
Zhang et al., "PowerBlast: a new network Blast application for interactive or automated sequence analysis and annotation," Genome Research, Jun. 1, 1997, 7(6):649-56.
Zhu et al., "Immune surveillance by CD8αα+ skin-resident T cells in human herpes virus infection," Nature, May 2013, 497(7450):494-7.
Communication pursuant to Rule 114(2) EPC in European Appln. No. 18792105.1, mailed on Jan. 15, 2025, 11 pages.
Richmond et al., "Vitiligo is maintained by antigen-specific resident memory t cells, which can be targeted to create a durable treatment response," Journal of Investigative Dermatology, Apr. 12, 2017, 137(5) Suppl. 1:S8 (Abstract only).
wikipedia.org [online], "Interleukin 15," Jan. 18, 2017, retrieved on Jan. 27, 2025, retrieved from URL <https://en.wikipedia.org/w/index.php?title=Interleukin_15&oldid=760734022>, 13 pages.

Local Durability Study

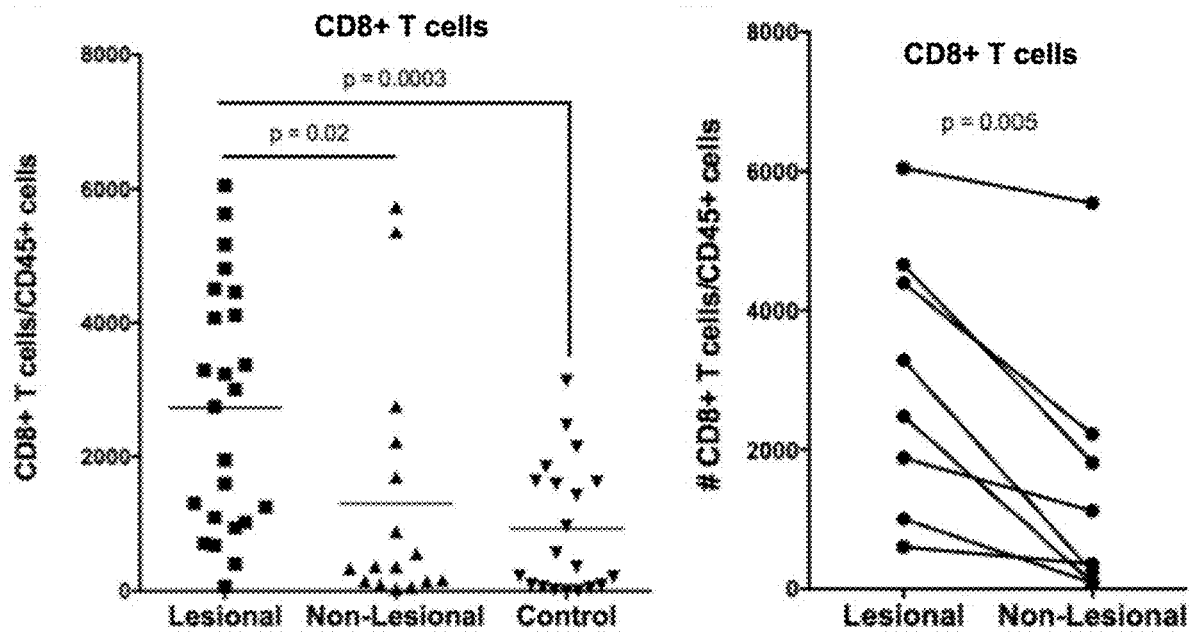
FIG. 10A
FIG. 10B
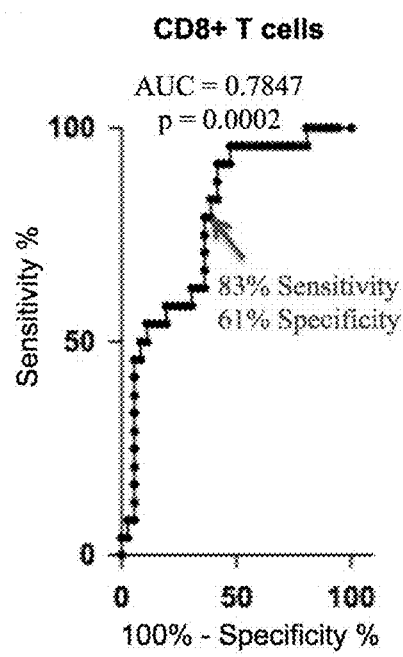
FIG. 10C

DIAGNOSIS AND TREATMENT OF VITILIGO

CROSS-REFERENCE TO RELATED APPLICATIONS

This application is a continuation of U.S. application Ser. No. 18/607,636, filed Mar. 18, 2024, which is a continuation of U.S. application Ser. No. 18/234,923, filed Aug. 17, 2023, which is a continuation of U.S. application Ser. No. 17/667,699, filed Feb. 9, 2022, which is a divisional application of U.S. Application Ser. No. 16/608,116, filed on Oct. 24, 2019, now U.S. Pat. No. 11,278,505, which is a 371 of International Application No. PCT/US2018/029185, filed on Apr. 24, 2018, which claims the benefit of U.S. Provisional Application Ser. No. 62/489,191, filed on Apr. 24, 2017. The entire contents of the foregoing are hereby incorporated by reference.

STATEMENT OF FEDERALLY SPONSORED RESEARCH

This invention was made with Government support under Grant Nos. AR061437 and AR069114 awarded by the National Institutes of Health. The Government has certain rights in the invention.

TECHNICAL FIELD

Described herein are methods of diagnosing and treating vitiligo.

BACKGROUND

Vitiligo is caused by CD8+ T cells that target melanocytes for destruction (van den Boorn et al., 2009), resulting in patchy depigmentation that is disfiguring and distressing to patients (Alikhan et al., 2011) Depigmentation typically recurs rapidly at the same location after therapy is stopped (Cavalie et al., 2015), indicating that autoimmune memory persists in the skin and permits disease reactivation after cessation of treatment. It affects approximately 1% of the population worldwide, yet there are currently no FDA approved treatments.

SUMMARY

Skin lesions in vitiligo are maintained over time, resisting conventional treatments by returning after they are discontinued. Tissue resident memory T cells (Trm) provide rapid, localized protection against reinfection from skin and mucosal-tropic viruses. A similar memory response is observed in autoimmune diseases as rapid relapse occurs at sites of improvement after discontinuing therapy. As shown herein, antigen-specific Trm are present in both mouse and human vitiligo skin lesions, an autoimmune disease mediated by CD8+ T cells that kill melanocytes and create white spots. Functional analysis of Trm cells indicated that they sense autoantigen in the skin and secrete alarm signals to recruit recirculating T cells to kill melanocytes. In addition, Trm are not sufficient for autoimmunity: treatment with the Sphingosine-1-phosphate 1 (S1P1) inhibitor FTY720 (fingolimod) resulted in rapid repigmentation, yet preserved Trm in the skin while preventing recirculating memory T cell recruitment. However, treatment with an IL-15Rβ blocking antibody effectively depleted autoreactive Trm, inhibited their function, and resulted in durable reversal of disease in mice. Based on these data and clinical observations, depleting Trm or inhibiting their function is a highly effective and durable treatment for vitiligo and other autoimmune diseases.

Thus, provided herein are methods for treating a subject who has a vitiligo lesion. The methods include identifying a subject in need of treatment; and administering a therapeutically effective amount of an inhibitor of Sphingosine-1-phosphate receptor 1 (SIP1), Interleukin 15 (IL-15) or the IL-15 receptor to the lesion, and the use of inhibitors of SIP1, IL-15 or the IL-15 receptor to treat vitiligo. In some embodiments, the inhibitor is a small molecule inhibitor, an antibody, a peptide inhibitor, or an inhibitory nucleic acid targeting SIP1, IL-15 or the IL-15 receptor.

In some embodiments, the inhibitor is administered to the epidermis within the lesion, e.g., by subcutaneous or intradermal administration, or a microneedle array.

In some embodiments, the inhibitor is administered systemically, e.g., orally or parenterally.

Also provided herein are devices for the delivery of SIP1 or IL-15 inhibitor to a subject with vitiligo, e.g., a microneedle array comprising an inhibitor of SIP1, IL-15 or the IL-15 receptor.

Further, provided herein are methods for determining a score for a subject who has vitiligo. The methods include obtaining a sample comprising lesional interstitial skin fluid and epidermis from a subject; evaluating CD8+ T cell infiltrate, e.g., by flow cytometry, and elevated chemokine protein, e.g., by ELISA, in lesional fluid, and levels of a panel of 20 genes (shown in Table A) in the lesional skin; and using the levels to calculate a score.

In some embodiments, the methods include comparing the score to a reference score, and selecting a subject who has a score above the reference score. In some embodiments, the reference score is a control reference score that represents a normal score in an unaffected subject, or a disease reference that represents a score in a subject with active IFN-γ-induced inflammation.

In some embodiments, the methods include selecting and optionally administering to the subject a treatment for vitiligo, e.g., a treatment that includes administering a therapeutically effective amount of an inhibitor of SIP1, IL-15 or the IL-15 receptor to a vitiligo lesion. In some embodiments, the treatment includes one or more of topical or systemic treatment with a corticosteroid, topical treatment with an immunomodulatory agent, topical treatment with calcipotriol, dexamethasone, phototherapy, or targeted laser therapy.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 10A-10C. Blister fluid CD8+ T cells are elevated in lesional skin. Blister fluid from lesional, non-lesional, and healthy control skin was analyzed by flow cytometry for CD8+ T cells and normalized to CD45+ cells. (A) Normalized CD8+ T cells from multiple blisters in 8 patients and 7 controls. (B) Paired analysis in lesional vs. non-lesional skin. (C) ROC curve comparing normalized CD8+ T cells in lesional to non-lesional blisters and healthy controls, which reveals decent sensitivity and specificity of this assay to detect active lesional skin FIGS. 11A-11C. Blister fluid CXCL9 elevated in lesional skin. Blister fluid from lesional, non-lesional, and healthy control skin was analyzed by ELISA for CXCL9. (ACXCL9 from multiple blisters in 7 patients and 6 controls. (B) Paired analysis of CXCL9 average concentrations in lesional vs. non-lesional skin. (C) ROC curve comparing lesional blisters to non-lesional and healthy control blisters, which reveals good sensitivity and specificity of this assay to detect active lesional skin.

DETAILED DESCRIPTION

Figure 1A:
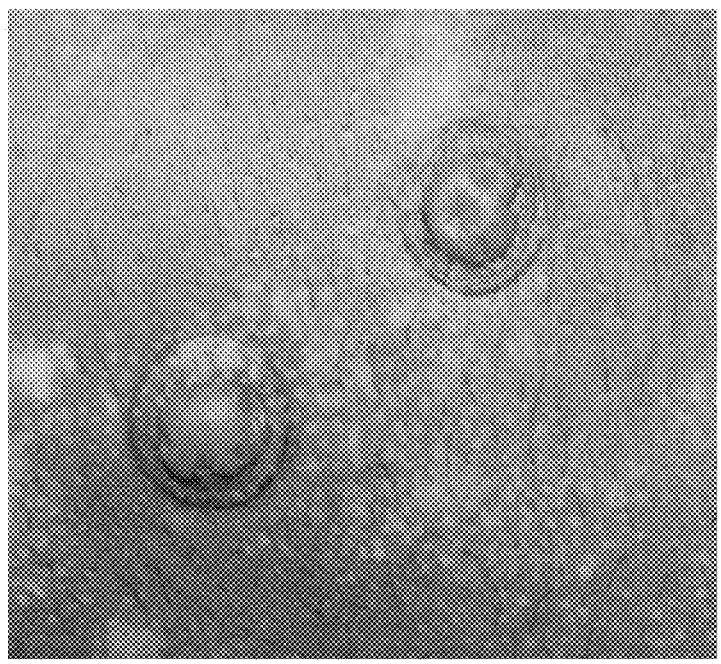
FIGS. 1A-1F. Melanocyte-specific CD8+ Trm cells are present in vitiligo patient skin and express the CD122 chain of the IL-15 receptor, whereas keratinocytes express the CD215 chain. (A) Sample photo of a vitiligo skin blister biopsy. (B) Flow cytometry staining of blister fluid in a vitiligo patient pregated on live single CD45+CD8+ T cells. MART-1, gp100, and tyrosinase pentamers were pooled to identify melanocyte antigen reactive cells, and Trm phenotype markers were assessed using CD69 and CD103 antibodies. (C) Quantification of the frequency of melanocyte-specific cells with a Trm phenotype in PBMCs, lesional, and nonlesional skin. Melanocyte-specific Trm were significantly enriched in lesional skin. (Each symbol represents one patient; open squares were stained with MART-1 pentamer alone, closed circles were stained with all three pentamers MART-1, gp100, and tyrosinase; one-way ANOVA with Tukey's post tests significant as indicated). (D) Flow cytometry staining of CD122 on melanocyte-specific Trm, and quantification in lesional and nonlesional skin. Cells were pregated on live single CD45+CD8+pentamer+ T cells. There was no significant difference in CD122 expression on melanocyte-specific Trm in lesional versus nonlesional skin. (E) Flow cytometry staining of CD215 on keratinocytes from blister roofs, and quantification in lesional and nonlesional skin. Cells were pregated on live single CD45− cells. CD215 expression was higher in lesional than nonlesional skin (Student's t tests significant as indicated). (F) Only 1 patient's T cells were found to express CD215.

Immune memory is mediated by long-lived, antigen-experienced lymphocytes that protect against reinfection. Recent studies have defined CD8+ resident memory T cells (Trm) that remain in non-lymphoid tissues to provide tissue surveillance against pathogens (Gebhardt et al., 2009; Zhu et al., 2013). These Trm are phenotypically distinct from other memory T cell populations in that they express specific developmental markers that bolster their function (Mackay et al., 2013; Skon et al., 2013). Upon entering tissues such as the mucosa and skin epidermis, differentiating Trm upregulate CD69 and CD103, downregulate the chemokine receptors SIP1 and CCR7 to prevent recirculation, and set up residence. Most studies have focused on anti-viral Trm responses, with the goal of enhancing their function for vaccine development. Two key questions that remain are: (1) what roles do Trm play in autoimmunity? and (2) can Trm responses be targeted as a strategy to treat autoimmunity?

To answer these questions, the present inventors sought to define autoreactive Trm using vitiligo as a model autoimmune disease because of its dependence on CD8+ T cells, known autoantigens, and accessibility of target tissue. As shown herein, lesional skin biopsies from patients contained antigen-specific CD8+ Trm, supporting a role for these cells in human vitiligo.

A mouse model of vitiligo was developed through the adoptive transfer of TCR transgenic T cells recognizing the human melanocyte antigen pre-melanosome protein (Harris et al., 2012). These T cells, called PMEL, target mouse melanocytes and induce patchy epidermal depigmentation that mirrors human disease (Rashighi et al., 2014). Using this model, autoreactive Trm within the skin were characterized and their role in disease determined. The present data indicate that once established, melanocyte-specific Trm remain activated in skin in the absence of inflammation, and serve an alarm/recruit function to attract recirculating memory T cells capable of killing the target cells.

The role of Trm has been reported to vary in the context of different skin and mucosal viral infections. In one study, Trm alone were able to provide rapid immunity to reinfection with vaccinia virus (Jiang et al., 2012) while others have shown that Trm send out an alarm signal to recruit recirculating memory T cells, which provided the key effector functions against herpes virus (Schenkel et al., 2013) and other viruses (Ariotti, 2014). Another study demonstrated that the recirculating memory T cells alone are unable to provide efficient responses to reinfection with herpes (Mackay et al., 2012), indicating that a complex interplay between Trm and recirculating memory T cells is extant. Cooperation of Trm with other recruited T cell populations has also been indicated in cutaneous T cell lymphomas (Watanabe, 2015). The present data support the role of autoreactive Trm as sentinel/alarm cells that work together with recirculating memory cell populations to maintain depigmentation during vitiligo.

IL-15Rβ is a shared receptor for both IL-2 and IL-15, and so a role for IL-2 in the maintenance of Trm is possible. However, others have shown that IL-15 is much more potent at generating CD8+ Trm pools than residual IL-2 signaling in skin tissue (Adachi et al., 2015), and IL-15 is required for the generation of CD8+ Trm in viral models in mice (Mackay et al., 2013). Further, CD8+ T cells often express IL-15Rβ without CD25 (Zhang et al., 1998). Mice lacking IL-2 or CD25 develop autoimmunity, whereas mice lacking IL-15 are protected from autoimmunity (reviewed in ((Nelson, 2004))). Another recent study found that IL-15Rβ antibody administration in rhesus macaques greatly reduced tissue effector memory T cell populations, while recirculating populations bounced back (DeGottardi et al., 2016). As shown herein, targeting IL-15 signaling through antibody treatment even after the generation of Trm in the tissue was effective at clearing these cells from the epidermis, indicating that IL-15 signaling is required for maintenance of these cells.

The present data support targeting this cytokine as a strategy to clear autoreactive memory cells from the tissue, resulting in a long-lasting, durable response to treatment. This is in contrast to existing therapies for inflammation in skin and other tissues, which result in rapid relapse after they are discontinued. Further, targeting IL-15 preferentially affects autoreactive T cells while leaving most endogenous T cell populations intact.

Methods of Treatment

The methods described herein include methods for the treatment of disorders associated with T cell-mediated autoimmunity. In some embodiments, the disorder is vitiligo. Vitiligo is a chronic, progressive autoimmune skin disease characterized by white or depigmented patches of skin, most commonly on the hands, forearms, feet and face. Depigmentation results from destruction of melanocytes by T cells. This disease affects 1% of the world population and can cause psychological distress to affected patients. There are several clinical presentations of active disease, including: trichrome vitiligo, inflammatory vitiligo, confetti vitiligo, and others; Koebner phenomenon is the development of vitiligo at the site of trauma to the skin. Vitiligo can be further classified as localized, generalized, or universal, depending on the distribution and extent of depigmentation (Yaghoobi et al., 2011). Diagnosis is typically made based on clinical findings, occasionally aided by histological findings from skin biopsies at the sites of lesions, including abnormalities in keratinocytes, melanocytes, and Langerhans cells; epidermal vacuolization; and thickening of the basement membrane (Moellmann et al., 1982). Alternatively a diagnosis can be made, and/or a subject selected, using the Vitiligo Disease Activity Score (VDAS), Vitiligo Area Scoring Index (VASI), or the Vitiligo European Task Force (VETF) assessment. The VDAS is estimated by asking the patient when they last saw a new vitiligo lesion appear, within the last 6 weeks (4 points), 6-12 weeks (3 points), 3-6 months (2 points), 6-12 months (1 point), stable for over 1 year (0 points), or repigmenting (−1 point) (Bhatnagar et al., 2007). In some embodiments, the subject can be one who has trichrome (3-color) or confetti-like (multiple 1-2 mm macules) appearance of depigmented macules in vitiligo lesions, or who has a VDAS score of 2-4.

There is no known cure for vitiligo, but a variety of medical and surgical interventions are available to improve the appearance of the lesions. Medical interventions include topical or systemic treatment with corticosteroids such as prednisone or clobetasol, topical treatment with immunomodulatory agents such as tacrolimus, topical treatment with the vitamin D3 analog calcipotriol, pulse-dose therapy with dexamethasone (e.g., 4 mg), phototherapy with UV light (nbUVB), targeted laser therapy on stable patches of localized vitiligo, tattooing the depigmented skin, and depigmentation of unaffected skin in cases where vitiligo is widespread and repigmentation therapy is ineffective (Grimes, 2005) (Lotti et al., 2008). Surgical interventions include suction-blister grafts, punch grafts, autologous melanocyte cultures, cultured epidermal suspensions, noncultured epidermal suspensions, epidermal blister grafts, and split thickness grafts (Grimes, 2005).

In some embodiments, the disorder to be treated is another autoimmune disease, such as lupus, psoriasis, alopecia areata, lichen planus, scleroderma, graft vs host disease, diabetes, autoimmune thyroid disease, multiple sclerosis, or autoimmune uveitis.

Generally, the methods include systemic or (more preferably) local delivery of a therapeutically effective amount of an inhibitor of IL-15, the IL-15 receptor, a Spingosine-1-receptor inhibitor, and/or the downstream signaling molecules JAK1 and 3 as described herein, to a subject who is in need of, or who has been determined to be in need of, such treatment. As used in this context, to "treat" means to ameliorate at least one symptom of the disorder associated with autoimmunity. Vitiligo is characterized by depigmentation of the skin; thus, a treatment can result in a reduction in appearance of lesions and a return or approach to normal pigmentation. Administration of a therapeutically effective amount of a compound described herein for the treatment of vitiligo will result in decreased depigmentation.

Inhibitors of IL-15 and the IL-15 Receptor

The methods and compositions described herein can include the use of inhibitors of IL-15 and the IL-15 receptor. In some embodiments, the therapeutic molecule to be administered comprises a small molecule inhibitor of the IL-15 receptor alpha chain, e.g., benzoic acid derivatives as described in WO2014191822 A1 and amine derivatives as described in WO2014191823 A1. In some embodiments, the therapeutic molecule to be administered comprises a small molecule inhibitor of IL-15-induced cellular responses, e.g., cefazolin as described in US20160235762 A1 and Y-320 (Ushio, 2008). In some embodiments, the therapeutic molecule to be administered comprises a soluble IL-15 receptor alpha chain which binds IL-15 and antagonizes the IL-15 receptor (Ruchatz et al., 1998). In some embodiments, the therapeutic molecule to be administered comprises an antagonistic mutant IL-15/Fc-gamma 2a fusion protein which competitively inhibits binding of IL-15 to the IL-15 receptor (Kim et al., 1998). In some embodiments, the therapeutic molecule to be administered comprises a peptide that binds the IL-15 receptor alpha chain and inhibits IL-15 activity, as described in U.S. Pat. No. 7,736,638 B2. In some embodiments, the therapeutic molecule to be administered comprises an antibody which specifically binds the IL-2/IL-15 receptor beta subunit, e.g. HuABC2 or HuABC101, as described in U.S. Pat. No. 9,028,830B2. A number of inhibitors of CD122 (also known as IL-2Rβ and p75) are known in the art, including antibodies (see, e.g., U.S. Pat. No. 9,028,830) and small molecules (e.g., Ro26-4550, SP4206, ABT-737, Nutlin-2, and Compound 3; see, e.g., Wilson and Arkin, Curr Top Microbiol Immunol. 2011; 348:25-59; Laio et al., Immunity. 2013 Jan. 24; 38 (1): 13-25. In some embodiments, the therapeutic molecule to be administered comprises an antibody that specifically binds the IL-2/IL-15 receptor gamma subunit (Hechinger et al., 2015). In some embodiments, the therapeutic molecule to be administered comprises an antibody that specifically binds the IL-15 receptor alpha subunit (Epron et al., 2012). In some embodiments, the therapeutic molecule to be administered comprises an antibody that specifically binds IL-15, e.g., as described in WO03017935.

Inhibitors of Jak1 and Jak3

The methods and compositions described herein can include inhibitors of Jak1 and Jak3. In some embodiments, the therapeutic molecule to be administered comprises a small molecule inhibitor of Jak1 and/or Jak3, for example Tofacitinib, Ruxolitinib, Perficitinib, Baricitinib, Decernotinib, R348, AT9283, Oclacitinib, Momelotinib, WHI-P154, ZM 39923 HCl, Filgotinib, Cerdulatinib, or Upadacitinib. In some embodiments, the therapeutic molecule to be administered comprises an antibody that binds Jak1 and/or Jak3. (Craiglow and King, 2015; Harris et al., 2016) (Damsky and King, 2017).

Inhibitors of SIP1

Sphingosine-1-phosphate receptor inhibitors are immunomodulators that include Myriocin, Fingolimod, Ozanimod, Ponesimod, and Laquinimod. See Park et al., Biomolecules & Therapeutics. 25 (1): 80-90.

Inhibitory Nucleic Acids Targeting IL-15, IL-15 Receptor Subunits, Jak1 or Jak3

The methods and compositions described herein can include nucleic acids that target (specifically binds, or are complementary to) SIP1, IL-15, IL-15 receptor alpha subunit, IL-15 receptor beta subunit (CD122), IL-15 gamma subunit, Jak1, or Jak3 mRNAs. Inhibitory nucleic acids useful in the present methods and compositions include antisense oligonucleotides, small interfering RNA (siRNA), small hairpin RNA (shRNA), molecules comprising modified bases, locked nucleic acid molecules (LNA molecules), peptide nucleic acid molecules (PNA molecules), and other oligomeric compounds or oligonucleotide mimetics that hybridize to at least a portion of the target nucleic acid and inhibit its function.

In some embodiments, the inhibitory nucleic acids are 7 to 50, 7 to 20, 7 to 25, 10 or 13 to 50, or 10 or 13 to 30 nucleotides (nts) in length, or as short as 7 or 8 up to the entire length of the target sequence (e.g., 7 to 22, 7 to 77, or 7 to 84 nts for SEQ ID NOs. 1, 2, and 3 respectively). One having ordinary skill in the art will appreciate that this embodies inhibitory nucleic acids having complementary portions of 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the target sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30 60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., 1990; Zhang and Madden, 1997), e.g., using the default parameters.

Once one or more target regions, segments or sites have been identified, e.g., within a sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides that can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of an RNA molecule, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 g/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described (Benton and Davis, 1977; Grunstein and Hogness, 1975), (Ausubel et al. Current Protocols in Molecular Biology, Wiley Interscience, New York, 2001); (Berger and Kimmel, Guide to Molecular Cloning Techniques, 1987, Academic Press, New York; and Sambrook et al., Molecular Cloning: A Laboratory Manual, Cold Spring Harbor Laboratory Press, New York).

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., 1990; Zhang and Madden, 1997). Inhibitory nucleic acids that hybridize to an RNA can be identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids), as well as WO2012/065143, WO2012/087983, and WO2014/025887 (inhibitory nucleic acids targeting non-coding RNAs/supRNAss), all of which are incorporated herein by reference in their entirety.

siRNA/shRNA

In some embodiments, the nucleic acid sequence that is complementary to a target RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology (Brummelkamp et al., 2002; Lee et al., 2002; Miyagishi and Taira, 2002; Paddison et al., 2002; Paul et al., 2002; Sui et al., 2002; Yu et al., 2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Christoffersen and Marr, 1995) (Usman & McSwiggen, 1995 Ann. Rep. Med. Chem. 30, 285-294). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979) have been used to evolve new nucleic acid catalysts capable of catalyzing a variety of reactions, such as cleavage and ligation of phosphodiester linkages and amide linkages (Bartel and Szostak, 1993; Beaudry and Joyce, 1992; Breaker, 1996; Breaker and Joyce, 1994; Joyce, 1989, 1992; Kumar and Ellington, 1995; Szostak, 1992). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 rnM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference. In some embodiments, the modifications are 2' sugar modifications including 2'-O-methyl ribose-modified RNA (2'-OMe), 2'-O-methoxyethyl (2'-MOE), 2'-fluoro (2'-F) and LNA modifications (Bernardo et al., 2015).

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the inhibitory nucleic acid into which they are incorporated more resistant to nuclease digestion than the native oligodeoxynucleotide; these modified oligos survive intact for a longer time than unmodified inhibitory nucleic acids. Specific examples of modified inhibitory nucleic acids include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are inhibitory nucleic acids with phosphorothioate backbones and those with heteroatom backbones, particularly CH2-NH—O—CH2, CH, ~N(CH3)~O~CH2 (known as a methylene(methylimino) or MMI backbone], CH2-O—N(CH3)-CH2, CH2N—(CH3)-N(CH3)-CH2 and O—N(CH3)-CH2-CH2 backbones, wherein the native phosphodiester backbone is represented as O—P—O—CH); amide backbones (see De Mesmacker et al. Ace. Chem. Res. 1995, 28:366-374); morpholino backbone structures (see Summerton and Weller, U.S. Pat. No. 5,034,506); peptide nucleic acid (PNA) backbone (i.e., peptide bonds, wherein the phosphodiester backbone of the inhibitory nucleic acid is replaced with a polyamide backbone, the nucleotides being bound directly or indirectly to the aza nitrogen atoms of the polyamide backbone (Nielsen, 1991). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in (Braasch and Corey, 2002) (Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991).

Cyclohexenyl nucleic acid inhibitory nucleic acid mimetics are described in Wang et al., J. Am. Chem. Soc., 2000, 122, 8595-8602.

Modified inhibitory nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315;

5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH3, F, OCN, OCH3 OCH3, OCH3 O(CH2)n CH3, O(CH2) n NH2 or O(CH2) n CH3 where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an inhibitory nucleic acid; or a group for improving the pharmacodynamic properties of an inhibitory nucleic acid and other substituents having similar properties. A preferred modification includes 2'-methoxyethoxy [2'-0-CH2CH2OCH3, also known as 2'-O-(2-methoxyethyl)] (Martin et al, Helv. Chim. Acta, 1995, 78, 486). Other preferred modifications include 2'-methoxy (2'-0-CH3), 2'-propoxy (2'-OCH2 CH2CH3) and 2'-fluoro (2'-F). Similar modifications may also be made at other positions on the inhibitory nucleic acid, particularly the 3' position of the sugar on the 3' terminal nucleotide and the 5' position of 5' terminal nucleotide. Inhibitory nucleic acids may also have sugar mimetics such as cyclobutyls in place of the pentofuranosyl group.

Alternatively or in addition, the modification can be inclusion of N,N-diethyl-4-(4-nitronaphthalene-1-ylazo)-phenylamine ('ZEN'), which when placed near the ends of a 2'-OMe modified oligonucleotide (ZEN-AMO) increased binding affinity and blocked exonuclease degradation as compared to unmodified 2'-OMe oligonucleotides (Lennox et al., Mol. Ther. Nucleic Acids 2, e117 (2013)).

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino) adenine, 2-(imidazolylalkyl) adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given inhibitory nucleic acid to be uniformly modified, and in fact more than one of the aforementioned modifications may be incorporated in a single inhibitory nucleic acid or even at within a single nucleoside within an inhibitory nucleic acid.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an inhibitory nucleic acid mimetic that has been shown to have excellent hybridization properties, is referred to as a peptide nucleic acid (PNA). In PNA compounds, the sugar-backbone of an inhibitory nucleic acid is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ca., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the inhibitory nucleic acid. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. Sec, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids (including ASOs) used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxygen and the 4'-carbon—i.e., inhibitory nucleic acids containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., 2004). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See (Levin et al., 2006), (You et al., Nuc. Acids. Res. 34: e60 (2006); McTigue et al., Biochemistry 43: 5388-405 (2004). For example, "gene walk" methods, similar to those used to design antisense oligos, can be used to optimize the inhibitory activity of the LNA; for example, a series of inhibitory nucleic acids of 10-30 nucleotides spanning the length of a target RNA can be prepared, followed by testing for activity. Optionally, gaps, e.g., of 5-10 nucleotides or more, can be left between the LNAs to reduce the number of inhibitory nucleic acids synthesized and tested. GC content is preferably between about 30 60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) inhibitory nucleic acids). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; (Jepsen et al., 2004; Kauppinen et al., 2005; Ponting et al., 2009) Koshkin et al. Tetrahedron 54, 3607-3630 (1998); Obika et al. Tetrahedron Lett. 39, 5401-5404 (1998), and references cited therein.

See also (Baigude and Rana, 2014; Bernardo et al., 2015; Figueira et al., 2014; Stenvang et al., 2012).

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques (Frenkel et al., 1995) Adams (1983) J. Am. Chem. Soc. 105:661; Belousov (1997) Nucleic Acids Res. 25: 3440-3444; Blommers (1994) Biochemistry 33: 7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (Kauppinen et al., 2005) Koshkin et al., J. Am. Chem. Soc., 120(50):13252-13253 (1998)). For additional modifications see US20100004320, US20090298916, and US20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Pharmaceutical Compositions and Methods of Administration

The methods described herein include the use of pharmaceutical compositions comprising inhibitors of SIP1, IL-15, the IL-15 receptor, or Jak1/3.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., bioactive molecules that promote melanocyte regeneration, growth, or migration, such as α-MSH analogs (afamelanotide, etc), WNT agonists, piperine or its analogs, or surgical transplantation of melanocytes.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, compositions comprising an IL-15, IL-15 receptor, or Jak1/3 inhibitor for transdermal application can further comprise cosmetically-acceptable carriers or vehicles and any optional components. A number of such cosmetically acceptable carriers, vehicles and optional components are known in the art and include carriers and vehicles suitable for application to skin (e.g., sunscreens, creams, milks, lotions, masks, serums, etc.), see, e.g., U.S. Pat. Nos. 6,645,512 and 6,641,824. In particular, optional components that may be desirable include, but are not limited to absorbents, anti-acne actives, anti-caking agents, anti-cellulite agents, anti-foaming agents, anti-fungal actives, anti-inflammatory actives, anti-microbial actives, anti-oxidants, antiperspirant/deodorant actives, anti-skin atrophy actives, anti-viral agents, anti-wrinkle actives, artificial tanning agents and accelerators, astringents, barrier repair agents, binders, buffering agents, bulking agents, chelating agents, colorants, dyes, enzymes, essential oils, film formers, flavors, fragrances, humectants, hydrocolloids, light diffusers, nail enamels, opacifying agents, optical brighteners, optical modifiers, particulates, perfumes, pH adjusters, sequestering agents, skin conditioners/moisturizers, skin feel modifiers, skin protectants, skin sensates, skin treating agents, skin exfoliating agents, skin lightening agents, skin soothing and/or healing agents, skin thickeners, sunscreen actives, topical anesthetics, vitamin compounds, and combinations thereof.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194, 389, and the mammalian transdermal needle-free vaccination with powder-form vaccine as disclosed in U.S. Pat. No. 6,168,587. Additionally, intranasal delivery is possible (Hamajima et al., 1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

In some embodiments, the therapeutic agents are administered by a microneedle array, e.g. as described in U.S. Pat.

No. 6,379,324B1, U.S. Pat. No. 6,881,203B2, U.S. Pat. No. 6,256,533B1, U.S. Pat. No. 6,790,372B2, and U.S. Pat. No. 3,964,482A. These arrays comprise a number of either hollow or solid microneedles which are used to pierce through the stratum corneum, the outermost layer of skin comprising dead skin cells, to facilitate transdermal drug delivery. Penetration of drugs delivered locally by this method is improved as compared to topical delivery, is painless, and causes minimal trauma to the skin. Drugs can be delivered by passive diffusion, injection, or iontophoresis.

The pharmaceutical compositions can be included in a container, pack, or dispenser together with instructions for administration.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Methods of Diagnosis

Included herein are methods for diagnosing vitiligo. The methods rely on determining a vitiligo score using VDAS, VASI and/or VETF. Biomarkers CXCL9, CXCL10 and CD8+ T cells may also be assessed using a minimally invasive, non-scarring skin biopsy technique to reliably and accurately sample vitiligo lesions by inducing suction blisters, which provide both fluid (interstitial skin fluid) and roof (epidermis) for analysis, or tape-stripping the outer layer of the skin for analysis (Strassner et al., 2017). The methods include obtaining a sample comprising lesional interstitial skin fluid and a sample comprising epidermis from the lesion from a subject, and evaluating CD8+ T cell infiltrate, e.g., by flow cytometry, and elevated chemokine protein, e.g., by ELISA, in lesional fluid, and levels of a panel of 20 genes (shown in Table A) in the lesional skin.

A negative pressure instrument was used to create suction blisters, a process that induced minimal discomfort and does not leave a permanent scar (Babu et al., 2008; Gupta et al., 1999a; Gupta et al., 1999b). The blister fluid, comprised of interstitial fluid from the epidermis and superficial dermis where active inflammation is located (Rossing and Worm, 1981), is drawn from a broad area of the skin, providing an opportunity to sample much more of the lesion than a conventional biopsy. We found that blister fluid from lesional skin contains significantly elevated numbers of CD8+ T cells and CXCL9 protein compared to non-lesional and healthy control skin (Strassner et al., 2017). The expression of a small panel of genes involved in CD8+ T cell activity, IFN-γ signaling, and melanocyte activity mark active vitiligo lesions compared to healthy skin (Rashighi et al., 2014). Our unpublished studies reveal that much of this activity is located in the epidermis, and thus analyzing epidermal blister roofs may be an effective, innovative way to monitor disease activity through gene expression. Another option is through tape-stripping the epidermis and analyzing gene expression on the cells removed in this way (Liu et al., 2010). An innovative combined analysis of the blister fluid and roof will be more sensitive and specific than any single measure alone, and could become the standard tool to measure IFN-γ-specific disease activity and treatment responses in future clinical studies.

Various methods are well known within the art for the identification and/or isolation and/or purification of a biological marker (e.g., cell, protein or nucleic acid) from a sample. An "isolated" or "purified" biological marker is substantially free of cellular material or other contaminants from the cell or tissue source from which the biological marker is derived i.e. partially or completely altered or removed from the natural state through human intervention. For example, nucleic acids contained in the sample are first isolated according to standard methods, for example using lytic enzymes, chemical solutions, or isolated by nucleic acid-binding resins following the manufacturer's instructions.

The presence and/or level of a protein can be evaluated using methods known in the art, e.g., using standard electrophoretic and quantitative immunoassay methods for proteins, including but not limited to, Western blot; enzyme linked immunosorbent assay (ELISA); biotin/avidin type assays; protein array detection; radio-immunoassay; immunohistochemistry (IHC); immune-precipitation assay; FACS (fluorescent activated cell sorting); mass spectrometry (Brody et al., 2010; Kim et al., 2010; Pfaffe et al., 2011; Phillips et al., 2014; Yasun et al., 2012). The methods typically include revealing labels such as fluorescent, chemiluminescent, radioactive, and enzymatic or dye molecules that provide a signal either directly or indirectly. As used herein, the term "label" refers to the coupling (i.e. physically linkage) of a detectable substance, such as a radioactive agent or fluorophore (e.g. phycoerythrin (PE) or indocyanine (Cy5), to an antibody or probe, as well as indirect labeling of the probe or antibody (e.g. horseradish peroxidase, HRP) by reactivity with a detectable substance.

In some embodiments, an ELISA method may be used, wherein the wells of a mictrotiter plate are coated with an antibody against which the protein is to be tested. The sample containing or suspected of containing the biological marker is then applied to the wells. After a sufficient amount of time, during which antibody-antigen complexes would have formed, the plate is washed to remove any unbound moieties, and a detectably labelled molecule is added. Again, after a sufficient period of incubation, the plate is washed to remove any excess, unbound molecules, and the presence of the labeled molecule is determined using methods known in the art. Variations of the ELISA method, such as the competitive ELISA or competition assay, and sandwich ELISA, may also be used, as these are well-known to those skilled in the art.

In some embodiments, an IHC method may be used. IHC provides a method of detecting a biological marker in situ. The presence and exact cellular location of the biological marker can be detected. Typically, a sample is fixed with formalin or paraformaldehyde, embedded in paraffin, and cut into sections for staining and subsequent inspection by confocal microscopy. Current methods of IHC use either direct or indirect labelling. The sample may also be inspected by fluorescent microscopy when immunofluorescence (IF) is performed, as a variation to IHC.

Mass spectrometry, and particularly matrix-assisted laser desorption/ionization mass spectrometry (MALDI-MS) and surface-enhanced laser desorption/ionization mass spectrometry (SELDI-MS), is useful for the detection of biomarkers of this invention. (See U.S. Pat. Nos. 5,118,937; 5,045,694; 5,719,060; 6,225,047)

The presence and/or level of a nucleic acid in Table A can be evaluated using methods known in the art, e.g., using polymerase chain reaction (PCR), reverse transcriptase polymerase chain reaction (RT-PCR), quantitative or semi-quantitative real-time RT-PCR, digital PCR i.e. BEAMing ((Beads, Emulsion, Amplification, Magnetics) (Dichl et al., 2006); RNAse protection assay; Northern blot; various types of nucleic acid sequencing (Sanger, pyrosequencing, Next-Generation Sequencing); fluorescent in-situ hybridization (FISH); or gene array/chips) (Lehninger Biochemistry (Worth Publishers, Inc., current addition; Sambrook, et al, Molecular Cloning: A Laboratory Manual (3. Sup.rd Edition, 2001); (Bernard and Wittwer, 2002) (Bianchi et al., 2011; Miranda et al., 2010) (Taylor and Gercel-Taylor, 2013; Yang et al., 2014) (Nordstrom et al., 2000) (Ahmadian et al., 2000). In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289 (5485): 1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of the nucleic acids in the roof. Measurement of the level of a biomarker can be direct or indirect. For example, the abundance levels of a specific mRNA can be directly quantitated. Alternatively, the amount of a biomarker can be determined indirectly by measuring abundance levels of cDNA, amplified RNAs or DNAs, or by measuring quantities or activities of RNAs, or other molecules that are indicative of the expression level of the biomarker. In some embodiments a technique suitable for the detection of alterations in the structure or sequence of nucleic acids, such as the presence of deletions, amplifications, or substitutions, can be used for the detection of biomarkers of this invention.

RT-PCR can be used to determine the expression profiles of biomarkers (U.S. Patent No. 2005/0048542A1). The first step in expression profiling by RT-PCR is the reverse transcription of the RNA template into cDNA, followed by its exponential amplification in a PCR reaction (Ausubel et al (1997) Current Protocols of Molecular Biology, John Wiley and Sons). To minimize errors and the effects of sample-to-sample variation, RT-PCR is usually performed using an internal standard, which is expressed at constant level among tissues, and is unaffected by the experimental treatment. Housekeeping genes are most commonly used, e.g., GAPDH, TUBB, or GUSB.

Gene arrays are prepared by selecting probes that comprise a polynucleotide sequence, and then immobilizing such probes to a solid support or surface. For example, the probes may comprise DNA sequences, RNA sequences, co-polymer sequences of DNA and RNA, DNA and/or RNA analogues, or combinations thereof. The probe sequences can be synthesized either enzymatically in vivo, enzymatically in vitro (e.g. by PCR), or non-enzymatically in vitro.

TABLE A

| | | | 24-Gene VITAL Score | | | |
|---|---|---|---|---|---|---|
| cytokines | GenBank RefSeq ID | T cell | GenBank RefSeq ID | melanocyte | GenBank RefSeq ID |
| CXCL9 | NM_002416.2 | GZMB | NM_004131.5 or NM_001346011.1 | DCT | NM_001129889.2, NM_001322182.1, NM_001322183.1, NM_001322184.1, NM_001322185.1, NM_001322186.1, or NM_001922.4 |
| CXCL10 | NM_001565.3 | CD8A | NM_001145873.1, NM_001768.6, or NM_171827.3 | KIT | NM_000222.2 or NM_001093772.1 |
| CXCL11 | NM_005409.4, or NM_001302123.1 | CXCR3 | NM_001504.1 or NM_001142797.1 | TYR | NM_000372.4 |

TABLE A-continued

24-Gene VITAL Score

| cytokines | GenBank RefSeq ID | T cell | GenBank RefSeq ID | melanocyte | GenBank RefSeq ID |
|---|---|---|---|---|---|
| STAT1 | NM_007315.3, or NM_139266.2 | CD4 | NM_000616.4, NM_001195014.2, NM_001195015.2, NM_001195016.2, or NM_001195017.2 | TRPM1 | NM_001252020.1, NM_001252024.1, NM_001252030.1, or NM_002420.5 |
| CCL5 | NM_002985.2, or NM_001278736.1 | FOXP3 | NM_014009.3 or NM_001114377.1 | | |
| CCL18 | NM_002988.3 | | | | |
| IFNG | NM_000619.2 | other | | HOUSE | |
| IL23A | NM_016584.2 | HLA-A | | GAPDH | NM_001256799.2, NM_001289745.1, NM_001289746.1, or NM_002046.5 |
| TNF | NM_000594.3 | B2M | NM_004048.2 | TUBB | NM_001293212.1, NM_001293213.1, NM_001293214.1, NM_001293215.1, NM_001293216.1, or NM_178014.3 |
| CXCL2 | NM_002089.3 | | | GUSB | NM_000181.3, NM_001284290.1, NM_001293104.1, or NM_001293105.1 |

Reference Scores

Suitable reference score values can be determined using methods known in the art, e.g., using standard clinical trial methodology and statistical analysis. The reference values can have any relevant form.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

EXAMPLES

The invention is further described in the following examples, which do not limit the scope of the invention described in the claims.

Materials and Methods

The following materials and methods were used in the Examples set forth below.

Study Design

The objectives of this study were to determine whether Trm exist in human vitiligo, how they contribute to disease in a mouse model of vitiligo, and to determine whether these cells could be targeted therapeutically. These objectives were proposed to test the hypothesis that vitiligo is resistant to treatment because Trm persist in the skin and reactivate disease upon cessation of treatment. This hypothesis was formed based on clinical observations, as well as others reported in the literature (Ariotti, 2014; Clark et al., 2012; Jiang et al., 2012; Mackay et al., 2013; Schenkel et al., 2013; Skon et al., 2013; Watanabe, 2015).

Mice

All mice were housed in pathogen-free facilities at UMMS, and procedures were approved by the UMMS Institutional Animal Care and Use Committee and in accordance with the National Institutes of Health (NIH) Guide for the Care and Use of Laboratory Animals. Mice used for these studies were on the C57BL/6J (B6) background or a mixed 129×C57BL/6 background that had been backcrossed to B6 for more than 10 generations. Age and sex-matched mice were used, and both male and female mice of all strains were tested to avoid gender bias. Replicate experiments were performed two to five times.

KRT14-Kitl*4XTG2Bjl (Krt14-Kitl*) mice were a gift from B. J. Longley (University of Wisconsin, Madison, WI; now available at The Jackson Laboratory, stock no. 009687). The following strains were bred to Krt14-Kitl* mice for use as hosts in the vitiligo model: GREAT (The Jackson Laboratory, stock no. 017580), and REX3 (provided by A. Luster, Massachusetts General Hospital). For consistency, the Krt14-Kitl* allele was heterozygous on all mice used in vitiligo experiments. Thy 1.1+ PMEL TCR transgenic mice were obtained from The Jackson Laboratory (stock no. 005023) and were used as donors in the vitiligo model. GFP-PMEL TCR transgenic mice were produced by crossing PMEL transgenic mice with DPE-GFP mice, which express GFP in T cells (provided by U. von Andrian, Harvard Medical School, Boston, MA).

Vitiligo Induction

Vitiligo was induced as previously described (Harris et al., 2012). Briefly, PMEL CD8+ T cells were isolated from the spleens of PMEL TCR transgenic mice through negative selection on microbeads (Miltenyi Biotec) according to the manufacturer's instructions. Purified CD8+ T cells ($1\times10^6$) were injected intravenously into sublethally irradiated (500 rads 1 day before transfer) Krt14-Kitl* hosts (8 to 16 weeks of age). On the same day of transfer, recipient mice received intraperitoneal injection of $1\times10^6$ plaque-forming units of rVV-hPMEL (N. Restifo, National Cancer Institute, NIH).

Vitiligo score was objectively quantified by an observer blinded to the experimental groups, using a point scale based on the extent of depigmentation at four easily visible locations, including the ears, nose, rear footpads, and tails as described previously (Harris et al., 2012). The extent of depigmentation was estimated as a percentage of the anatomic site; both left and right ears and left and right rear footpads were estimated together and therefore evaluated as single sites. Points were awarded as follows: no evidence of depigmentation (0%) received a score of 0, >0 to 10%=1 point, >10 to 25%=2 points, >25 to 75%=3 points, >75 to <100%=4 points, and 100%=5 points. The "vitiligo score" was the sum of the scores at all four sites, with a maximum score of 20 points.

Repigmentation, Functionality and Durability Experiments

Vitiligo mice with >75% depigmentation and stable disease (between week 12-20 post-vitiligo induction) were used for repigmentation studies. FTY720 (Cayman chemical) treatment was performed by i.p. injection of (1) 1 mg/kg FTY720 diluted in water or (2) vehicle (water) three times weekly for the duration of the observation period (4 weeks) as previously described (Chiba, 2005; Murooka et al., 2012). IL-15Rβ antibody treatment was performed by i.p. injection of 100 μg of (1) anti-IL-15Rβ antibody ChMBC7 or (2) isotype control or vehicle (PBS) three times weekly. For long-term treatment studies, mice were treated for the duration of the observation period (8 weeks) for repigmentation studies. For durability studies, mice were treated for 2 weeks, and monitored for an additional 8 weeks after cessation of treatment. For functionality studies, mice were treated for 2 weeks, sacrificed at week 3, and PMEL T cells were restimulated ex vivo using 3 μg/ml plate bound anti-CD3 antibody with 2 μg/mL anti-CD28 antibody in complete RPMI with brefeldin A for 6-18 hours for cytokine production evaluation via flow cytometry analysis. Repigmentation analysis was performed with ImageJ. Photos were taken of each individual mouse before treatment and again after treatment was completed. The images were converted into black and white and the change in pigment was quantified with Image J software as previously described (Agarwal et al., 2015).

In Situ PMEL Labeling

Ears were injected with 40 μl of an antibody cocktail containing 0.05 mg/ml TCR-Vbeta 13-APC (BD Biosciences clone MR12-3) and 0.35 mg/ml Fc block 2.4G2. 2 hours post injection, mice were euthanized and ears excised. The dorsal and ventral sides were separated and mounted on slides for confocal microscopy (Cummings et al., 2008).

Study Subjects

Patient shave skin biopsies and suction blister biopsies were collected under IRB-approved protocols at UMMS by board-certified dermatologists, and all samples were de-identified before use in experiments. For suction blister skin biopsies, lesional sites were chosen based on the presence of depigmentation. Active patients were defined as having changes in their lesions over the previous 6 months, as well as the presence of confetti depigmentation, a recently described clinical sign of active vitiligo (Sosa et al., 2015). Stable patients were defined as lacking confetti depigmentation, and having no changes in their lesions over the previous 6 months. Non-lesional sites were selected as normal-appearing, non-depigmented skin when examined by Wood's lamp, at least 2 cm from the nearest depigmented macule. Patients were excluded from the study if they had received treatment within the previous three months.

Blister Induction and Processing

Suction blisters were induced on the skin using the Negative Pressure Instrument Model NP-4 (Electronic Diversities, Finksburg MD) as previously described (Strassner et al., 2017). Briefly, the suction chambers were applied to the patient skin with 10-12 mm Hg of negative pressure and a constant temperature of 40° C.; blisters formed between 30 minutes and one hour after initiation of the procedure. After blister formation, the blister fluid was aspirated using 1 mL insulin syringes. Cells within the blister fluid were pelleted at 330× g for 10 minutes for cell staining and the supernatant was collected for ELISA.

Flow Cytometry & Cell Sorting

Tail skin and draining lymph nodes were harvested at the indicated times. Lymph nodes were disrupted and tail skin was incubated with 5U/mL Dispase II (Roche) for 1 h at 37° C. Epidermis was removed and mechanically dissociated using 70 μm filters. Dermis was incubated with 1 mg/mL collagenase IV and 2 mg/mL DNAse I (Sigma Aldrich) for 1 h at 37° C. before mechanical dissociation. Samples were filtered prior to staining and analysis, and UltraComp eBeads (eBiosciences) were used for compensation controls. All murine flow cytometry samples were blocked with Fc block 2.4G2 (Bio X Cell) and stained with LiveDead Blue (Invitrogen, 1:1000). The following antibodies were used at a 1:200 dilution: CD45, Thy1.1, CD3, CD8B, CD69, CD44, CD103, and CD62L (Biolegend). IL-15Rα (R&D Systems) was used at a 1:10 dilution (10 μL per 100 μL). For intracellular cytokine staining with IFNγ and Granzyme B antibodies (Biolegend), a Cytofix/Cytoperm kit (BD Biosciences) was used per the manufacturer's instructions.

All human flow cytometry samples were blocked with Human TruStain FcX (Biolegend) and LiveDead Blue (Invitrogen 1:1000). The following antibodies were used at a 1:20 dilution: CD45, CD4 (Tonbo Biosciences), and CD8, HLA-A2, CD69 and CD103 (Biolegend). CD3 (Biolegend) was used at a 1:200 dilution. Human blood was screened for HLA-A2 expressing cells by flow cytometry, and HLA-A2 positive patient samples were treated with 50 nM dasatinib (Axon Medchem BV) for 30 minutes prior to labeling with a MART-1 loaded class I pentamer (Proimmune) per the manufacturer's protocol. Additional surface staining was performed to identify phenotypes of antigen-specific cells. Peripheral blood was used to make FMOs to assist in gating, and samples were stained, then fixed and lysed using RBC Fixation/Lysis Buffer (Biolegend) per the manufacturer's instructions. Data were collected with an LSR II and were analyzed with FlowJo software.

Statistics

All statistical analyses were performed with GraphPad Prism software. Dual comparisons were made with unpaired Student's t test, and groups of three or more were analyzed by ANOVA with Tukey's or Dunnett's post-tests. P values<0.05 were considered significant.

Figure 1B:
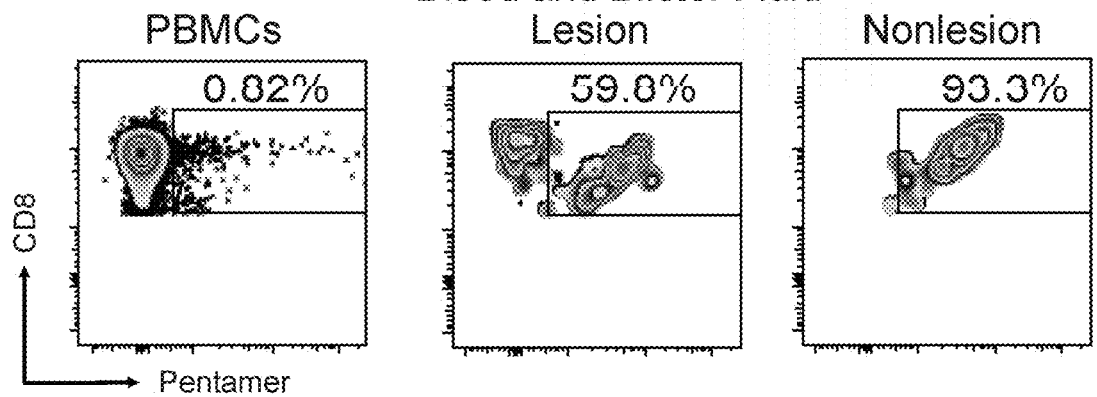
Figure 1B:
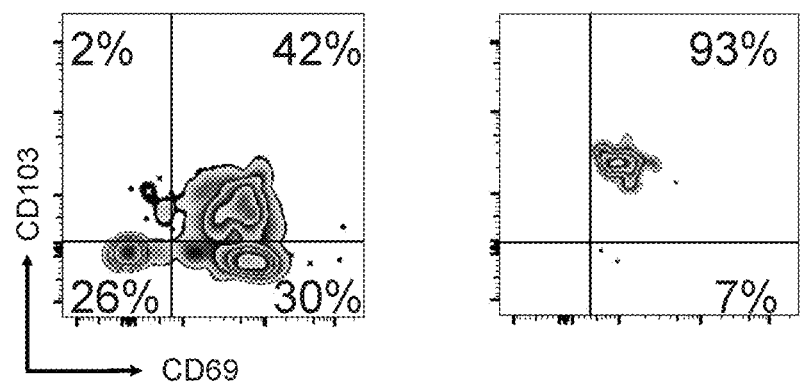
Figure 1C:
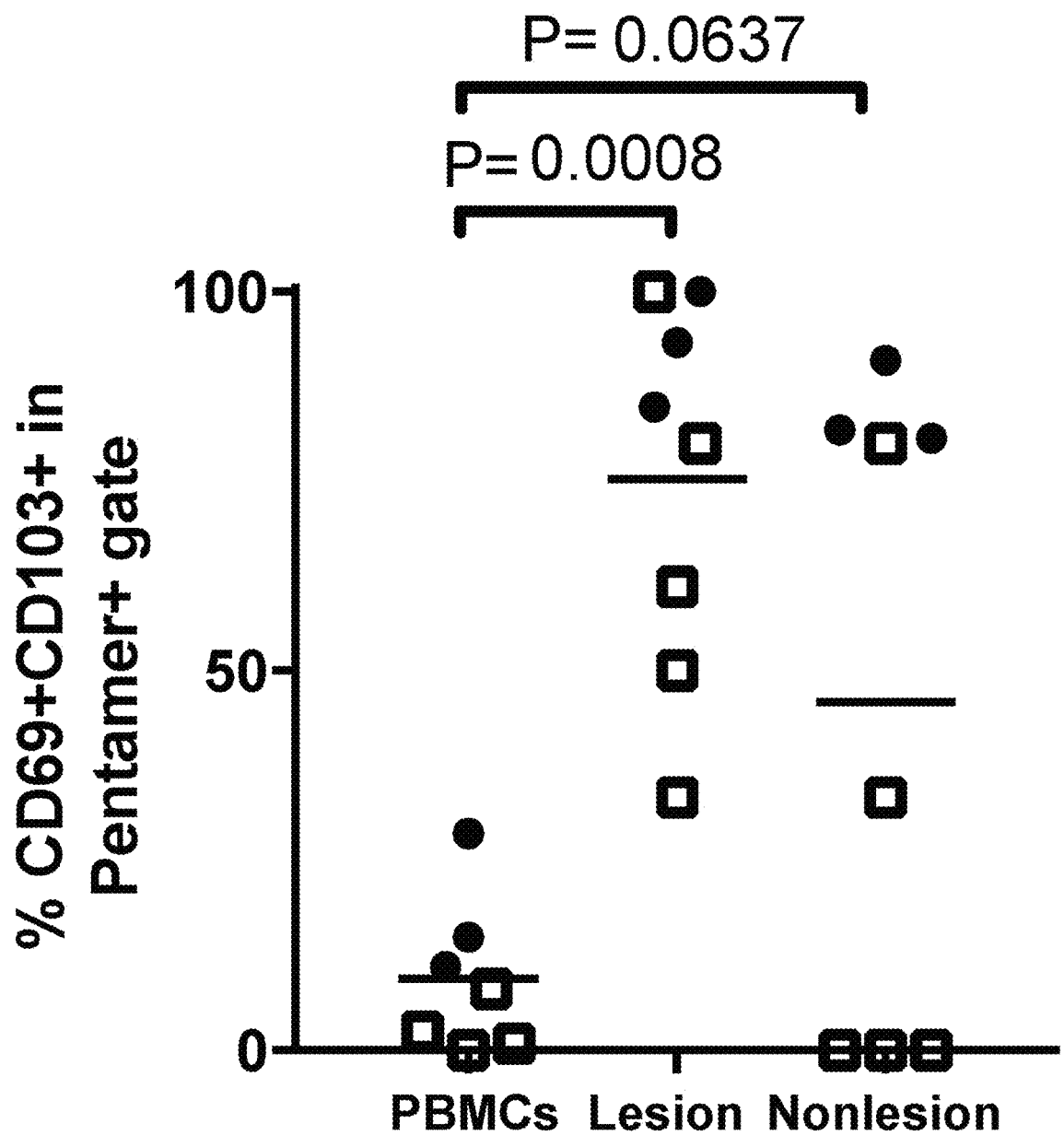
Figure 1D:
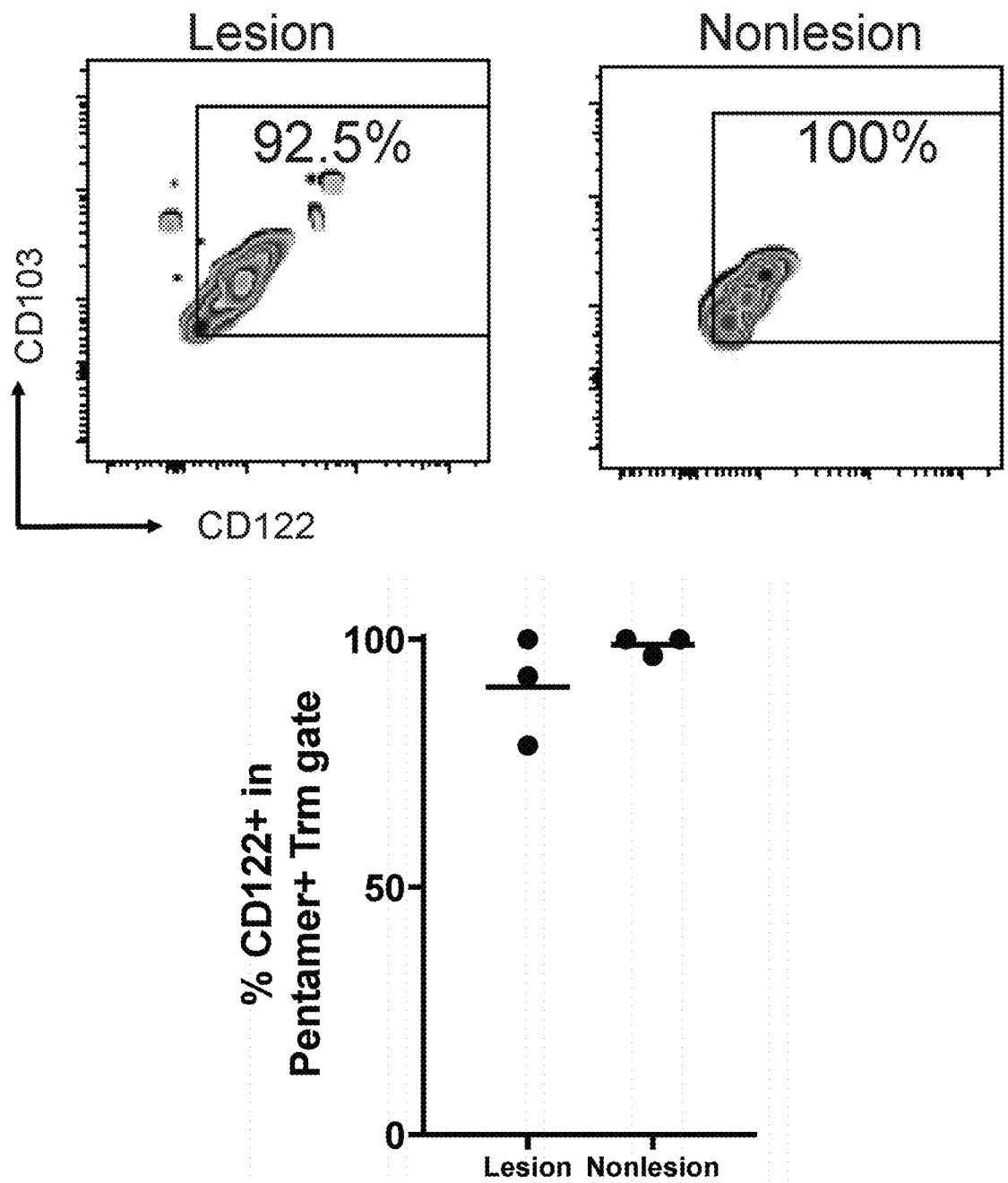
Figure 1E:
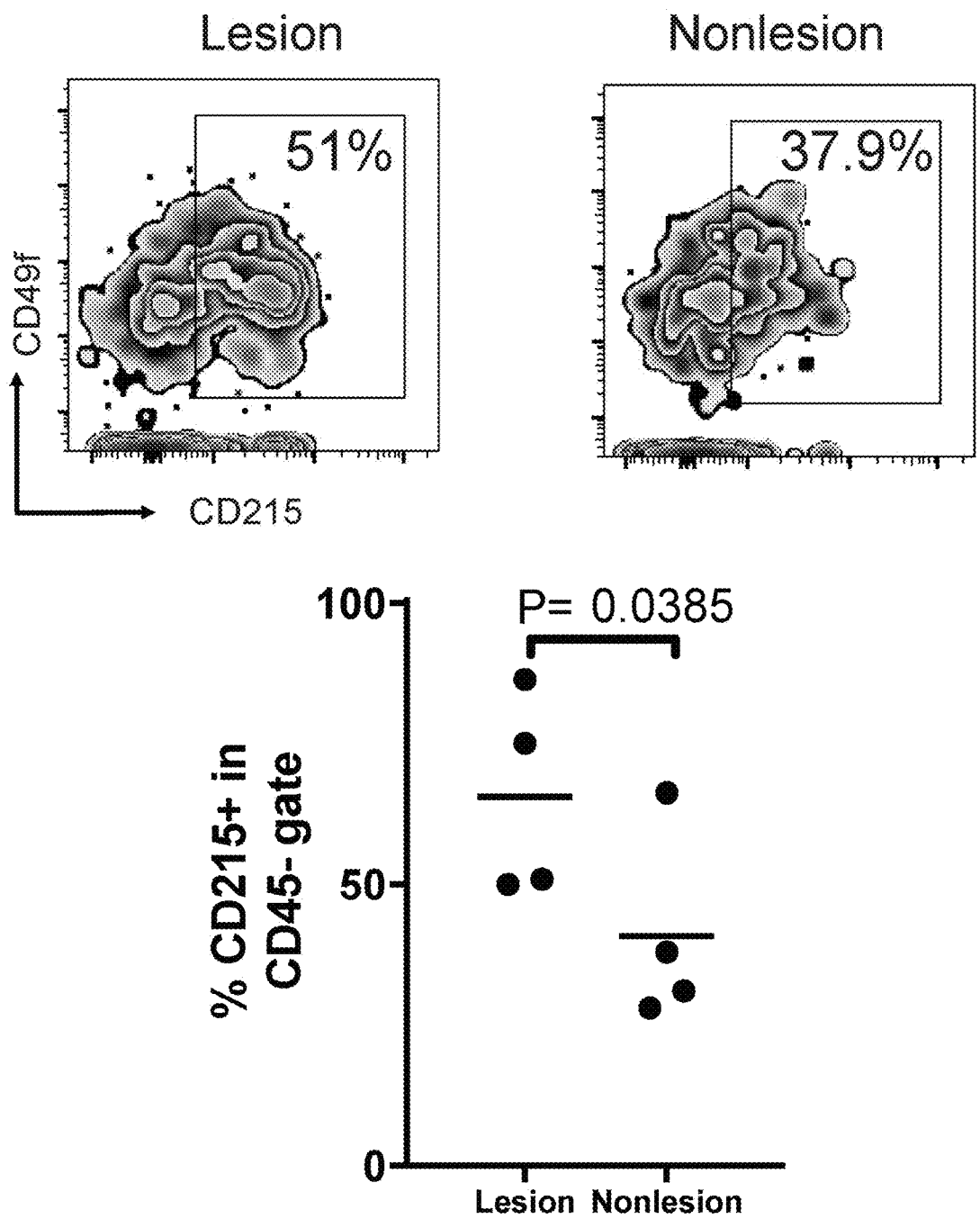
Figure 1F:
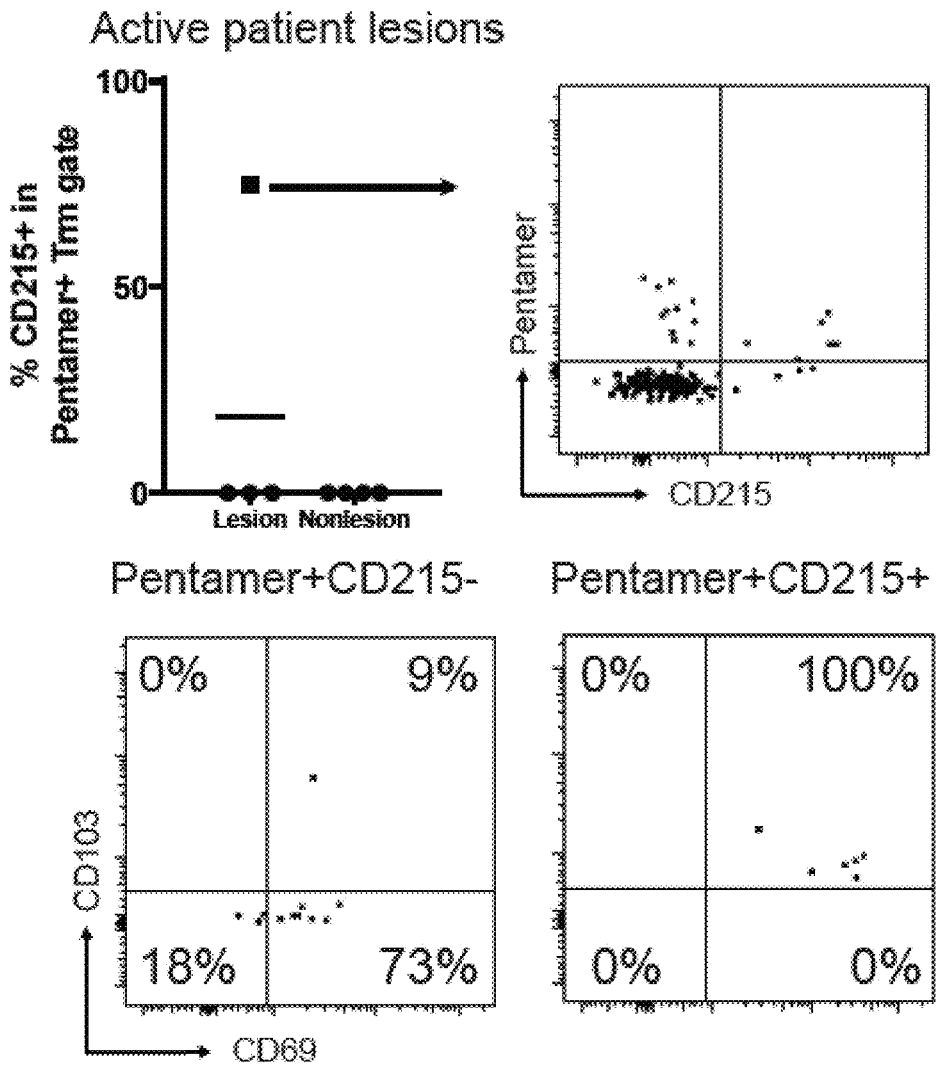

Example 1. Autoreactive T Cells Within Lesions of Vitiligo Patients Express a Trm Phenotype, and Express IL-15R Viral infections of the skin generate both central memory T cells (Tcm) that localize to lymph nodes and recirculate, as well as resident memory T cells (Trm) that remain in the skin for very long periods, and both populations help prevent reinfection. We hypothesized that melanocyte-specific Trm cells form long-lived memory cells within the vitiligo lesions, similar to those in viral infections, and make them refractory to treatment. We performed blister biopsies on vitiligo patients with active and stable disease (FIG. 1A) (Strassner et al., 2017). We identified antigen-specific T cells in both blood and skin fluid from these patients. In patients with active disease, the majority of antigen-specific T cells were CD69 single positive, whereas in stable disease they were CD69+CD103+ (FIG. 1B). There was an enrichment of antigen-specific T cells in lesional fluid with a Trm phenotype (FIG. 1C). Antigen-specific cells Trm expressed the CD122 chain of the IL-15R (FIG. 1D). Keratinocytes express the CD215 chain of the IL-15 receptor to present IL-15 in trans to T cells, and keratinocytes in lesional skin express higher CD215 than in nonlesional skin (FIG. 1E). Taken together, these data indicate that human vitiligo patients possess antigen-specific Trm cells in lesional skin that express IL-15Rβ/CD122.

Figure 2A:
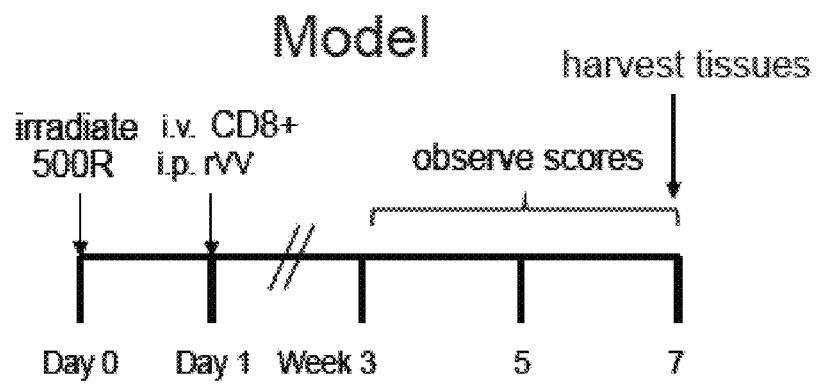
FIGS. 2A-2G. Only melanocyte-specific T cells form Trm in the epidermis. (A) Schematic of the mouse model of vitiligo. (B) Epidermal PMEL from vitiligo mice are CD69+CD103+. (C) Mice were given VV-OVA and OT-1 T cells to compare another model antigen to (D) the PMEL/vitiligo system. (E) Mice that received OVA-specific cells and virus did not develop vitiligo. (F) OT-1s and PMEL engrafted equally in the draining lymph nodes. (G) Only PMEL established long-lived epidermal populations. Each dot represents one animal; representative experiment of two shown.
Figure 2B:
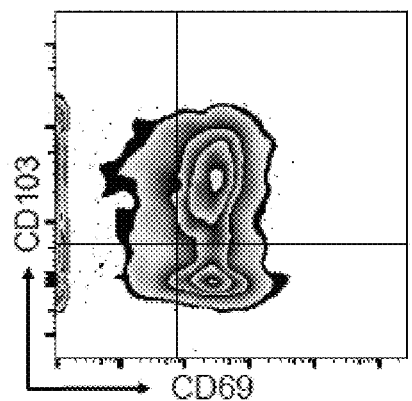
Figure 2C:
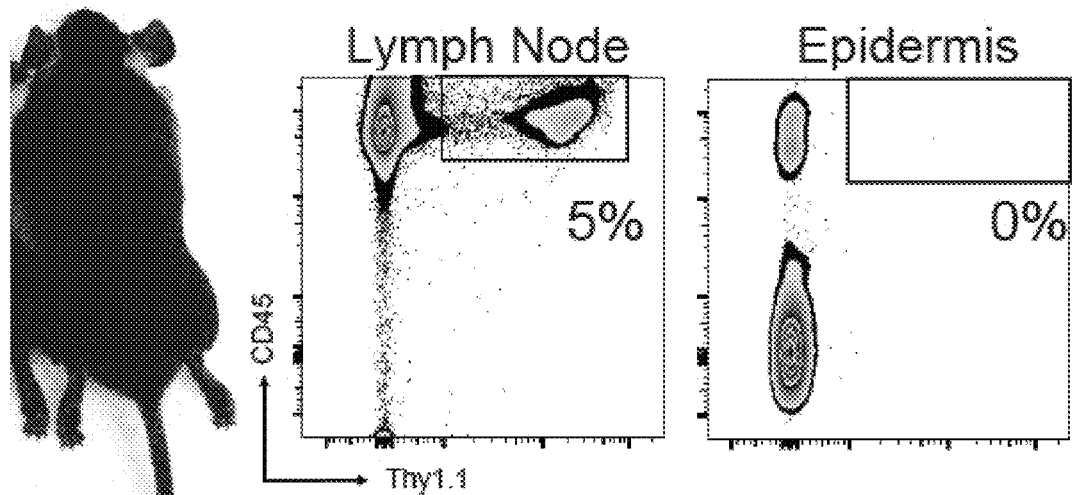
Figure 2D:
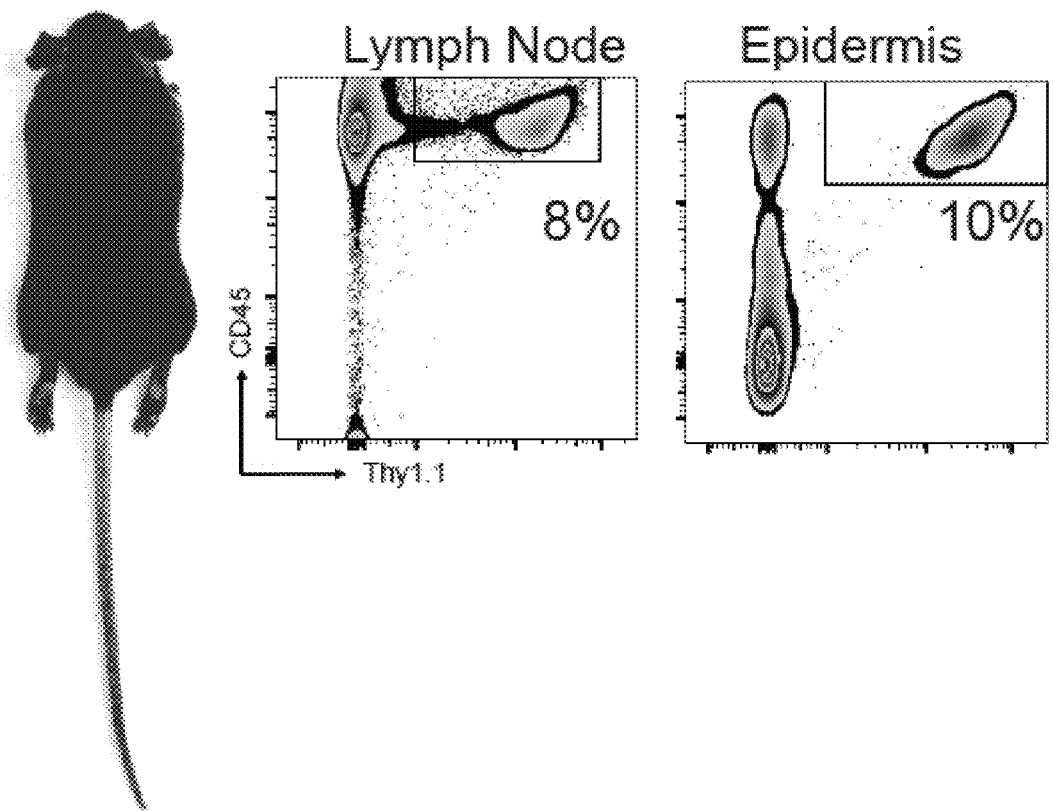
Figure 2E:
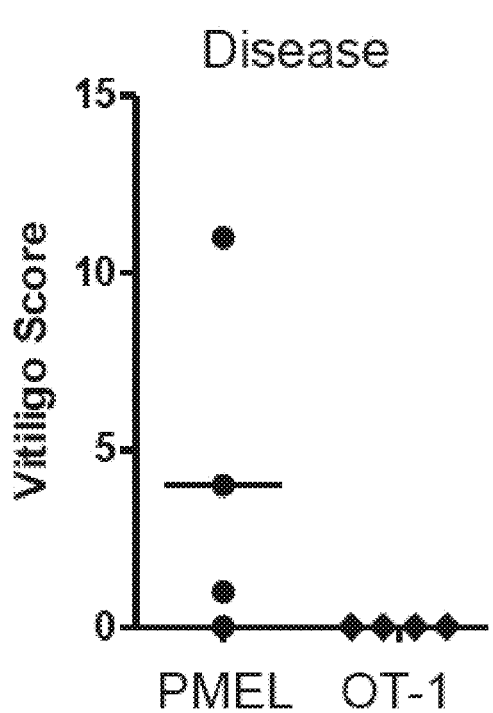
Figure 2F:
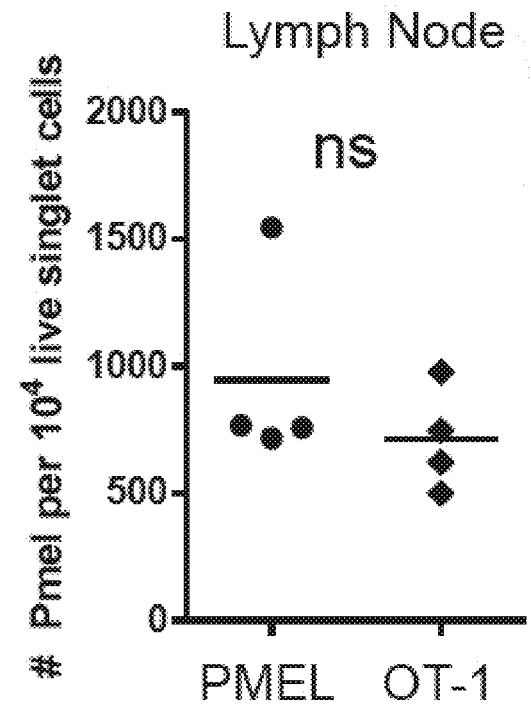
Figure 2G:
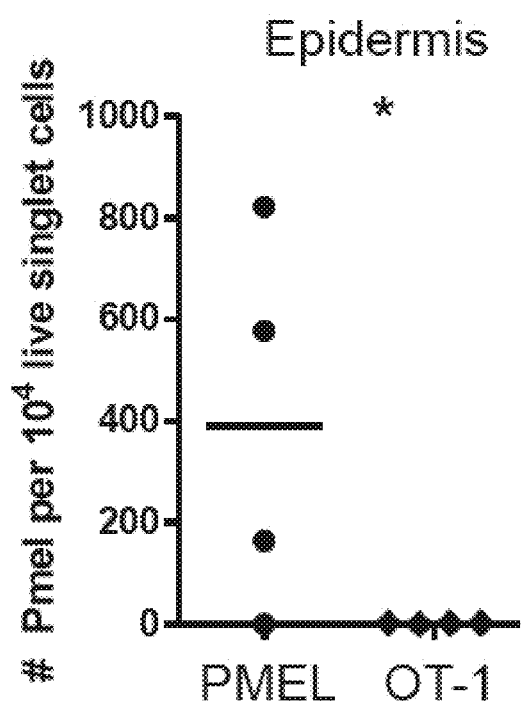

Example 2. Autoreactive T Cells in the Epidermis of a Mouse Model of Vitiligo Possess a Resident Memory Phenotype To address the functional roles of Trm in vitiligo, we employed our mouse model, which uses the adoptive transfer of CD8+ T cells that recognize the autoantigen Pre-melanosome protein (PMEL) physiologically expressed in melanocytes (FIG. 2A). Previous studies using this model revealed that adoptively transferred, autoreactive T cells accumulate within the epidermis of the skin during the progression of vitiligo (Agarwal et al., 2015; Harris et al., 2012; Rashighi et al., 2014) (8, 9, 12). We found that these cells accumulate in the epidermis where melanocytes reside, and that a large fraction of these cells expressed both CD69 and CD103, markers of Trm formation (FIG. 2B).

To determine the role of self antigens in the recruitment and retention of Trm within the epidermis of mice with autoimmunity, we compared the generation of skin Trm that recognize PMEL physiologically expressed in melanocytes to T cells that recognize the irrelevant foreign OVA antigen (OT-1). We induced immune responses with recombinant vaccinia virus (VV) expressing pre-melanosome protein (VV-PMEL) and PMEL T cells, or expressing ovalbumin (VV-OVA) and OT-1 T cells. Only melanocyte-specific T cells established Trm in the epidermis, whereas OT-1s did not (FIG. 2C-G). These data indicate that autoreactive Trm are generated directly in the skin where autoantigen is expressed during vitiligo in our mouse model.

Figure 3A:
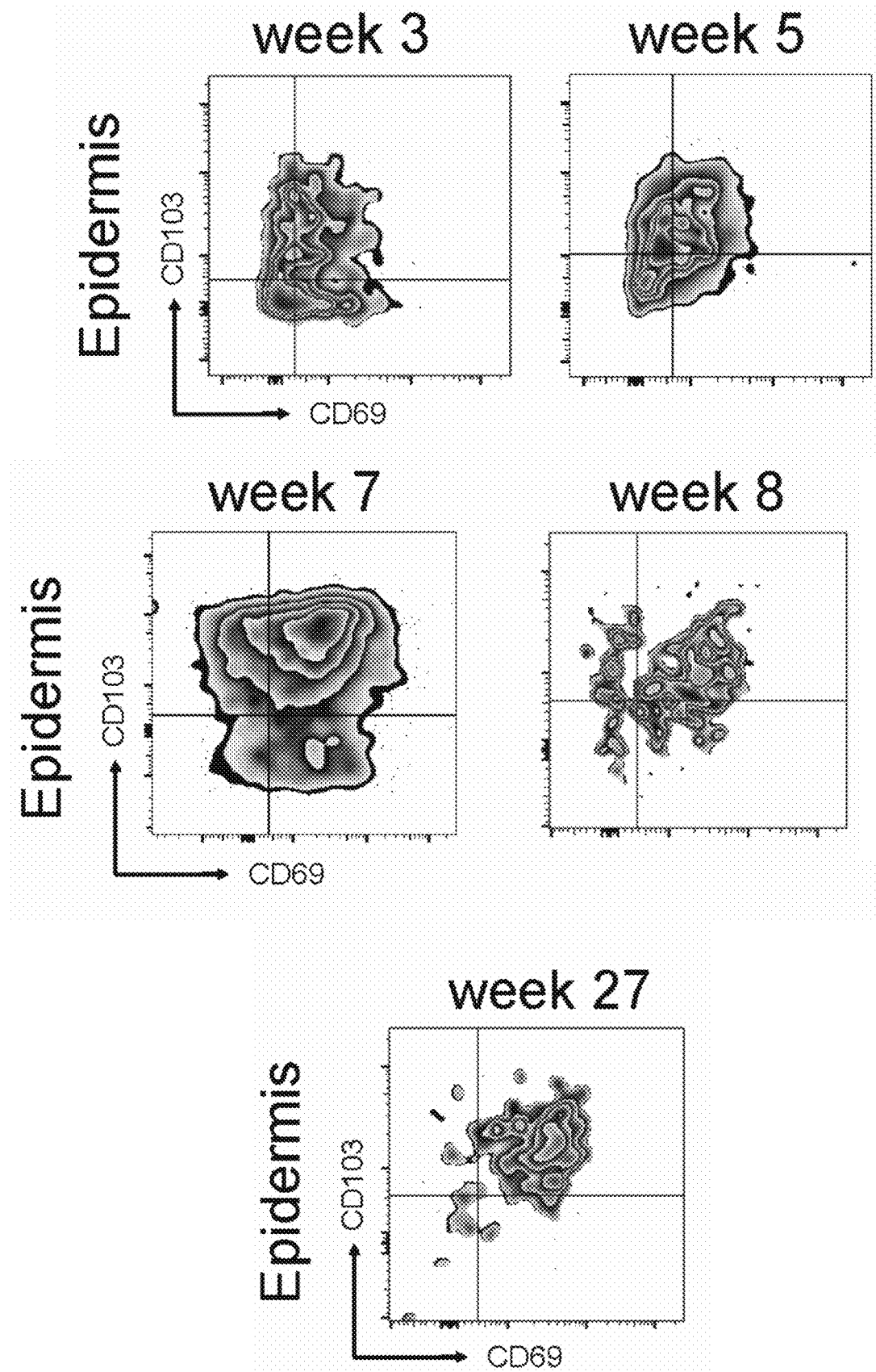
FIGS. 3A-3D. Characterization of PMEL Trm in the vitiligo mouse model reveals they are long-lived and produce IFNγ. (A) Sample flow plots pre-gated on live single epidermal PMEL at the indicated times. (B) Quantification of epidermal PMEL numbers and frequency of CD69+CD103+ PMEL over time in the vitiligo model. (C) Frequency of epidermal PMEL producing IFNγ in the model, and mouse disease scores over time. (D) Representative confocal image of ear skin reveals sparsely populated PMEL that produce IFNγ (week 10; 10× z stack maxima image; auto-fluorescent hair visible as green lines in GFP channel; white arrows indicate IFNγ-GFP+ PMEL, yellow arrows indicate IFNγ-GFP-PMEL; scale bar 25 µm). (n=2-8 mice per timepoint pooled from 4 separate experiments)
Figure 3B:
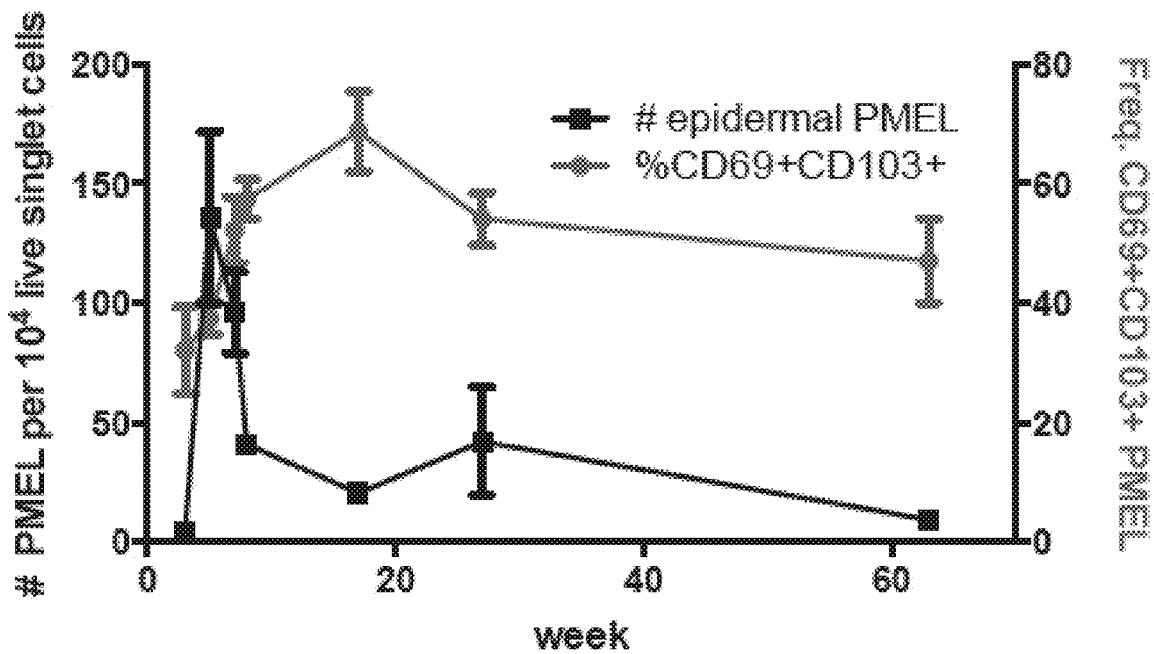

Example 3. PMEL Trm are Long-Lived, Produce IFN-γ, and Chronically Encounter Self-Antigen Self-reactive Trm in vitiligo differ from viral-reactive Trm in that they are frequently re-exposed to antigen as target cells regenerate, in contrast to viral antigen that is cleared. Thus, we measured the kinetics of transformation of autoreactive T cells into Trm, their persistence over time, activation status, and functional status. We found that PMEL upregulate CD69 and CD103 maximally by 7-8 weeks post vitiligo induction (FIGS. 3A and 3B). In accordance with previous studies, PMEL Trm also downregulated CCR7 and CD62L (Table 1). PMEL infiltration in the epidermis was maximal between weeks 5-7, indicating ongoing inflammation and active disease. After this time, the autoreactive T cell pool in the epidermis contracted, and remaining cells were mostly of the Trm phenotype; therefore, we considered any time point after 7 weeks the stable/Trm phase of disease. Mice maintained a pool of approximately 25-50 PMEL per 10,000 live single epidermal cells that were 60-80% CD69+ CD103+ past 30 weeks. Total PMEL numbers in the epidermis waned one-year post vitiligo induction, though the proportion of Trm PMEL in that pool was maintained. We also found distinct populations of melanocyte-specific Tcm/Tem (CD44+CD62L+) in lymph nodes and spleen (summarized in Table 1).

Figure 3C:
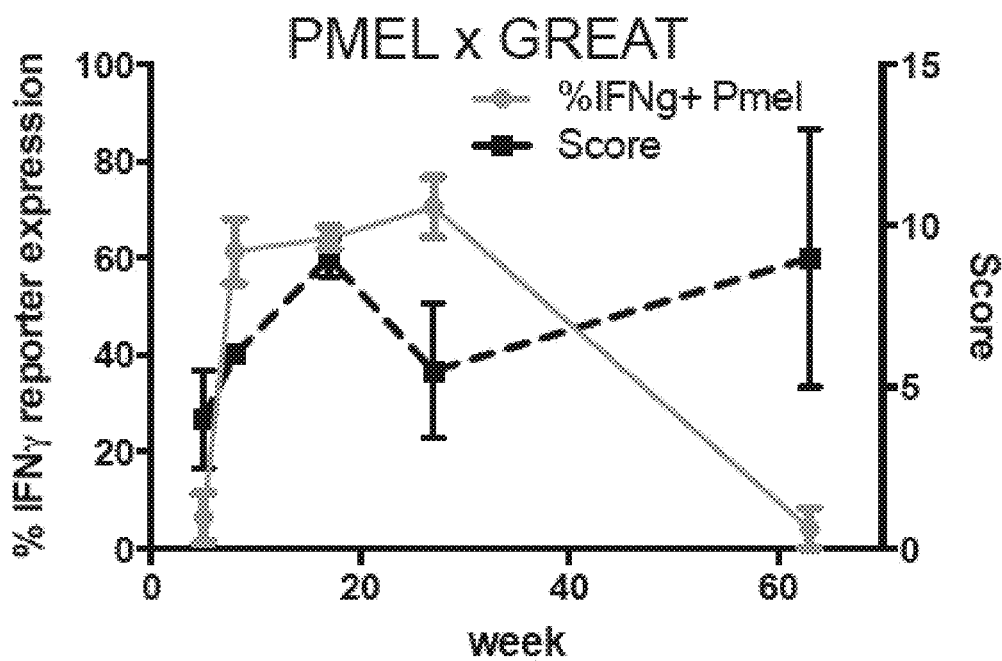
Figure 3D:
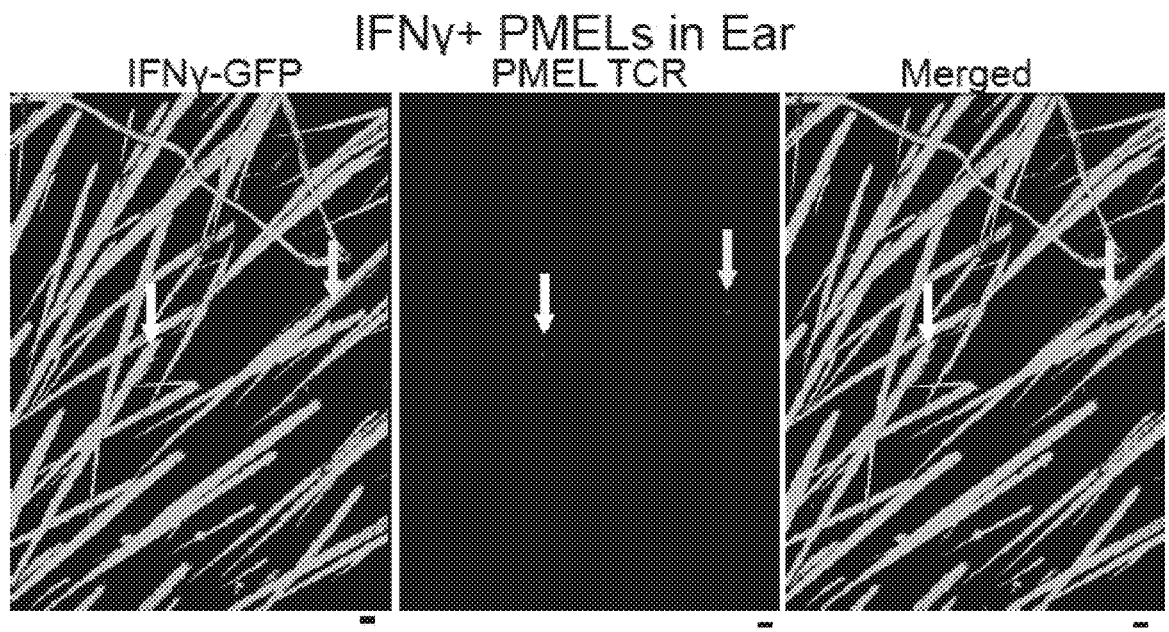
Figure 4A:
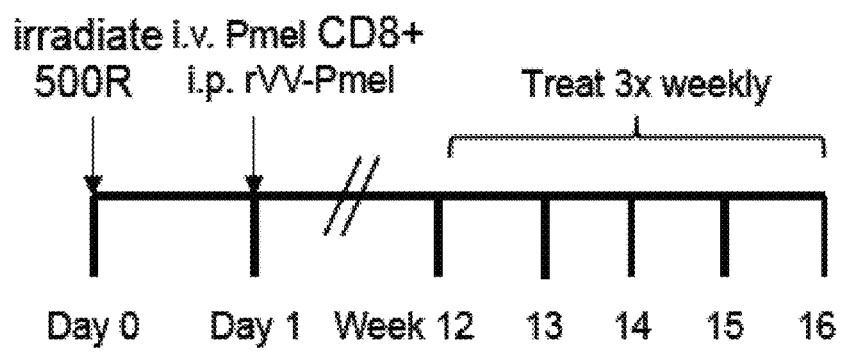
FIGS. 4A-4G. FTY720 treatment reverses disease in mice with established vitiligo. (A) Timing of treatments in the repigmentation model. (B) Sample photos of vehicle control and FTY720 treated animals at baseline and week 4. Percent of tail pigmentation before and after treatment in (C) control and (D) FTY720 treated animals. (E) Comparison of the final percent change in pigmentation in PBS and FTY720 treated animals. (F) Total number and (G) frequency of CD69+CD103+ epidermal PMEL in treated animals. (each dot represents one animal pooled from 3 separate experiments)
Figure 4B:
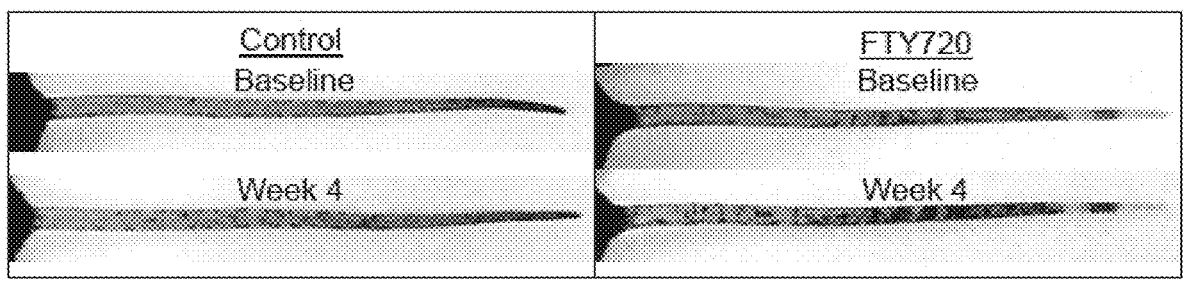
Figure 4C:
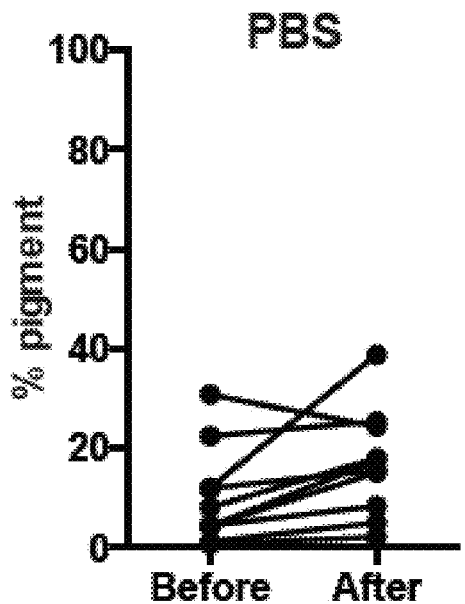
Figure 4D:
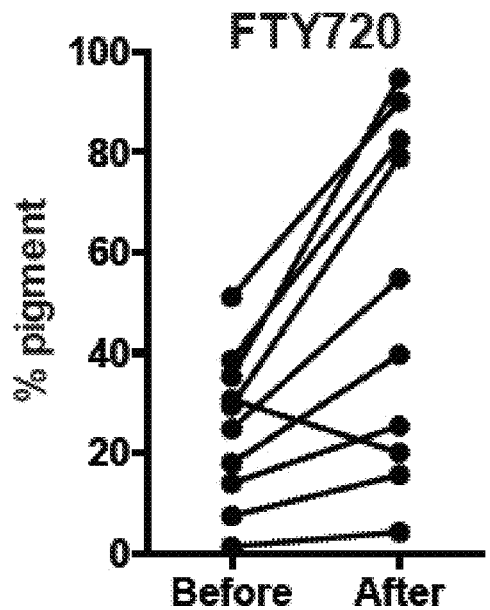
Figure 4E:
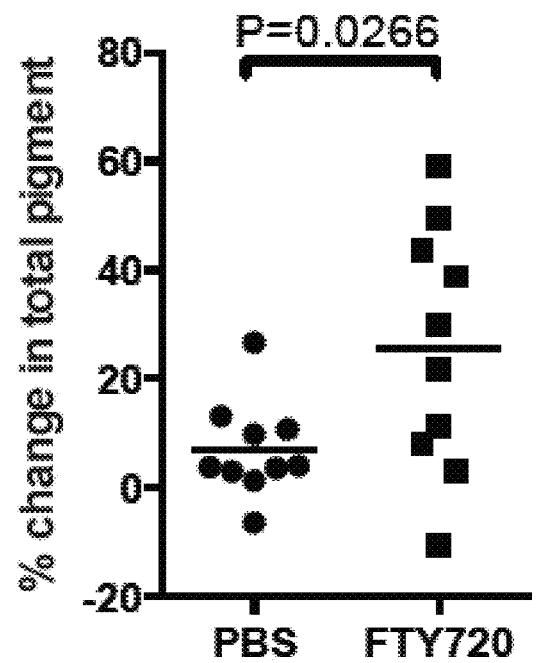
Figure 4F:
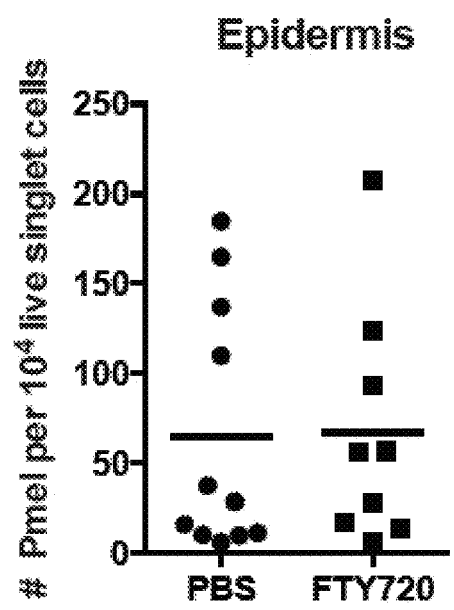
Figure 4G:
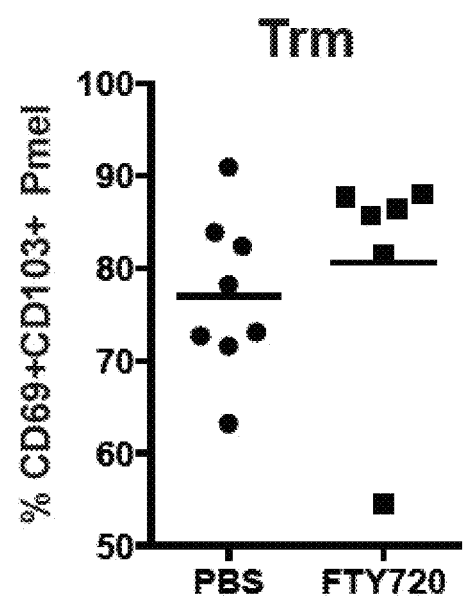

We previously reported that vitiligo is dependent on IFNγ and IFNγ-dependent chemokines (Agarwal et al., 2015; Harris et al., 2012; Rashighi et al., 2014). Therefore, we evaluated the effector function of autoreactive Trm in our model. We bred PMEL mice to GREAT mice, which report IFNγ expression (Reinhardt et al., 2009). We found that PMEL Trm maintain IFNγ reporter expression up to 30 weeks post-vitiligo induction (FIGS. 3C and 3D). By 60 weeks, IFNγ reporter expression was reduced to basal levels, possibly due to exhaustion of the T cells, or depletion of the melanocyte stem cell reservoirs resulting in reduced self-antigen load in the skin. Taken together, these data indicate that PMEL Trm are long-lived and maintain effector function for long periods.

TABLE 1

Phenotype characteristics of PMEL in different tissues in the vitiligo mouse model.

| Marker | Epidermis | Dermis | Spleen | Lymph Node | Blood |
|---|---|---|---|---|---|
| CD93 | 70% | 60% | 5% | 25% | 2% |
| CD44low/+ | 20% (55% CD93+) | 50% (54% CD93+) | 2.5% (60% CD93+) | 12% (75% CD93+) | 2.5% (31% CD93+) |
| KLRG1 | 4% | 12% | 34% | 5% | 58% |
| CD52L | 0% | 0% | 4% | 13% | 5% |
| CD126 | 0% | 2% | 3% | 5% | 0% |
| CCR5 | 23% | 28% | 14% | 14% | 2% |
| PD-1 | 5% (all CCR5+) | 3% | 0% | 1% | 0% |
| CXCR3 | 1% | 7% | 52% | 68% | 85% |

Example 4. Persistence of Depigmentation In Vitiligo Requires Circulating Memory T Cells Previous studies in virus models are conflicted as to the function of Trm within tissues. Some studies report enhanced effector function of Trm (Jiang et al., 2012), while others describe primarily an alarm function that serves to efficiently recruit effectors to sites of reinfection (Ariotti, 2014; Schenkel et al., 2013). We previously reported that blocking CXCL10 not only prevented the progression of vitiligo, but also reversed stable disease, demonstrating that the chemokine continued to play an important role even after melanocytes were destroyed and Trm became established in the epidermis (Rashighi et al., 2014). This suggested that Trm may not be sufficient for the memory observed in lesions after treatment is discontinued. In addition, it suggested that continued chemokine production is required to maintain depigmentation in the lesions.

We evaluated the role of circulating PMEL populations in maintenance of vitiligo using the S1P1 inhibitor FTY720, which inhibits circulation of T cells from the lymph nodes, to determine whether T cell recirculation is required during the maintenance of vitiligo. We found that treatment with FTY720 resulted in rapid reversal of disease (FIGS. 4A-G). In accordance with other studies (Pinschewer et al., 2000), PMEL Trm were still present in the skin after treatment. These data indicate that recirculating memory T cells contribute to sustained melanocyte killing during the maintenance of vitiligo, and that Trm are not sufficient effectors for this function.

Figure 5:
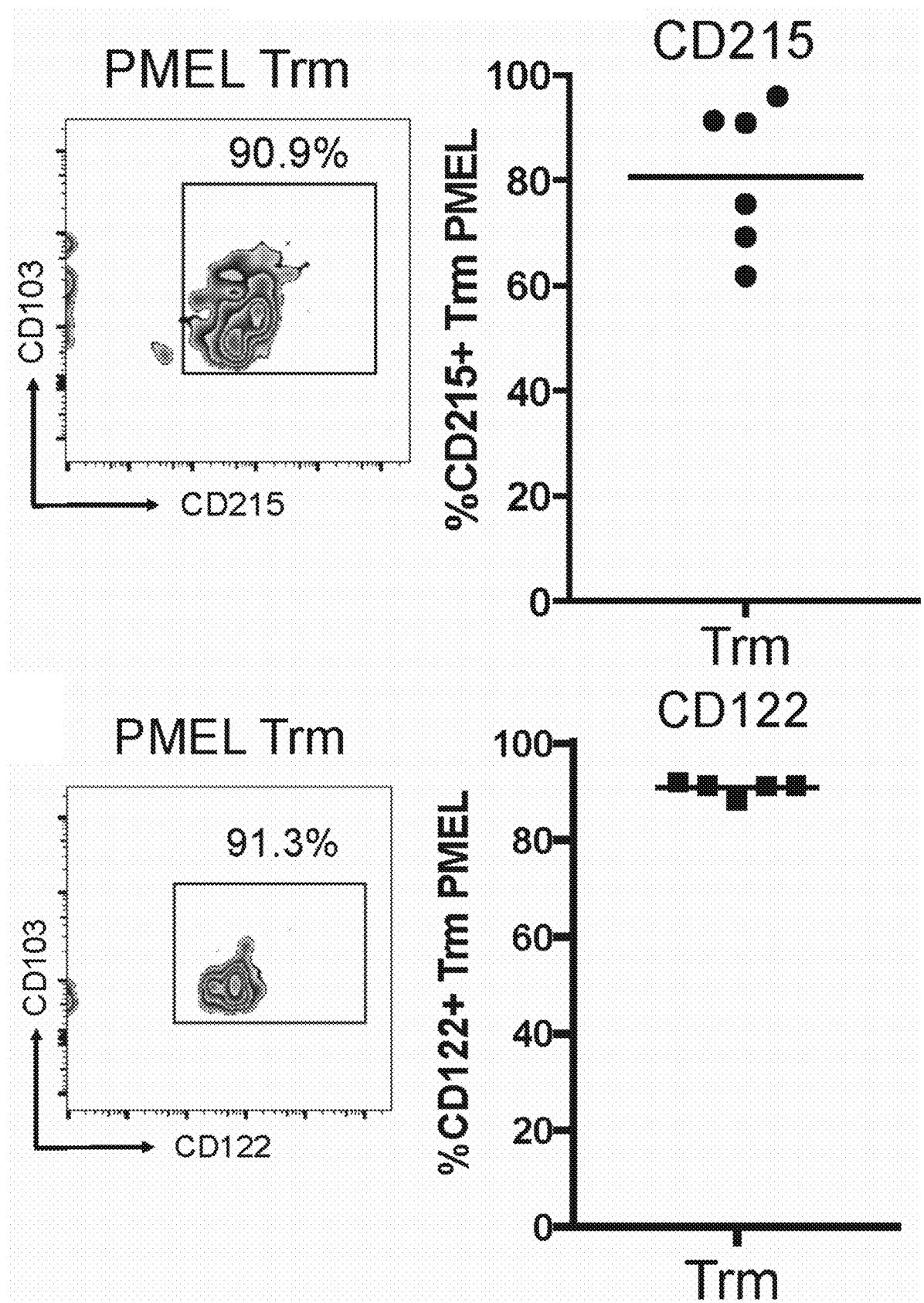
FIG. 5. Expression of IL-15Rα on PMEL Trm. Mouse epidermal PMEL were pre-gated on live single CD69+CD103+ and then assessed for IL-15Rα (CD215, top) and IL-15Rβ (CD122, bottom) expression.

Example 5. IL-15Rβ is Required for the Function and Maintenance of Trm in the Skin, and IL-15Rβ Blockade Serves as a Durable Treatment Existing treatments for vitiligo are not durable, as the disease returns at the site of treatment after discontinuation. The persistence of Trm following FTY720 treatment indicates this also will not be a durable therapy, as they remain in the tissue and would likely regain their function after stopping the treatment. Previous studies reported that IL-15 signaling was important for the generation of skin Trm that reside in hair follicles (Adachi et al., 2015), and we hypothesized that targeting this cytokine might deplete Trm in the skin and result in long-lasting repigmentation. We first confirmed that the majority of PMEL expressed the IL-15R (CD122 & CD215 antibodies; FIG. 5). To test the impact of IL-15 on the survival and maintenance of the Trm population in the epidermis, mice with longstanding, stable vitiligo (>12 weeks after disease initiation) were treated with an anti-mouse IL-15Rβ antibody, which blocks IL-15 signaling. The antibody used, ChMBC7, is a chimeric rat/mouse antibody with diminished Fc-mediated effector functions.

Figure 6A:
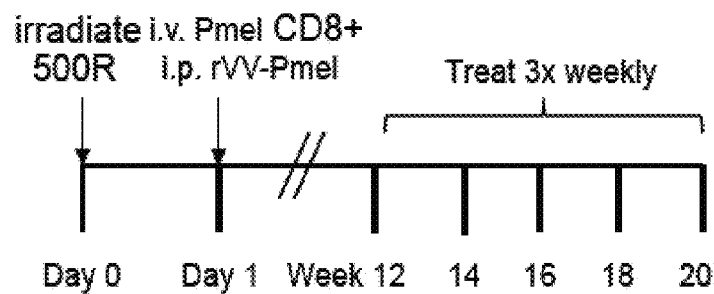
FIGS. 6A-6I. Treatment with IL-15Rβ Ab durably reverses disease in mice with established vitiligo. (A) Timing of treatments in the efficacy/repigmentation model. (B) Sample photos of vehicle control (PBS or isotype) and IL-15Rβ Ab treated animals at baseline and week 8. (C) Comparison of the final percent change in pigmentation in vehicle and IL-15Rβ Ab treated animals. (D) Quantification of PMEL numbers in treated animals in the indicated tissues. (E) Quantification of host CD8+ T cell numbers in treated animals in the indicated tissues. (each dot represents one animal pooled from 2 separate experiments; T tests significant as indicated). (F) Timing of treatments in the durability study. (G) Sample photos of vehicle control (PBS or isotype) and IL-15Rβ Ab treated animals at baseline and week 8. (H) Comparison of the final percent change in pigmentation in vehicle and IL-15Rβ Ab treated animals (T test significant as indicated). (I) Analysis of the percent of tail with pigmentation over time (two-way ANOVA p=0.0015 for treatment, p<0.0001 for time, and ns for interaction with Dunnett's comparisons to baseline pigmentation significant as indicated by stars). (Each dot represents one animal pooled from 3 separate experiments)
Figure 6B:
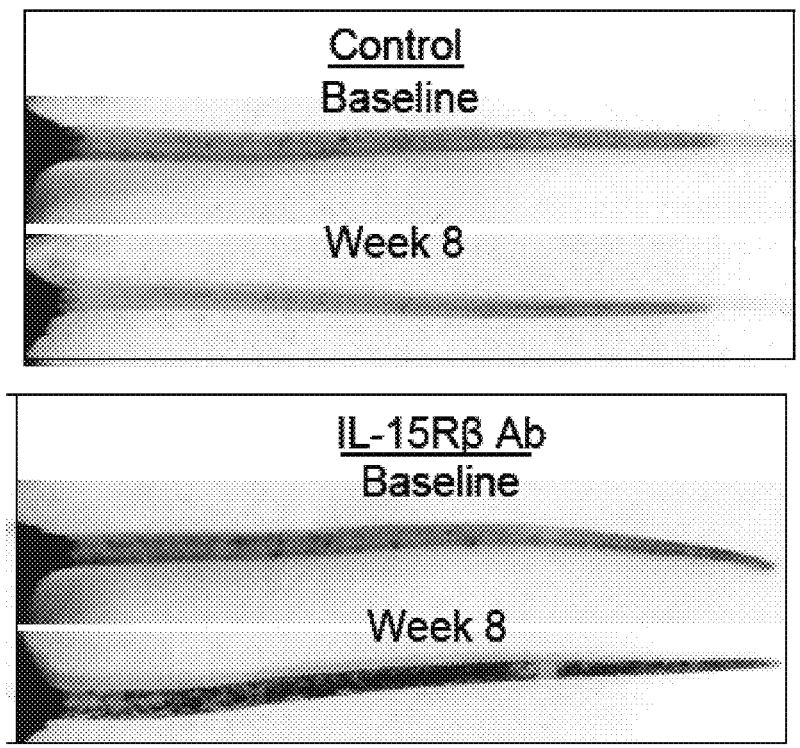
Figure 6C:
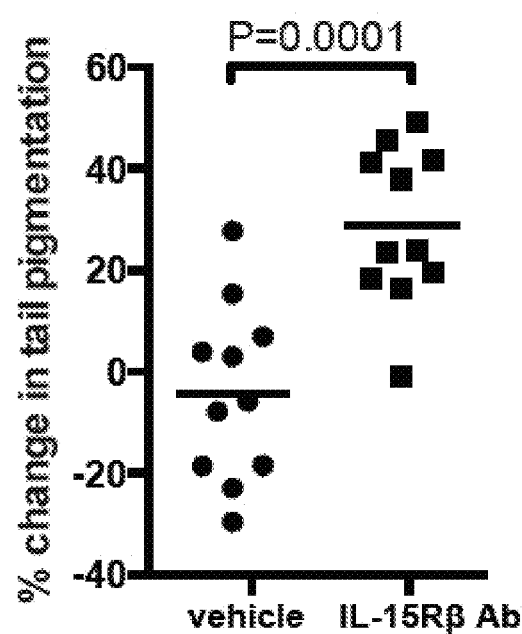
Figure 6D:
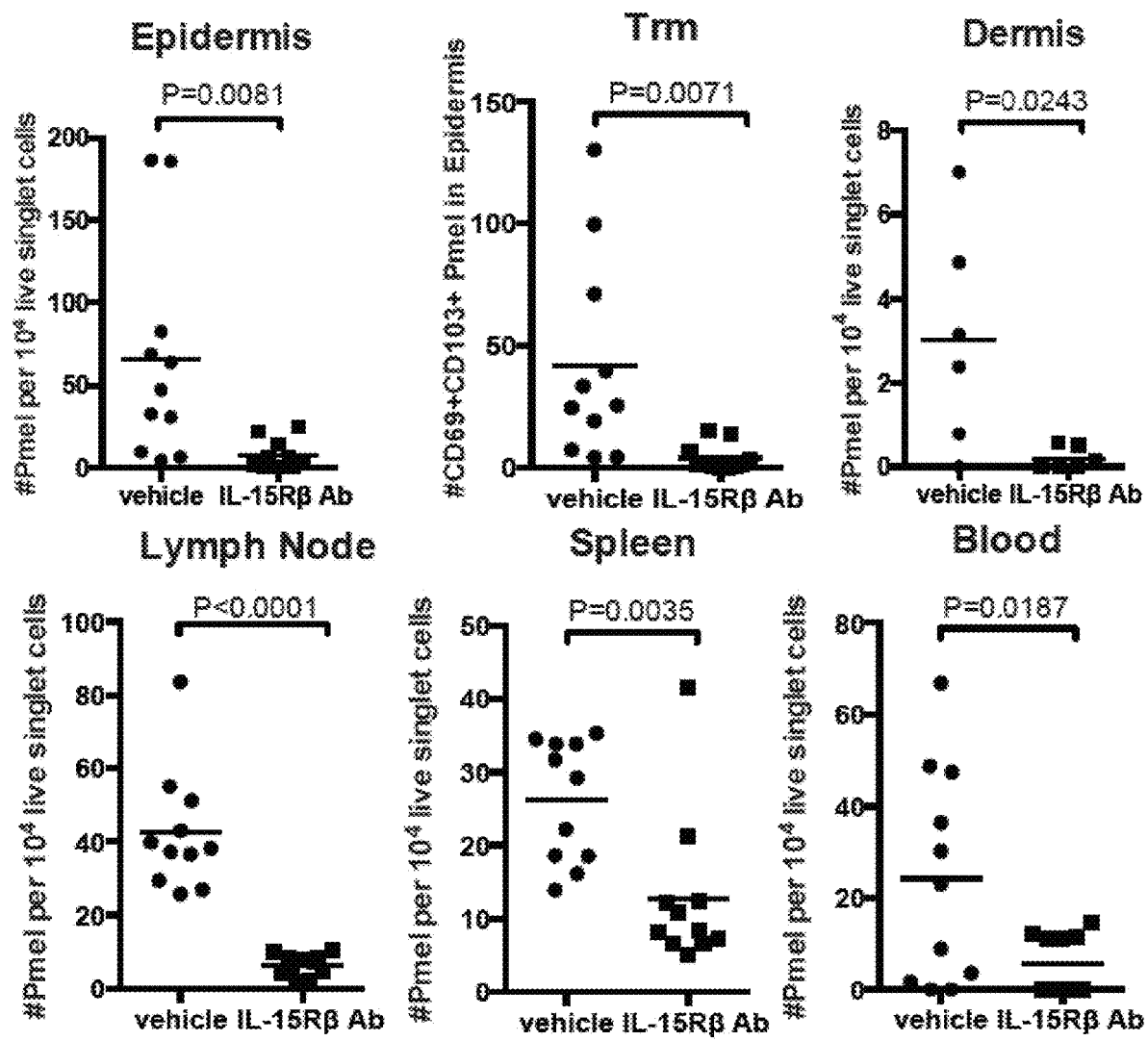
Figure 6E:
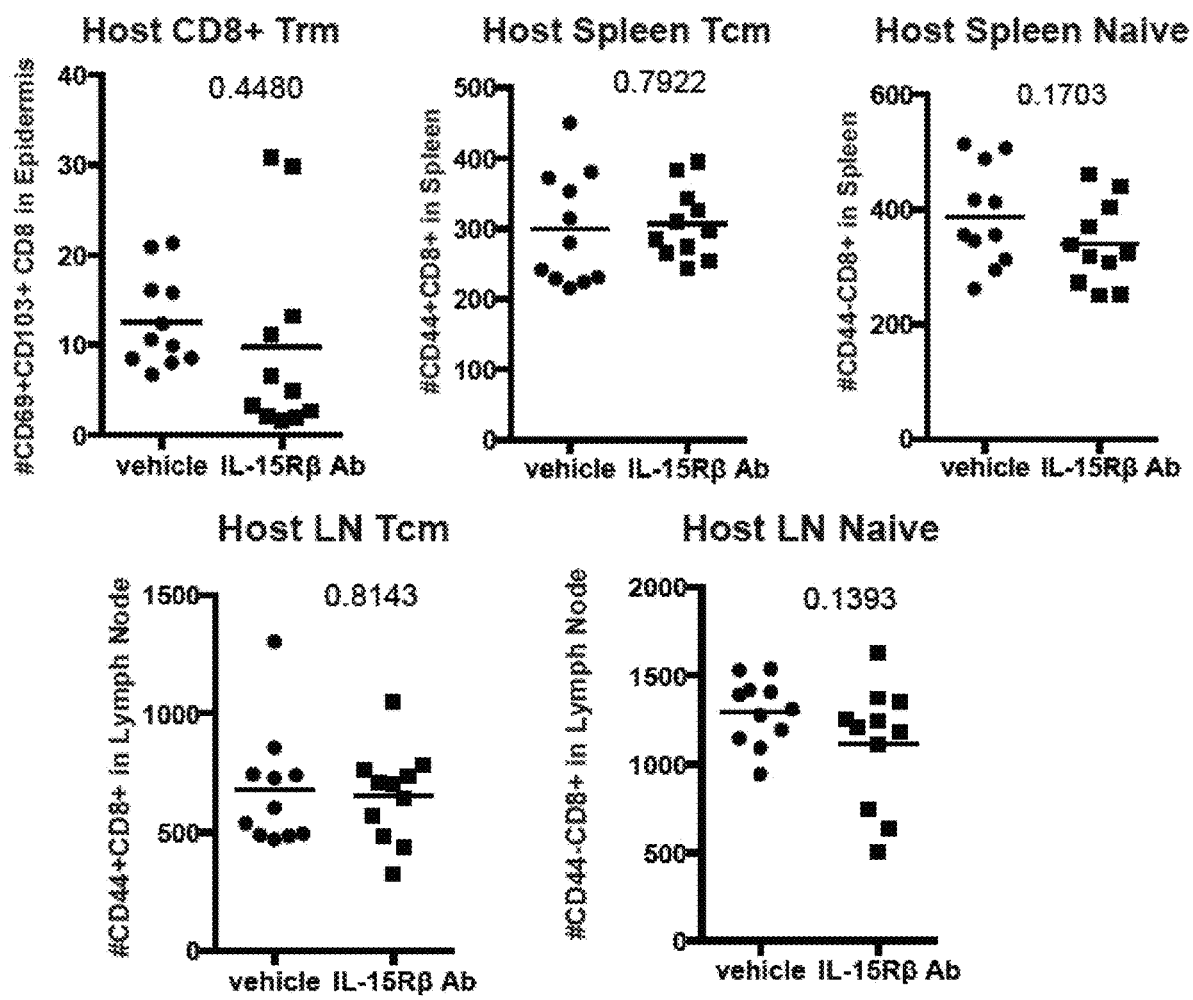
Figure 6F:
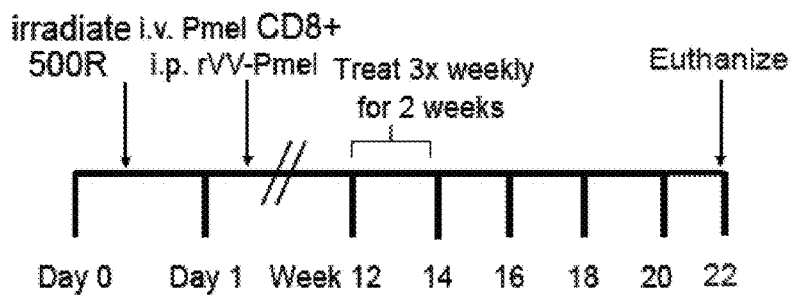
Figure 6G:
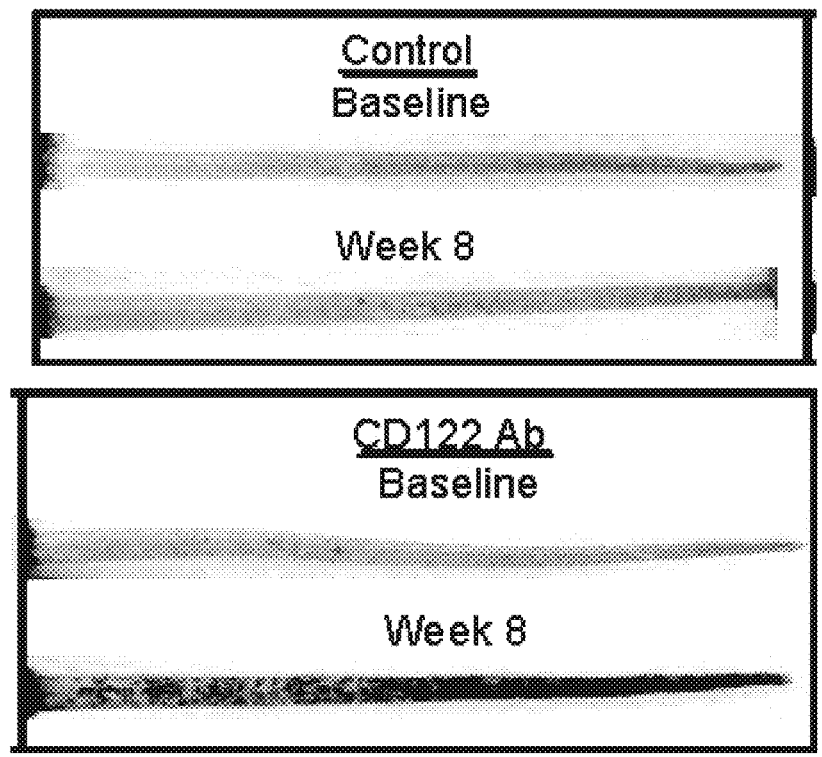
Figure 6H:
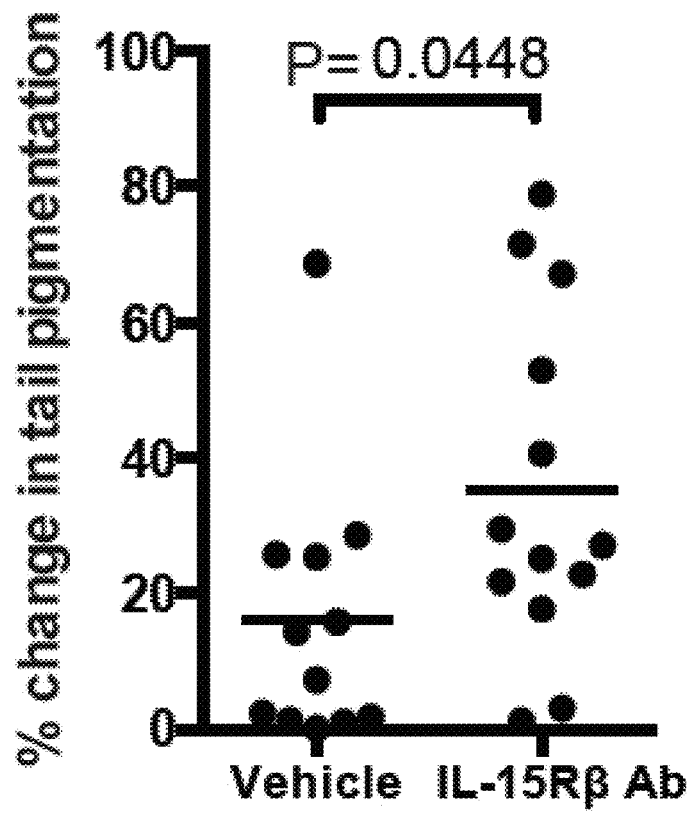
Figure 6I:
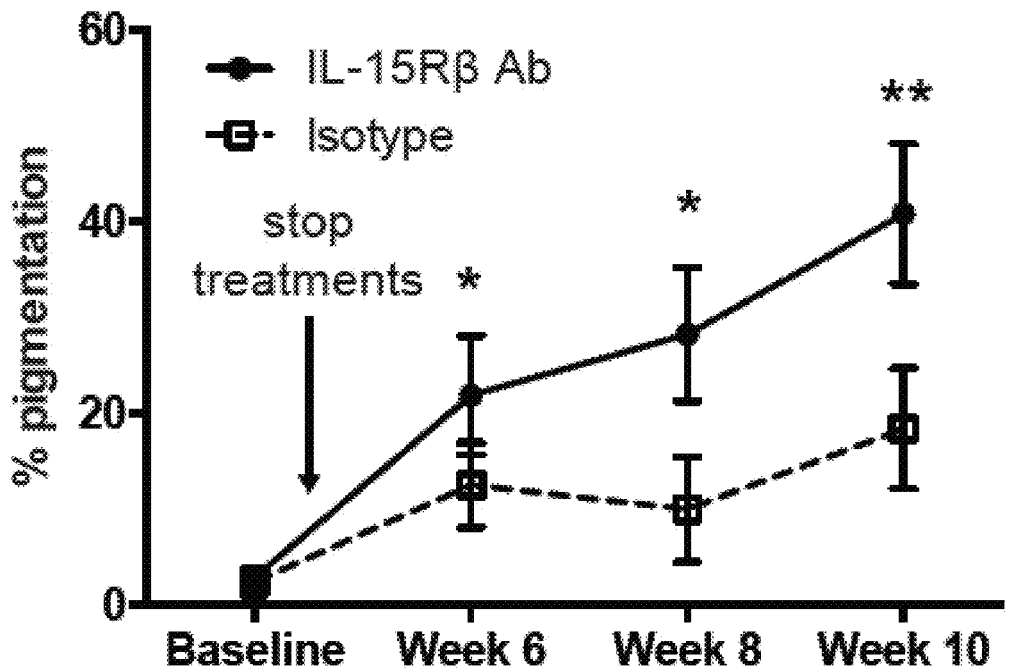
Figure 7A:
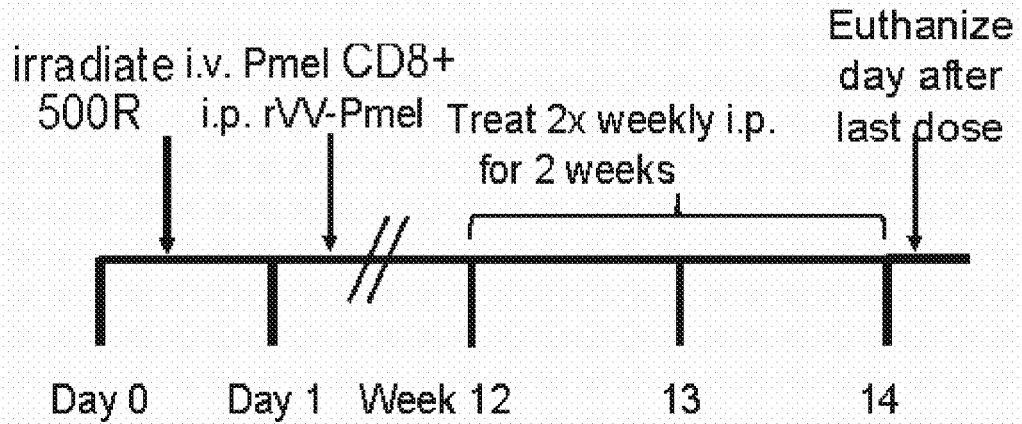
FIGS. 7A-7C. Short-term treatment with IL-15Rβ Ab reduces IFNγ secretion by PMEL. (A) Timing of treatments in the systemic functionality study. (B) Sample flow plots of epidermal PMEL from vehicle or CD122 antibody treated mice showing granzyme B and IFNγ production. (C) Frequency of IFNγ+ PMELs from the lymph nodes, epidermis, and dermis of mice in the systemic functionality study (each dot represents one animal pooled from 4 separate experiments; T tests significant as indicated).
Figure 7B:
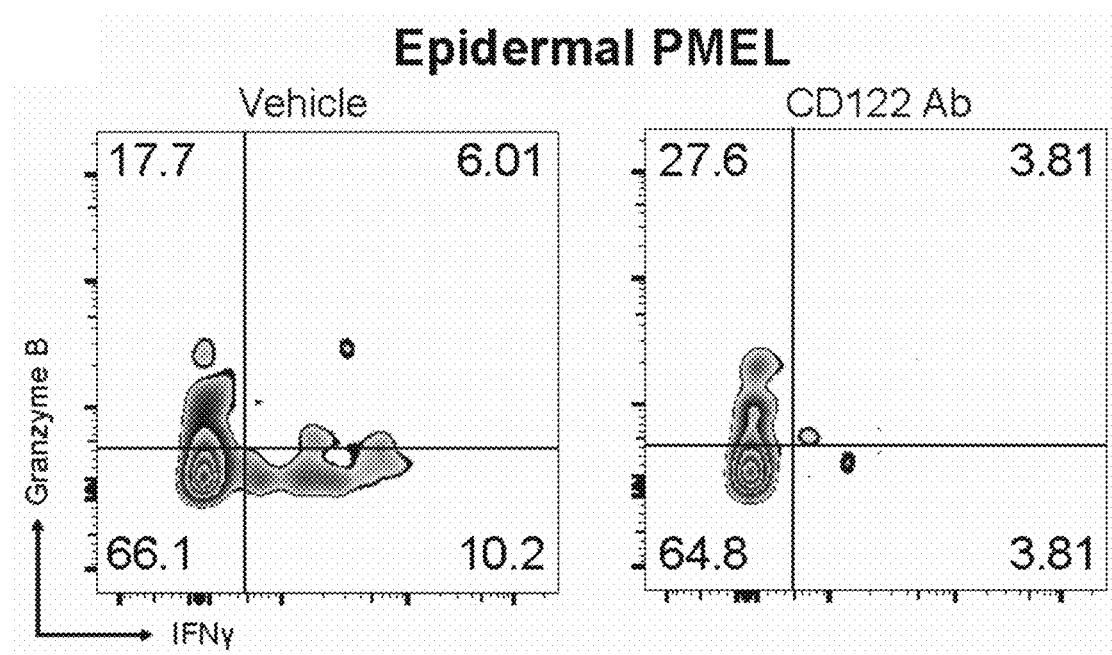
Figure 7C:
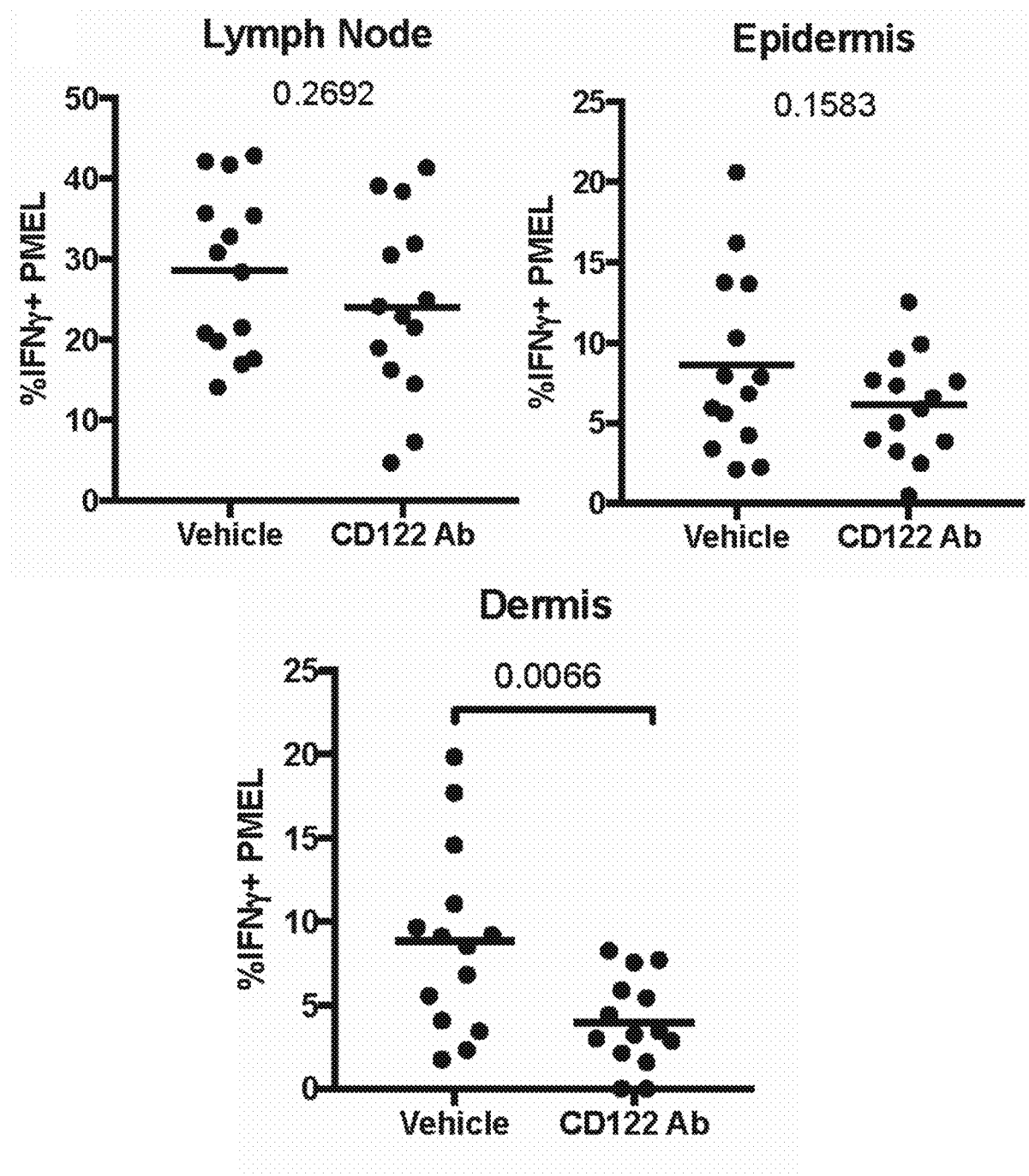
Figure 8A:
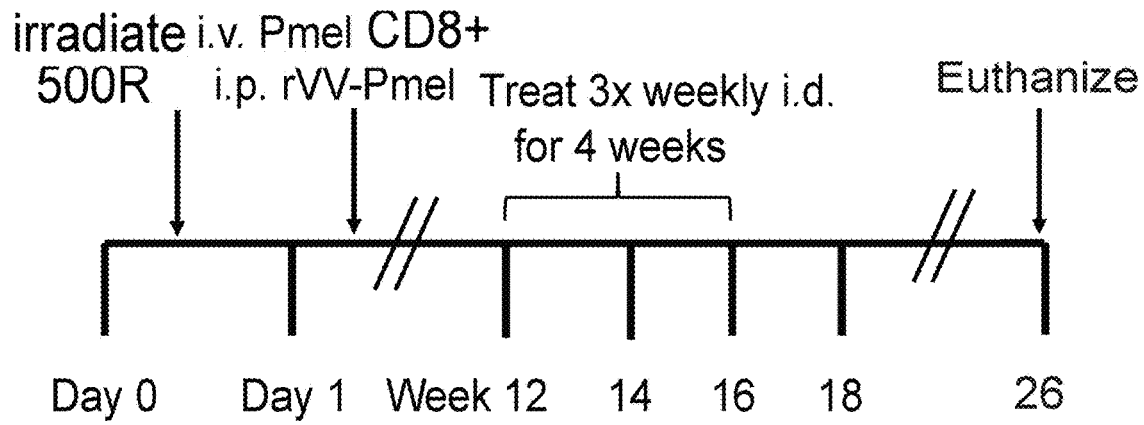
FIGS. 8A-8E. Local intradermal injection of CD122 antibody treatment durably reverses disease in mice. (A) Timing of treatments in the durability study. (B) Sample photos of vehicle control (PBS or isotype) and CD122 antibody treated animals at treatment baseline and week 12. (C) Comparison of the final percent change in pigmentation in control and CD122 antibody treated animals (Each dot represents one animal pooled from 2 separate experiments, n=7 control and 9 CD122 antibody treated mice; T test significant as indicated). (D) Analysis of the percent of tail with pigmentation over time (two-way ANOVA ns for treatment and time, p=0.0017 for interaction with Dunnett's comparisons to baseline pigmentation with simple effects within treatment groups significant as indicated by stars, baseline versus week 10 p=0.0197, and baseline versus week 12 p=0.0002). (E) Quantification of PMEL numbers in treated animals within the indicated tissues. (Each symbol represents 1 animal pooled from 2 separate experiments; all t tests ns).
Figure 8B:
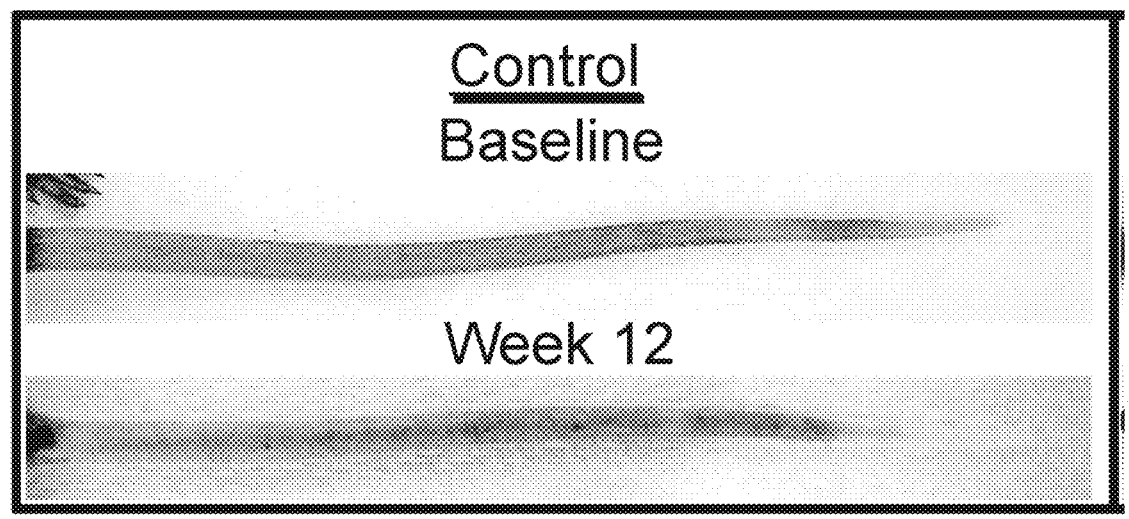
Figure 8B:
Figure 8C:
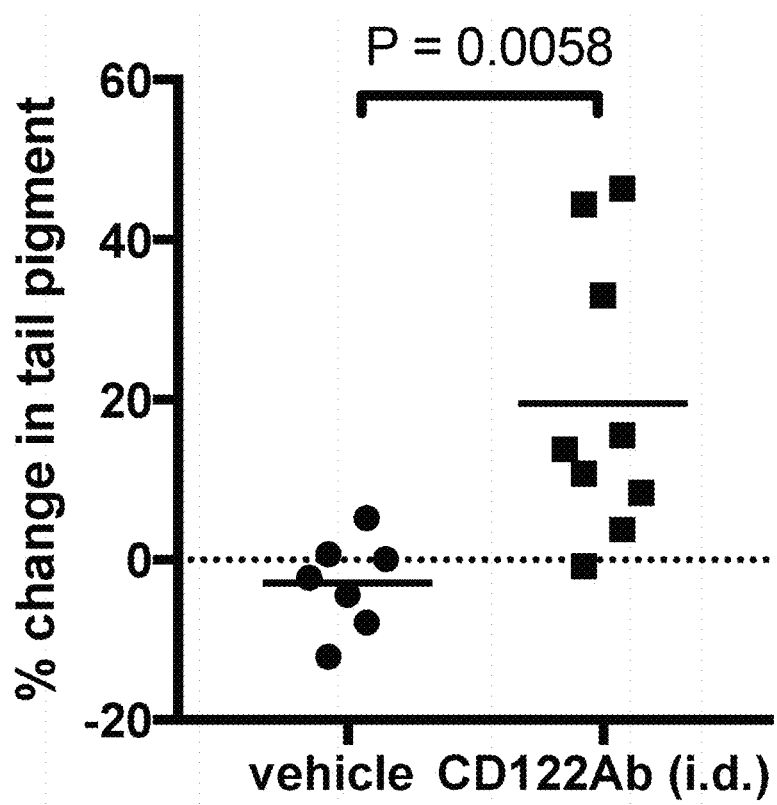
Figure 8D:
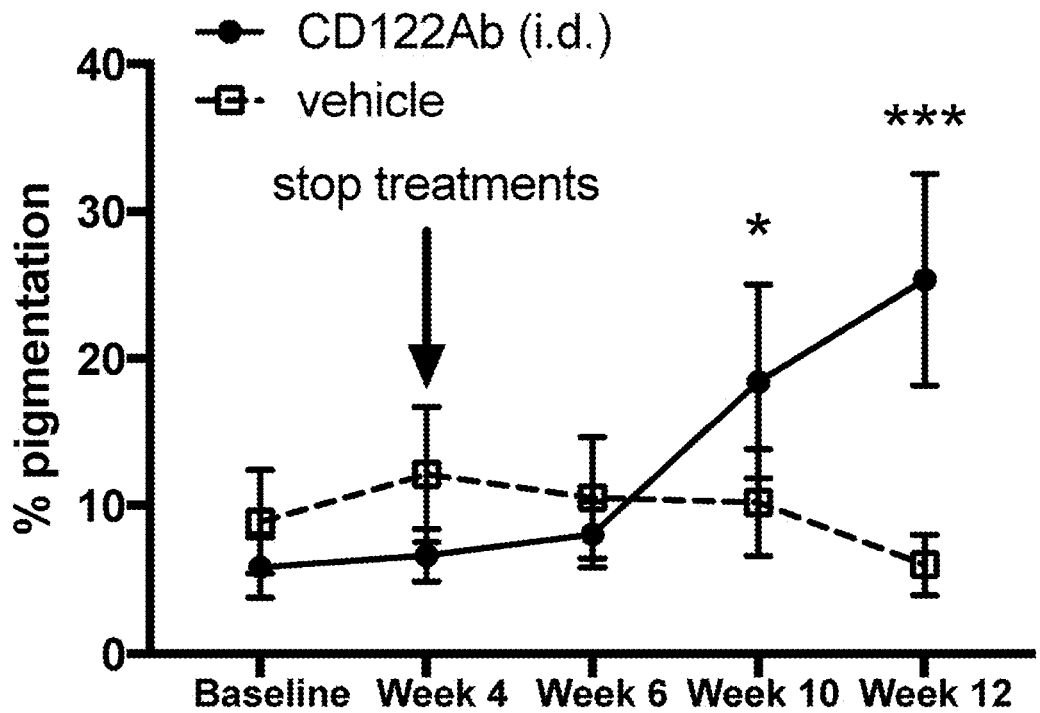
Figure 8E:
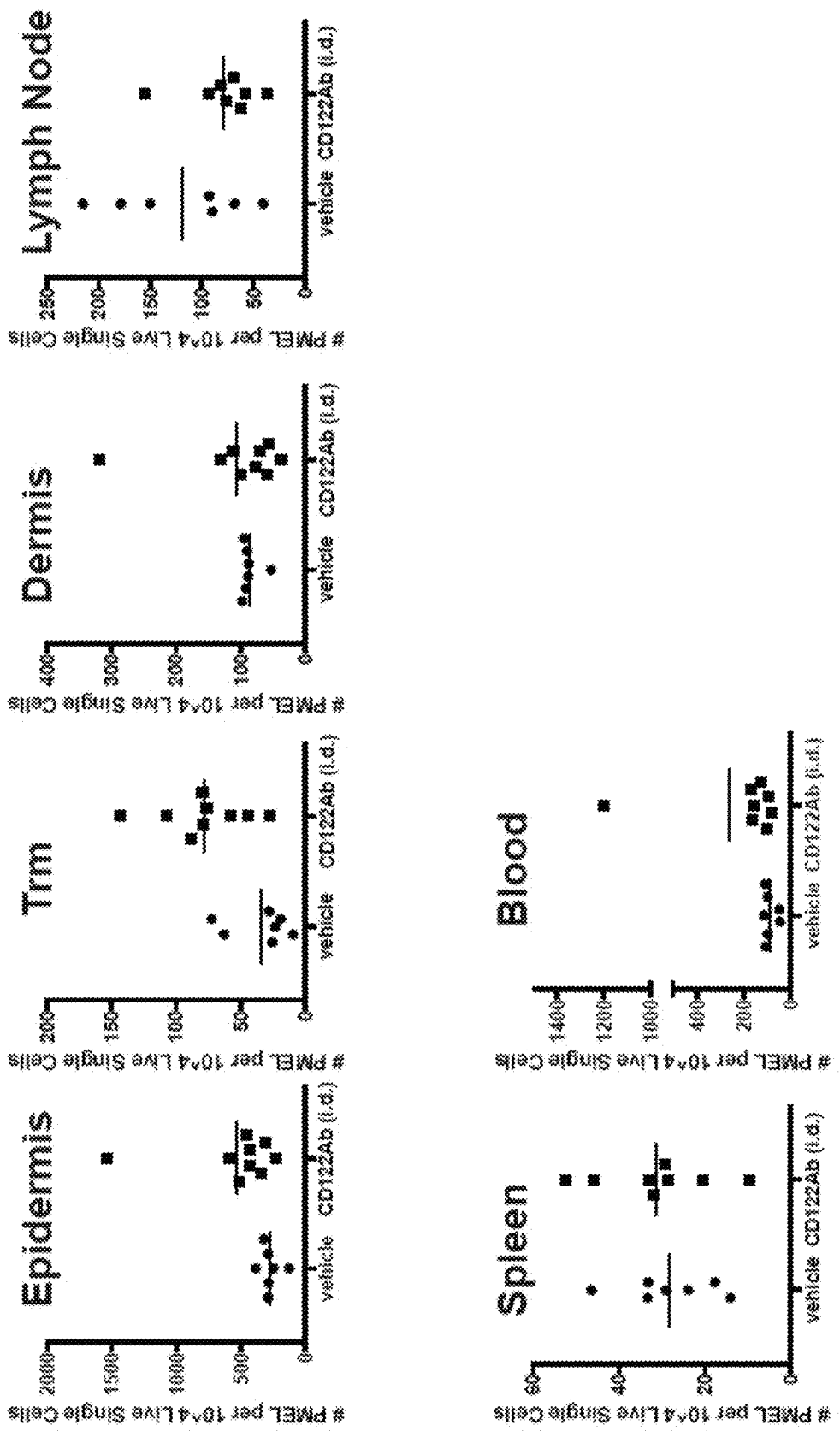
Figures 9A, 9B, 9C, 9D, 9E:
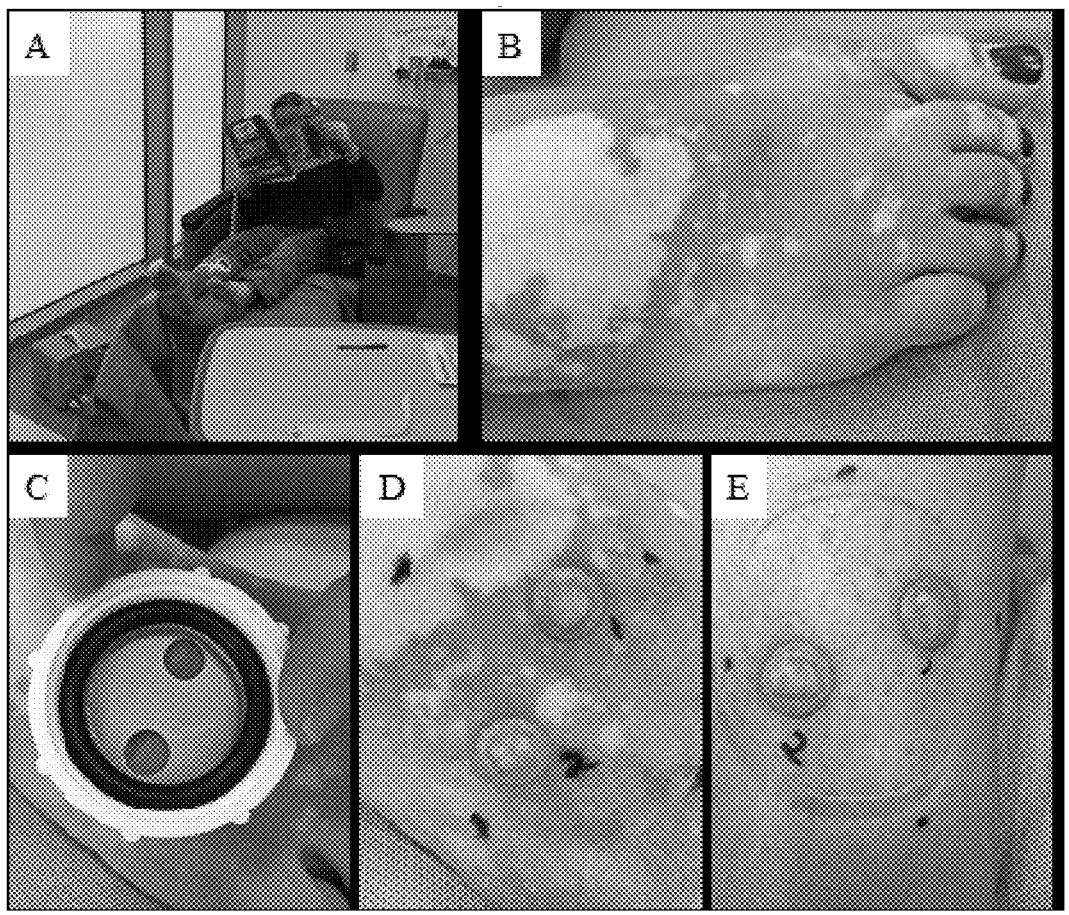
FIGS. 9A-9F. Skin blistering set up and tissue analysis. (A) Clinical setup, subject during blistering procedure. (B) Vitiligo confetti-like depigmentation on foot. (C) Placement of orifice plate for negative pressure chamber. (D,E) Formed blisters on (D) lesional skin and (E) non-lesional skin. (F) Blister tissue analysis: blister fluid (skin interstitial fluid) was withdrawn through a needle and analyzed by flow cytometry and ELISA. Blister roof (epidermis) was processed for RNA extraction for gene expression analysis.
Figure 9F:
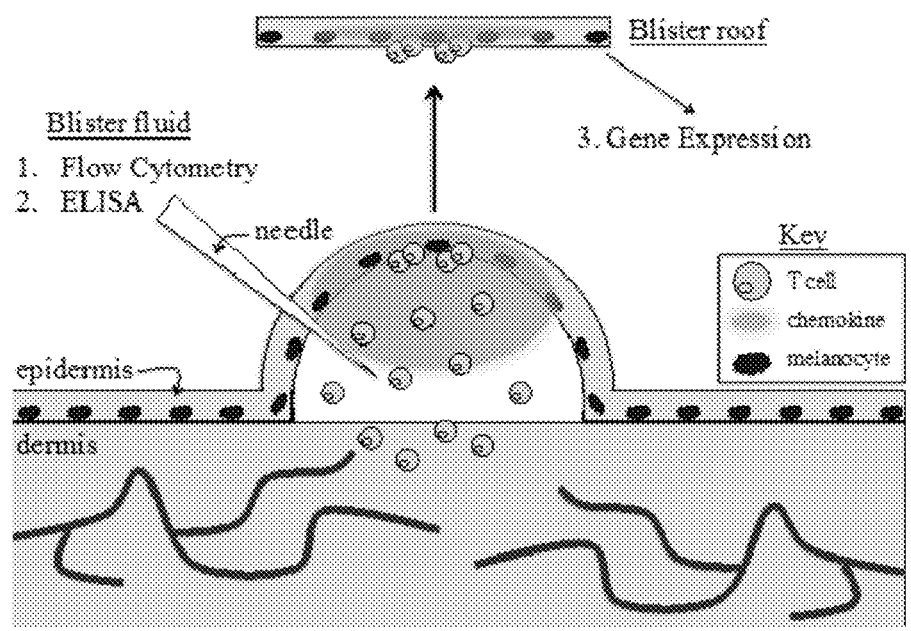

After 8 weeks of systemic treatment, we saw significant repigmentation in treated mice compared to controls (FIG. 6A-C). We found that PMEL were depleted from the epidermis in longstanding lesions, and within the PMEL population, Trm (CD69+, CD103+) were largely affected. There were also fewer PMEL in the dermis, lymph nodes, spleen, and blood of treated mice compared to controls (FIG. 6D). However, IL-15Rβ antibody treatment had small effects on host CD8+ T cell populations, indicating that targeting this pathway may preferentially have an effect on autoreactive cells (FIG. 6E). To determine whether IL-15Rβ blockade provided a durable treatment option, we treated mice with IL-15Rβ antibody for only 2 weeks, then stopped treatment and observed repigmentation over a full 8-week period. Treatment with this short-term approach resulted in significant repigmentation over the total 10-week period (FIG. 6F-I). Analysis of PMEL depletion following short-term IL-15Rβ antibody treatment revealed variable effects in the lymph node, spleen, blood and skin (Table 2). Therefore, we performed a systemic functionality study in which mice with vitiligo were dosed for 2 weeks, but PMEL were restimulated in vitro with 3 μg/mL plate bound anti-CD3 with 2 g/mL soluble anti-CD28. Cytokine production was assessed via flow cytometry and we found that PMEL from the skin of mice treated with anti-CD122 antibody made significantly less IFNγ than PMEL from control animals, indicating that short-term treatment affects T cell function (FIG. 7A-C). To evaluate whether local injection of antibody could induce a durable treatment response similar to systemic administration, another durability study was conducted using intradermal injection of IL-15Rβ antibody. We treated mice with established vitiligo with CD122 antibody intradermally for 4 weeks (2 weeks at 5 μg for loading dose, and 2 weeks at 1 μg for maintenance dose), then stopped treatment and observed repigmentation over a 10-week period. Similar to the systemic durability study, experimental mice treated with intradermal CD122 antibody had significant repigmentation compared to control mice without depletion of PMEL T cells (FIG. 8). This suggests that targeting IL-15 in the skin in vitiligo, unlike existing therapies, could provide a durable treatment option for patients, with longstanding effects after a limited treatment course.

TABLE 2

PMEL analysis in IL-15Rβ antibody durability studies.

| IL-15Rβ antibody lot/experiment | PMEL population | Average # normalized to 9^4 live singlets ± SEM | P value summary (t test) | Significant depletion? |
| --- | --- | --- | --- | --- |
| Lot A- experiment 1 | Trm | IL-15Rβ Ab: 105.5 ± 34.28 Veh: 162.5 + 55.87 | 0.4067 | No |
|  | Tcm spleen | IL-15Rβ Ab: 6.53 ± 1.575 Veh: 34.31 + 9.31 | *0.0283 | Yes |
|  | Tcm lymph node | IL-15Rβ Ab: 21.38 ± 5.585 Veh: 68.73 + 18.88 | *0.0228 | Yes |
| Lot A- experiment 2 | Trm | IL-15Rβ Ab: 54.63 ± 14.7 Veh: 164 + 44.08 | *0.0457 | Yes |

TABLE 2-continued

PMEL analysis in IL-15Rβ antibody durability studies.

| IL-15Rβ antibody lot/experiment | PMEL population | Average # normalized to 9^4 live singlets ± SEM | P value summary (t test) | Significant depletion? |
|---|---|---|---|---|
| | Tcm spleen | IL-15Rβ Ab: 9.83 ± 2.582 Veh: 9.35 + 4.018 | 0.8065 | No |
| | Tcm lymph node | IL-15Rβ Ab: 15.78 ± 5.838 Veh: 12.58 + 2.676 | 0.5602 | No |
| Summary lot A experiments 1 & 2 | Trm | IL-15Rβ Ab: 76.64 ± 17.43 Veh: 163.4 + 32.1 | *0.0308 | Yes |
| | Tcm spleen | IL-15Rβ Ab: 8.418 ± 1.575 Veh: 18.34 + 5.032 | 0.1057 | No |
| | Tcm lymph node | IL-15Rβ Ab: 17.34 ± 4.44 Veh: 36.7 + 14.03 | 0.1745 | No |
| Lot B- experiment 3 | Trm | IL-15Rβ Ab: 218.1 ± 95.5 Veh: 54.18 + 21.71 | 0.1566 | No |
| | Tcm spleen | IL-15Rβ Ab: 20.76 ± 5.577 Veh: 30.77 + 5.763 | 0.3045 | No |
| | Tcm lymph node | IL-15Rβ Ab: 31.15 ± 5.635 Veh: 43.78 + 8.855 | 0.391 | No |
| Summary of all 3 experiments | Trm | IL-15Rβ Ab: 134.6 ± 41.05 Veh: 126.5 + 25.56 | 0.7767 | No |
| | Tcm spleen | IL-15Rβ Ab: 12.84 ± 2.465 Veh: 23.17 + 4.635 | 0.0521 | No |
| | Tcm lymph node | IL-15Rβ Ab: 22.27 ± 3.714 Veh: 38.73 + 8.55 | 0.0851 | No |

Example 6. Vitiligo Activity Assessment

The present inventors discovered that the IFN-γ-chemokine axis plays a critical role in the progression and maintenance of vitiligo, and hypothesize that targeting this axis will be an effective, new targeted treatment strategy (Harris et al., 2012; Rashighi et al., 2014; Rashighi and Harris, 2015). Serum levels of the IFN-γ-dependent chemokine CXCL10 were elevated in vitiligo patients compared to healthy controls (Rashighi et al., 2014). Others have validated these findings in additional vitiligo patients, and one study reported that serum CXCL9 and CXCL10 levels correlated with disease activity and decreased after systemic immunosuppression (Regazzetti et al., 2015; Wang et al., 2016). Two vitiligo patients rapidly repigmented following treatment with two different JAK inhibitors that both interfere with IFN-γ signaling (Craiglow and King, 2015; Harris et al., 2016), and a case series reported that topical ruxolitinib was effective for vitiligo patients (Rothstein et al., 2017). One patient had elevated serum CXCL10 for over a year off of treatment that corrected 2-3 months after starting treatment with ruxolitinib, suggesting that targeted therapies could result in detectable changes in components of IFN-γ-induced inflammatory markers.

However, a caveat of using serum cytokines as markers of disease activity is that while a large group of vitiligo patients (n=30 or more in existing studies) have average chemokine levels statistically higher than healthy controls, many subjects have undetectable levels and the standard deviation is high, precluding identification of a "normal" vs. "abnormal" value. In addition, serum cytokines are not organ- or disease-specific, so patients with other sources of inflammation (multiple autoimmune diseases are common in vitiligo patients) have elevated levels that are unrelated to vitiligo disease activity (Antonelli et al., 2011; Rotondi et al., 2005). Thus, serum chemokines are not sensitive or specific for disease activity, and are therefore unlikely to be reliable markers of treatment response. A reliable method to sample lesional skin and reliably capture markers of inflammation is needed.

Suction blister biopsies: To induce blisters in vitiligo patient skin as a minimally invasive method to sample vitiligo lesions, we used the NP-4 negative pressure instrument (Electronic Diversities, Finksburg, MD), which creates an adjustable suction through a warmed aluminum orifice plate. Blisters form with minimal discomfort in 30-45 minutes at the site of lem openings in the plate. Up to 4 chambers can be used at a time, each with up to 5 openings, for up to 20 blisters. Blister fluid is extracted through a 30-guage needle, and the blister roof is removed with iris scissors and gradle forceps (FIGS. 9A-F). The roof was stored at −80° C., fluid centrifuged at 330× g for 5 minutes, and the supernatant removed and stored at −80° C. The cellular pellet was resuspended in FACS buffer, cells stained with live/dead blue (viability) and fluorescent antibodies against CD45 (immune cells), CD3 (T cells), and CD8 (cytotoxic T cells), and analyzed on a FACSCalibur flow cytometer. Stored blister fluid supernatant was analyzed for IFN-γ, CXCL9, CXCL10, and CXCL11 by ELISA (R&D Systems, Minneapolis, MN). The stored blister roof was processed for RNA isolation (RNeasy, Qiagen).

$CD8^+$ T cells and CXCL9 protein are elevated in lesional skin: Eight subjects with clinical evidence of active vitiligo lesions (confetti depigmentation, see (Sosa et al., 2015)) and off all treatment participated (Strassner et al., 2017). Six blisters were induced per patient: 2 in one lesion, 2 in a separate lesion, and 2 in non-lesional skin. Seven healthy subjects contributed 3 blisters each in normal-appearing skin. Blister fluid $CD8^+$ T cells and total $CD45^+$ cells were averaged between blisters. We calculated the ratio of $CD8^+$ T cells to $10^4$ total $CD45^+$ cells (CD8:CD45), which was elevated in lesional blister fluid vs. non-lesional fluid in all subjects tested (p=0.005, paired, 2-tailed T test), ranging from 2-fold to 25-fold. The Receiver Operating Characteristic (ROC) curve is a method to determine the sensitivity and specificity of an assay for separating disease and control subjects. It can be used to set a threshold value that best represents "normal" vs. "disease". The ROC curve for CD8:CD45 in blister fluid was highly significant (p=0.0002) and revealed that this test alone had decent sensitivity (lesions consistently positive) and specificity (non-lesions consistently negative) to separate vitiligo lesions from non-lesional and healthy control skin: A threshold value of >912 $CD8^+$ T cells had 83% sensitivity and 61% specificity for detecting active lesional skin (FIGS. 10A-C). We also quantified T cells without normalization, or normalized to total single cells or blister fluid volume, but these were not significant, and lesional blister roof T cells were not significantly different from non-lesional in the subjects tested (not shown). This suggests that the fluid $CD8^+$ T cell: $CD45^+$ cell ratio is the best method for comparison.

Figures 11A, 11B, 11C:
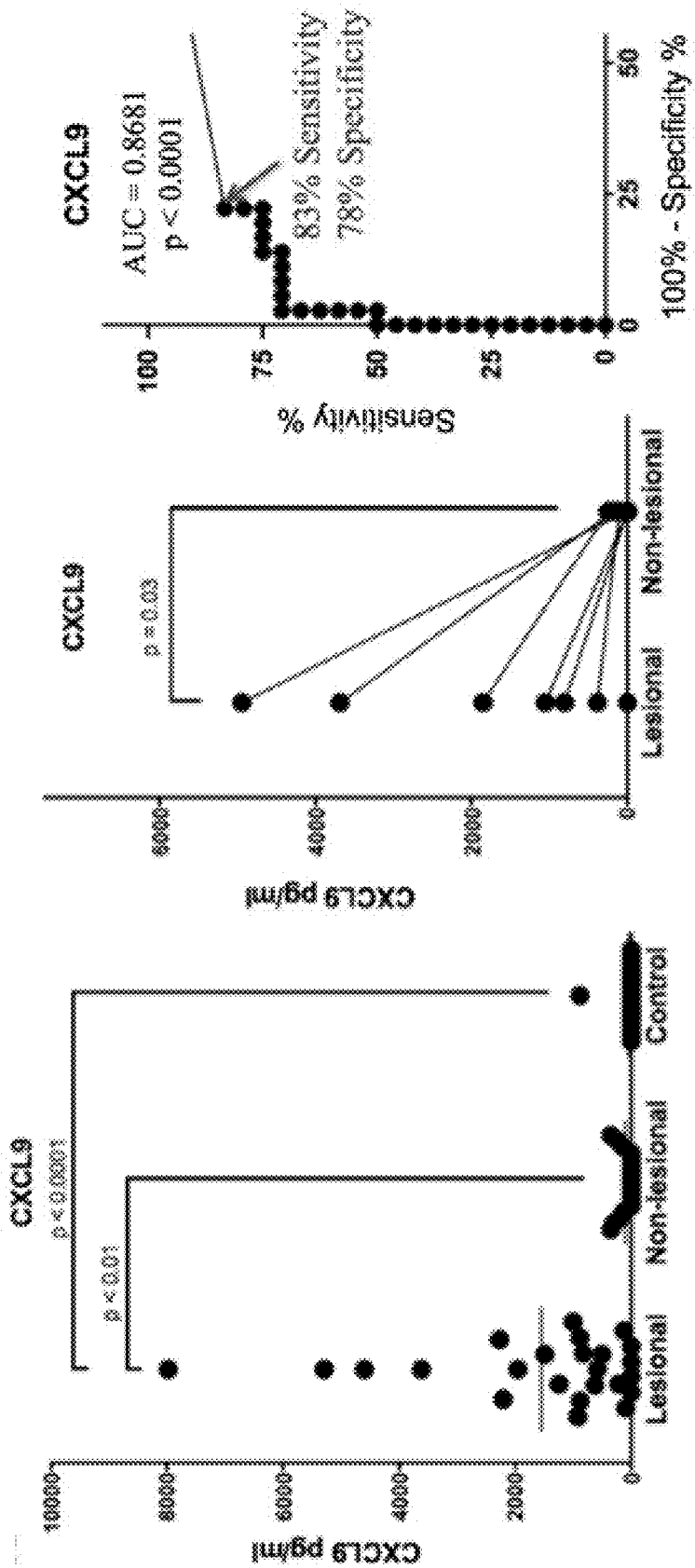

Cytokine proteins in blister fluid were quantified by enzyme-linked immunosorbent assay (ELISA). We found that IFN-γ and CXCL11 were undetectable in all lesions tested. CXCL10 was inconsistently elevated in a small number of blisters, but this was not statistically significant in the subjects tested (not shown). However, CXCL9 protein was consistently elevated in the majority of lesional blisters tested, and there was minimal detectable CXCL9 protein in non-lesional or healthy control blisters, suggesting that this could be a more sensitive and specific marker for disease activity (Strassner et al., 2017). Paired lesional: non-lesional comparison was statistically significant in the subjects tested (p=0.03, paired, 2-tailed T test), with increases ranging from 2-fold to many thousand-fold. The ROC curve for CXCL9 blister fluid protein was highly significant (p<0.0001) and revealed that this test alone had good sensitivity and specificity to separate vitiligo lesions from both non-lesional and healthy control skin: A threshold value of >48 pg/ml CXCL9 had 83% sensitivity and 78% specificity for detecting active lesional skin, while a threshold of >429 pg/ml had 71% sensitivity and 97% specificity (FIGS. 11A-C). This suggests that CXCL9 protein is the most sensitive and specific cytokine in blister fluid for comparison.

In addition to obtaining blister roofs for gene expression analysis as described above, samples could also be obtained by tape stripping the skin and performing expression analysis on the removed skin cells.

Figure 12A:
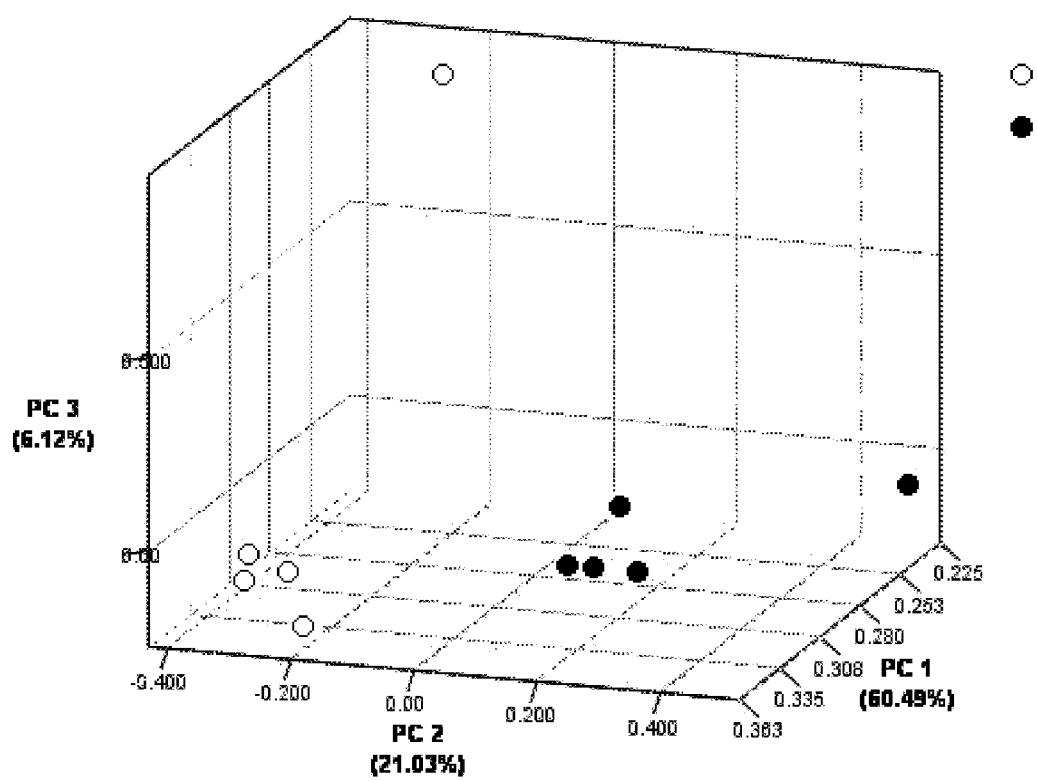
FIGS. 12A-12B. Using a panel of vitiligo-specific genes to understand disease activity. Whole genome expression was analyzed in vitiligo lesions compared to healthy control skin. Principal component analysis (12A) of a panel of 20 differentially expressed genes (12B) reflect the presence of CD8+ T cells, IFN-γ signaling, and absence of melanocyte markers.
Figure 12B:
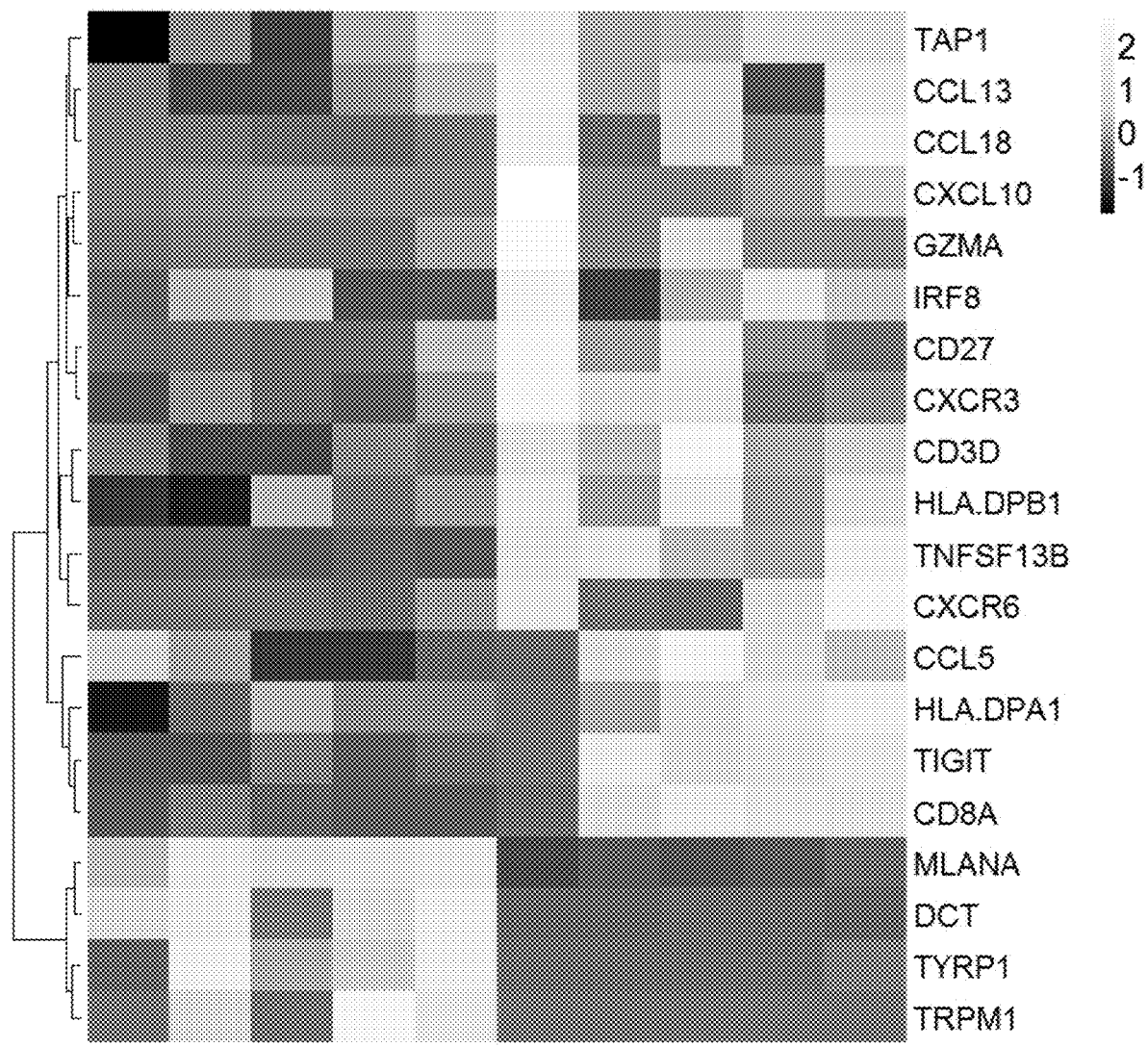

Gene expression in active lesional skin: We previously published the gene expression profile of 5 vitiligo patients/5 controls (whole genome Illumina DASL), which we then validated in an additional 8 patients/3 controls (Nanostring, inflammation code set). This revealed an IFN-γ signature in active lesional skin that included the chemokines CXCL9, 10, and 11 as the genes with most highly elevated expression (Rashighi et al., 2014). Subsequent principal component (PC) analysis revealed a panel of 20 genes that efficiently separate diseased from control subjects. This panel is comprised of 3 distinct gene sets: 1) markers of a $CD8^+$ T cell response, 2) markers of IFN-γ-induced inflammation, and 3) melanocyte-specific markers. Active lesional skin reflects increased expression of $CD8^+$ T cell genes, increased expression of IFN-γ-induced genes, and decreased expression of melanocyte-specific genes, and each set is reflected by a different axis (FIGS. 12A-B). We hypothesized that $CD8^+$ T cell genes and IFN-γ-induced genes will decrease while melanocyte-specific genes increase following treatment. We have isolated RNA from blister roofs and demonstrated that it is of high integrity (high RNA integrity number on Bioanalyzer analysis) and provides good material for RT-PCR analysis of housekeeping genes (not shown).

Vitiligo biomarkers: The vitiligo biomarkers to be used to assess patient disease activity are comprised of 3 parameters: 1) $CD8^+$ T cell numbers normalized to $CD45^+$ immune cells in blister fluid; 2) CXCL9 protein concentration (pg/ml) in blister fluid; and 3) 20 differentially expressed genes in the epidermal blister roof, although either of these parameters could be used as markers of disease activity alone, as well (Strassner et al., 2017). The panel of differentially expressed genes can be quantified into a single score by calculating the Mahalanobis distance across the expression data, an approach that not only takes into account the direction of the expression (so that a positive expression does not cancel out a negative expression) but also the covariance of the gene expressions. The Mahalanobis distance accounts for the variance of each variable and the covariance between variables by transforming the data into standardized uncorrelated data and computing the ordinary Euclidean distance for the transformed data. In this way, the Mahalanobis distance is like a univariate z-score: it provides a way to measure distances that takes into account the scale of the data. We use an approach such as Stouffer's Z-score method (essentially an average of the z-scores) to combine the z-scores into a single z-score for the gene expression panel. Each parameter (CD8+ T cell numbers and CXCL9 protein concentration) in lesional skin will be divided by the parameter in non-lesional skin, resulting in a fold change in lesional vs. non-lesional skin. All three parameters can be compared to assess disease activity by transforming the fold-change results into z-scores and then again using Stouffer's z-score method to combine them into a single z-score for each subject.

REFERENCES

Adachi, T., Kobayashi, T., Sugihara, E., Yamada, T., Ikuta, K., Pittaluga, S., Saya, H., Amagai, M., and Nagao, K.

(2015). Hair follicle-derived IL-7 and IL-15 mediate skin-resident memory T cell homeostasis and lymphoma. Nat Med 21, 1272-1279.

Agarwal, P., Rashighi, M., Essien, K. I., Richmond, J. M., Randall, L., Pazoki-Toroudi, H., Hunter, C. A., and Harris, J. E. (2015). Simvastatin prevents and reverses depigmentation in a mouse model of vitiligo. J Invest Dermatol 135, 1080-1088.

Ahmadian, A., Gharizadeh, B., Gustafsson, A. C., Sterky, F., Nyren, P., Uhlen, M., and Lundeberg, J. (2000). Single-nucleotide polymorphism analysis by pyrosequencing. Anal Biochem 280, 103-110.

Alikhan, A., Felsten, L. M., Daly, M., and Petronic-Rosic, V. (2011). Vitiligo: a comprehensive overview Part I. Introduction, epidemiology, quality of life, diagnosis, differential diagnosis, associations, histopathology, etiology, and work-up. Journal of the American Academy of Dermatology 65, 473-491.

Altschul, S. F., Gish, W., Miller, W., Myers, E. W., and Lipman, D. J. (1990). Basic local alignment search tool. Journal of molecular biology 215, 403-410.

Antonelli, A., Ferrari, S. M., Frascerra, S., Galetta, F., Franzoni, F., Corrado, A., Miccoli, M., Benvenga, S., Paolicchi, A., Ferrannini, E., et al. (2011). Circulating chemokine (CXC motif) ligand (CXCL) 9 is increased in aggressive chronic autoimmune thyroiditis, in association with CXCL10. Cytokine 55, 288-293.

Ariotti, S., M A Hogenbirk, F E Dijkgraaf, L L Visser, M E Hoekstra, J Y Song, H Jacobs, J B Haanen, and T N Schumacher (2014). Skin-resident memory CD8+ T cells trigger a state of tissue-wide pathogen alert. Science.

Babu, A., Thappa, D. M., and Jaisankar, T. J. (2008). Punch grafting versus suction blister epidermal grafting in the treatment of stable lip vitiligo. Dermatologic surgery: official publication for American Society for Dermatologic Surgery [et al] 34, 166-178; discussion 178.

Baigude, H., and Rana, T. M. (2014). Strategies to antagonize miRNA functions in vitro and in vivo. Nanomedicine (Lond) 9, 2545-2555.

Bartel, D. P., and Szostak, J. W. (1993). Isolation of new ribozymes from a large pool of random sequences [see comment]. Science 261, 1411-1418.

Beaudry, A. A., and Joyce, G. F. (1992). Directed evolution of an RNA enzyme. Science 257, 635-641.

Benton, W. D., and Davis, R. W. (1977). Screening lambdagt recombinant clones by hybridization to single plaques in situ. Science 196, 180-182.

Bernard, P. S., and Wittwer, C. T. (2002). Real-time PCR technology for cancer diagnostics. Clin Chem 48, 1178-1185.

Bernardo, B. C., Ooi, J. Y., Lin, R. C., and McMullen, J. R. (2015). miRNA therapeutics: a new class of drugs with potential therapeutic applications in the heart. Future Med Chem 7, 1771-1792.

Bhatnagar, A., Kanwar, A. J., Parsad, D., and De, D. (2007). Psoralen and ultraviolet A and narrow-band ultraviolet B in inducing stability in vitiligo, assessed by vitiligo disease activity score: an open prospective comparative study. J Eur Acad Dermatol Venereol 21, 1381-1385.

Bianchi, F., Nicassio, F., Marzi, M., Belloni, E., Dall'olio, V., Bernard, L., Pelosi, G., Maisonneuve, P., Veronesi, G., and Di Fiore, P. P. (2011). A serum circulating miRNA diagnostic test to identify asymptomatic high-risk individuals with early stage lung cancer. EMBO Mol Med 3, 495-503.

Braasch, D. A., and Corey, D. R. (2002). Novel antisense and peptide nucleic acid strategies for controlling gene expression. Biochemistry 41, 4503-4510.

Breaker, R. R. (1996). Are engineered proteins getting competition from RNA? Curr Opin Biotechnol 7, 442-448.

Breaker, R. R., and Joyce, G. F. (1994). Inventing and improving ribozyme function: rational design versus iterative selection methods. Trends Biotechnol 12, 268-275.

Brody, E. N., Gold, L., Lawn, R. M., Walker, J. J., and Zichi, D. (2010). High-content affinity-based proteomics: unlocking protein biomarker discovery. Expert Rev Mol Diagn 10, 1013-1022.

Brummelkamp, T. R., Bernards, R., and Agami, R. (2002). A system for stable expression of short interfering RNAs in mammalian cells. Science 296, 550-553.

Cavalie, M., Ezzedine, K., Fontas, E., Montaudie, H., Castela, E., Bahadoran, P., Taieb, A., Lacour, J. P., and Passeron, T. (2015). Maintenance therapy of adult vitiligo with 0.1% tacrolimus ointment: a randomized, double blind, placebo-controlled study. J Invest Dermatol 135, 970-974.

Chiba, K. (2005). FTY720, a new class of immunomodulator, inhibits lymphocyte egress from secondary lymphoid tissues and thymus by agonistic activity at sphingosine 1-phosphate receptors. Pharmacology & therapeutics 108, 308-319.

Christoffersen, R. E., and Marr, J. J. (1995). Ribozymes as human therapeutic agents. J Med Chem 38, 2023-2037.

Clark, R. A., Watanabe, R., Teague, J. E., Schlapbach, C., Tawa, M. C., Adams, N., Dorosario, A. A., Chaney, K. S., Cutler, C. S., Leboeuf, N. R., et al. (2012). Skin effector memory T cells do not recirculate and provide immune protection in alemtuzumab-treated CTCL patients. Sci Transl Med 4, 117ra117.

Craiglow, B. G., and King, B. A. (2015). Tofacitinib Citrate for the Treatment of Vitiligo: A Pathogenesis-Directed Therapy. JAMA dermatology 151, 1110-1112.

Cummings, R. J., Mitra, S., Lord, E. M., and Foster, T. H. (2008). Antibody-labeled fluorescence imaging of dendritic cell populations in vivo. J Biomed Opt 13, 044041.

Damsky, W., and King, B. A. (2017). JAK inhibitors in dermatology: The promise of a new drug class. Journal of the American Academy of Dermatology 76, 736-744.

DeGottardi, M. Q., Okoye, A. A., Vaidya, M., Talla, A., Konfe, A. L., Reyes, M. D., Clock, J. A., Duell, D. M., Legasse, A. W., Sabnis, A., et al. (2016). Effect of Anti-IL-15 Administration on T Cell and NK Cell Homeostasis in Rhesus Macaques. J Immunol 197, 1183-1198.

Diehl, F., Li, M., He, Y., Kinzler, K. W., Vogelstein, B., and Dressman, D. (2006). BEAMing: single-molecule PCR on microparticles in water-in-oil emulsions. Nat Methods 3, 551-559.

Epron, G., Ame-Thomas, P., Le Priol, J., Pangault, C., Dulong, J., Lamy, T., Fest, T., and Tarte, K. (2012). Monocytes and T cells cooperate to favor normal and follicular lymphoma B-cell growth: role of IL-15 and CD40L signaling. Leukemia 26, 139-148.

Figueira, M. F., Monnerat-Cahli, G., Medei, E., Carvalho, A. B., Morales, M. M., Lamas, M. E., da Fonseca, R. N., and Souza-Menezes, J. (2014). MicroRNAs: potential therapeutic targets in diabetic complications of the cardiovascular and renal systems. Acta Physiol (Oxf) 211, 491-500.

Frenkel, K., Wei, L., and Wei, H. (1995). 7,12-dimethylbenz[a]anthracene induces oxidative DNA modification in vivo. Free radical biology & medicine 19, 373-380.

Gebhardt, T., Wakim, L. M., Eidsmo, L., Reading, P. C., Heath, W. R., and Carbone, F. R. (2009). Memory T cells in nonlymphoid tissue that provide enhanced local immunity during infection with herpes simplex virus. Nat Immunol 10, 524-530.

Grimes, P. E. (2005). New insights and new therapies in vitiligo. JAMA 293, 730-735.

Grunstein, M., and Hogness, D. S. (1975). Colony hybridization: a method for the isolation of cloned DNAs that contain a specific gene. Proc Natl Acad Sci USA 72, 3961-3965.

Gupta, S., Jain, V. K., and Saraswat, P. K. (1999a). Suction blister epidermal grafting versus punch skin grafting in recalcitrant and stable vitiligo. Dermatologic surgery: official publication for American Society for Dermatologic Surgery [et al] 25, 955-958.

Gupta, S., Shroff, S., and Gupta, S. (1999b). Modified technique of suction blistering for epidermal grafting in vitiligo. International journal of dermatology 38, 306-309.

Hamajima, K., Sasaki, S., Fukushima, J., Kaneko, T., Xin, K. Q., Kudoh, I., and Okuda, K. (1998). Intranasal administration of HIV-DNA vaccine formulated with a polymer, carboxymethylcellulose, augments mucosal antibody production and cell-mediated immune response. Clinical immunology and immunopathology 88, 205-210.

Harris, J. E., Harris, T. H., Weninger, W., Wherry, E. J., Hunter, C. A., and Turka, L. A. (2012). A mouse model of vitiligo with focused epidermal depigmentation requires IFN-gamma for autoreactive CD8(+) T-cell accumulation in the skin. J Invest Dermatol 132, 1869-1876.

Harris, J. E., Rashighi, M., Nguyen, N., Jabbari, A., Ulerio, G., Clynes, R., Christiano, A. M., and Mackay-Wiggan, J. (2016). Rapid skin repigmentation on oral ruxolitinib in a patient with coexistent vitiligo and alopecia areata (AA). Journal of the American Academy of Dermatology 74, 370-371.

Hechinger, A. K., Smith, B. A., Flynn, R., Hanke, K., McDonald-Hyman, C., Taylor, P. A., Pfeifer, D., Hackanson, B., Leonhardt, F., Prinz, G., et al. (2015). Therapeutic activity of multiple common gamma-chain cytokine inhibition in acute and chronic GVHD. Blood 125, 570-580.

Jepsen, J. S., Sorensen, M. D., and Wengel, J. (2004). Locked nucleic acid: a potent nucleic acid analog in therapeutics and biotechnology. Oligonucleotides 14, 130-146.

Jiang, X., Clark, R. A., Liu, L., Wagers, A. J., Fuhlbrigge, R. C., and Kupper, T. S. (2012). Skin infection generates non-migratory memory CD8+ T (RM) cells providing global skin immunity. Nature 483, 227-231.

Joyce, G. F. (1989). Amplification, mutation and selection of catalytic RNA. Gene 82, 83-87.

Joyce, G. F. (1992). Directed molecular evolution. Sci Am 267, 90-97.

Kauppinen, S., Vester, B., and Wengel, J. (2005). Locked nucleic acid (LNA): High affinity targeting of RNA for diagnostics and therapeutics. Drug Discov Today Technol 2, 287-290.

Kim, Y., Kim, H., Kim, S. Y., Lee, H. K., Kwon, H. J., Kim, Y. G., Lee, J., Kim, H. M., and So, B. H. (2010). Automated heart-type fatty acid-binding protein assay for the early diagnosis of acute myocardial infarction. Am J Clin Pathol 134, 157-162.

Kim, Y. S., Maslinski, W., Zheng, X. X., Stevens, A. C., Li, X. C., Tesch, G. H., Kelley, V. R., and Strom, T. B. (1998). Targeting the IL-15 receptor with an antagonist IL-15 mutant/Fc gamma2a protein blocks delayed-type hypersensitivity. J Immunol 160, 5742-5748.

Kumar, P. K., and Ellington, A. D. (1995). Artificial evolution and natural ribozymes. FASEB J 9, 1183-1195.

Lee, N. S., Dohjima, T., Bauer, G., Li, H., Li, M. J., Ehsani, A., Salvaterra, P., and Rossi, J. (2002). Expression of small interfering RNAs targeted against HIV-1 rev transcripts in human cells. Nat Biotechnol 20, 500-505.

Levin, J. D., Fiala, D., Samala, M. F., Kahn, J. D., and Peterson, R. J. (2006). Position-dependent effects of locked nucleic acid (LNA) on DNA sequencing and PCR primers. Nucleic acids research 34, e142.

Liu, J., Man, W. Y., Lv, C. Z., Song, S. P., Shi, Y. J., Elias, P. M., and Man, M. Q. (2010). Epidermal permeability barrier recovery is delayed in vitiligo-involved sites. Skin Pharmacol Physiol 23, 193-200.

Lotti, T., Gori, A., Zanieri, F., Colucci, R., and Moretti, S. (2008). Vitiligo: new and emerging treatments. Dermatol Ther 21, 110-117.

Mackay, L. K., Rahimpour, A., Ma, J. Z., Collins, N., Stock, A. T., Hafon, M. L., Vega-Ramos, J., Lauzurica, P., Mueller, S. N., Stefanovic, T., et al. (2013). The developmental pathway for CD103(+) CD8+ tissue-resident memory T cells of skin. Nat Immunol 14, 1294-1301.

Mackay, L. K., Stock, A. T., Ma, J. Z., Jones, C. M., Kent, S. J., Mueller, S. N., Heath, W. R., Carbone, F. R., and Gebhardt, T. (2012). Long-lived epithelial immunity by tissue-resident memory T (TRM) cells in the absence of persisting local antigen presentation. Proc Natl Acad Sci USA 109, 7037-7042.

Miranda, K. C., Bond, D. T., McKee, M., Skog, J., Paunescu, T. G., Da Silva, N., Brown, D., and Russo, L. M. (2010). Nucleic acids within urinary exosomes/microvesicles are potential biomarkers for renal disease. Kidney Int 78, 191-199.

Miyagishi, M., and Taira, K. (2002). U6 promoter-driven siRNAs with four uridine 3' overhangs efficiently suppress targeted gene expression in mammalian cells. Nat Biotechnol 20, 497-500.

Moellmann, G., Klein-Angerer, S., Scollay, D. A., Nordlund, J. J., and Lerner, A. B. (1982). Extracellular granular material and degeneration of keratinocytes in the normally pigmented epidermis of patients with vitiligo. J Invest Dermatol 79, 321-330.

Murooka, T. T., Deruaz, M., Marangoni, F., Vrbanac, V. D., Seung, E., von Andrian, U. H., Tager, A. M., Luster, A. D., and Mempel, T. R. (2012). HIV-infected T cells are migratory vehicles for viral dissemination. Nature 490, 283-287.

Nelson, B. H. (2004). IL-2, regulatory T cells, and tolerance. J Immunol 172, 3983-3988.

Nielsen, P. E., M Egholm, RH Berg, O Buchardt (1991). Sequence-selective recognition of DNA by strand displacement with a thymine-substituted polyamide. Science 6, 1497-1500.

Nordstrom, T., Ronaghi, M., Forsberg, L., de Faire, U., Morgenstern, R., and Nyren, P. (2000). Direct analysis of single-nucleotide polymorphism on double-stranded DNA by pyrosequencing. Biotechnol Appl Biochem 31 (Pt 2), 107-112.

Orgel, L. E. (1979). Selection in vitro. Proc R Soc Lond B Biol Sci 205, 435-442.

Paddison, P. J., Caudy, A. A., Bernstein, E., Hannon, G. J., and Conklin, D. S. (2002). Short hairpin RNAs (shRNAs)

induce sequence-specific silencing in mammalian cells. Genes & development 16, 948-958.

Paul, C. P., Good, P. D., Winer, I., and Engelke, D. R. (2002). Effective expression of small interfering RNA in human cells. Nat Biotechnol 20, 505-508.

Pfaffe, T., Cooper-White, J., Beyerlein, P., Kostner, K., and Punyadeera, C. (2011). Diagnostic potential of saliva: current state and future applications. Clin Chem 57, 675-687.

Phillips, M., Beatty, J. D., Cataneo, R. N., Huston, J., Kaplan, P. D., Lalisang, R. I., Lambin, P., Lobbes, M. B., Mundada, M., Pappas, N., et al. (2014). Rapid point-of-care breath test for biomarkers of breast cancer and abnormal mammograms. PloS one 9, e90226.

Pinschewer, D. D., Ochsenbein, A. F., Odermatt, B., Brinkmann, V., Hengartner, H., and Zinkernagel, R. M. (2000). FTY720 immunosuppression impairs effector T cell peripheral homing without affecting induction, expansion, and memory. J Immunol 164, 5761-5770.

Ponting, C. P., Oliver, P. L., and Reik, W. (2009). Evolution and functions of long noncoding RNAs. Cell 136, 629-641.

Rashighi, M., Agarwal, P., Richmond, J. M., Harris, T. H., Dresser, K., Su, M. W., Zhou, Y., Deng, A., Hunter, C. A., Luster, A. D., et al. (2014). CXCL10 is critical for the progression and maintenance of depigmentation in a mouse model of vitiligo. Sci Transl Med 6, 223ra223.

Rashighi, M., and Harris, J. E. (2015). Interfering with the IFN-gamma/CXCL10 pathway to develop new targeted treatments for vitiligo. Ann Transl Med 3, 343.

Regazzetti, C., Joly, F., Marty, C., Rivier, M., Mehul, B., Reiniche, P., Mounier, C., Rival, Y., Piwnica, D., Cavalie, M., et al. (2015). Transcriptional Analysis of Vitiligo Skin Reveals the Alteration of WNT Pathway: A Promising Target for Repigmenting Vitiligo Patients. J Invest Dermatol 135, 3105-3114.

Reinhardt, R. L., Liang, H. E., and Locksley, R. M. (2009). Cytokine-secreting follicular T cells shape the antibody repertoire. Nat Immunol 10, 385-393.

Rossing, N., and Worm, A. M. (1981). Interstitial fluid: exchange of macromolecules between plasma and skin interstitium. Clin Physiol 1, 275-284.

Rothstein, B., Joshipura, D., Saraiya, A., Abdat, R., Ashkar, H., Turkowski, Y., Sheth, V., Huang, V., Au, S. C., Kachuk, C., et al. (2017). Treatment of vitiligo with the topical Janus kinase inhibitor ruxolitinib. Journal of the American Academy of Dermatology.

Rotondi, M., Falorni, A., De Bellis, A., Laureti, S., Ferruzzi, P., Romagnani, P., Buonamano, A., Lazzeri, E., Crescioli, C., Mannelli, M., et al. (2005). Elevated serum interferon-gamma-inducible chemokine-10/CXC chemokine ligand-10 in autoimmune primary adrenal insufficiency and in vitro expression in human adrenal cells primary cultures after stimulation with proinflammatory cytokines. J Clin Endocrinol Metab 90, 2357-2363.

Ruchatz, H., Leung, B. P., Wei, X. Q., McInnes, I. B., and Liew, F. Y. (1998). Soluble IL-15 receptor alpha-chain administration prevents murine collagen-induced arthritis: a role for IL-15 in development of antigen-induced immunopathology. J Immunol 160, 5654-5660.

Schenkel, J. M., Fraser, K. A., Vezys, V., and Masopust, D. (2013). Sensing and alarm function of resident memory CD8(+) T cells. Nat Immunol 14, 509-513.

Skon, C. N., Lee, J. Y., Anderson, K. G., Masopust, D., Hogquist, K. A., and Jameson, S. C. (2013). Transcriptional downregulation of S1pr1 is required for the establishment of resident memory CD8+ T cells. Nat Immunol 14, 1285-1293.

Sosa, J. J., Currimbhoy, S. D., Ukoha, U., Sirignano, S., O'Leary, R., Vandergriff, T., Hynan, L. S., and Pandya, A. G. (2015). Confetti-like depigmentation: A potential sign of rapidly progressing vitiligo. Journal of the American Academy of Dermatology 73, 272-275.

Stenvang, J., Petri, A., Lindow, M., Obad, S., and Kauppinen, S. (2012). Inhibition of microRNA function by antimiR oligonucleotides. Silence 3, 1.

Strassner, J. P., Rashighi, M., Ahmed Refat, M., Richmond, J. M., and Harris, J. E. (2017). Suction blistering the lesional skin of vitiligo patients reveals useful biomarkers of disease activity. J Am Acad Dermatol 76, 847-855 e845.

Sui, G., Soohoo, C., Affar el, B., Gay, F., Shi, Y., Forrester, W. C., and Shi, Y. (2002). A DNA vector-based RNAi technology to suppress gene expression in mammalian cells. Proc Natl Acad Sci USA 99, 5515-5520.

Szostak, J. W. (1992). In vitro genetics. Trends in biochemical sciences 17, 89-93.

Taylor, D. D., and Gercel-Taylor, C. (2013). The origin, function, and diagnostic potential of RNA within extracellular vesicles present in human biological fluids. Frontiers in genetics 4, 142.

Ushio, H. I., Seigo; Adachi, Kunitomo; Oshita, Kouichi; Chiba, Kenji (2008). Phenylpyazoleanilides as Potent Inhibitor of IL-15 Dependent T Cell Proliferation. Part 2: Discovery of a New Drug Candidate, Y-320. Letters in Drug Design & Discovery 5, 292-296.

van den Boorn, J. G., Konijnenberg, D., Dellemijn, T. A., van der Veen, J. P., Bos, J. D., Melief, C. J., Vyth-Dreese, F. A., and Luiten, R. M. (2009). Autoimmune destruction of skin melanocytes by perilesional T cells from vitiligo patients. J Invest Dermatol 129, 2220-2232.

Wang, X., Wang, Q., Wu, J., Jiang, M., Chen, L., Zhang, C., and Xiang, L. (2016). Increased Expression of CXCR3 and its Ligands in Vitiligo Patients and CXCL10 as a Potential Clinical Marker for Vitiligo. Br J Dermatol.

Watanabe, R., Gehad A, Yang C, Scott L L, Teague J E, Schlapbach C, Elco C P, Huang V, Matos T R, Kupper T S, Clark RA (2015). Human skin is protected by four functionally and phenotypically discrete populations of resident and recirculating memory T cells. Sci Transl Med.

Yaghoobi, R., Omidian, M., and Bagherani, N. (2011). Vitiligo: a review of the published work. The Journal of dermatology 38, 419-431.

Yang, J., Wei, F., Schafer, C., and Wong, D. T. (2014). Detection of tumor cell-specific mRNA and protein in exosome-like microvesicles from blood and saliva. PloS one 9, e110641.

Yasun, E., Gulbakan, B., Ocsoy, I., Yuan, Q., Shukoor, M. I., Li, C., and Tan, W. (2012). Enrichment and detection of rare proteins with aptamer-conjugated gold nanorods. Analytical chemistry 84, 6008-6015.

Yu, J. Y., DeRuiter, S. L., and Turner, D. L. (2002). RNA interference by expression of short-interfering RNAs and hairpin RNAs in mammalian cells. Proc Natl Acad Sci USA 99, 6047-6052.

Zhang, J., and Madden, T. L. (1997). PowerBLAST: a new network BLAST application for interactive or automated sequence analysis and annotation. Genome research 7, 649-656.

Zhang, X., Sun, S., Hwang, I., Tough, D. F., and Sprent, J. (1998). Potent and selective stimulation of memory-phenotype CD8+ T cells in vivo by IL-15. Immunity 8, 591-599.

Zhu, J., Peng, T., Johnston, C., Phasouk, K., Kask, A. S., Klock, A., Jin, L., Diem, K., Koelle, D. M., Wald, A., et al. (2013). Immune surveillance by CD8alphaalpha+ skin-resident T cells in human herpes virus infection. Nature 497, 494-497.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating vitiligo in a subject, the method comprising:
   identifying a subject having vitiligo; and
   administering to the subject an anti-CD122 antibody at a dose and for a duration sufficient to reverse at least portion of the vitiligo, wherein the antibody is a humanized antibody comprising a heavy chain variable region (VH) comprising a VHCDR1, VHCDR2, and VHCDR3 from antibody ChMBC7 and a light chain variable region (VL) comprising a VLCDR1, VLCDR2, and VLCDR3 from antibody ChMBC7, or the antibody is HuABC2 or HUABC101.

2. The method of claim 1, wherein the anti-CD122 antibody is administered to a vitiligo lesion on the subject.

3. The method of claim 2, wherein the anti-CD122 antibody is administered to an epidermis within the lesion.

4. The method of claim 1, wherein the anti-CD122 antibody is administered subcutaneously.

5. The method of claim 1, wherein the anti-CD122 antibody is administered intradermally.

6. The method of claim 1, wherein the anti-CD122 antibody is administered by a microneedle array.

7. The method of claim 1, wherein the subject is a human subject.

8. The method of claim 1, wherein the subject is administered the anti-CD122 antibody for at least 2 weeks, 4 weeks, 6 weeks, 8 weeks, or 10 weeks.

9. The method of claim 1, wherein the subject is first administered a loading dose and then a maintenance dose.

* * * * *